US009567606B2

(12) United States Patent
Mebatsion et al.

(10) Patent No.: US 9,567,606 B2
(45) Date of Patent: Feb. 14, 2017

(54) RECOMBINANT POXVIRAL VECTORS EXPRESSING BOTH RABIES AND OX40 PROTEINS, AND VACCINES MADE THEREFROM

(71) Applicants: Teshome Mebatsion, Watkinsville, GA (US); Jules Maarten Minke, Corbas (FR); Frederic David, Watkinsville, GA (US)

(72) Inventors: Teshome Mebatsion, Watkinsville, GA (US); Jules Maarten Minke, Corbas (FR); Frederic David, Watkinsville, GA (US)

(73) Assignee: MERIAL INC., Duluth, GA (US)

( * ) Notice: Subject to any disclaimer, the term of this patent is extended or adjusted under 35 U.S.C. 154(b) by 152 days.

(21) Appl. No.: 13/767,603

(22) Filed: Feb. 14, 2013

(65) Prior Publication Data

US 2013/0209511 A1 Aug. 15, 2013

Related U.S. Application Data

(60) Provisional application No. 61/598,610, filed on Feb. 14, 2012.

(51) Int. Cl.

| | |
|---|---|
| *C12N 15/63* | (2006.01) |
| *C12N 15/86* | (2006.01) |
| *C12N 15/863* | (2006.01) |
| *A61K 39/008* | (2006.01) |
| *A61K 39/12* | (2006.01) |
| *A61K 39/39* | (2006.01) |
| *A61K 39/00* | (2006.01) |

(52) U.S. Cl.

CPC ............. *C12N 15/86* (2013.01); *A61K 39/008* (2013.01); *A61K 39/12* (2013.01); *A61K 39/39* (2013.01); *C12N 15/8633* (2013.01); *A61K 2039/53* (2013.01); *A61K 2039/552* (2013.01); *A61K 2039/55516* (2013.01); *C12N 2710/24043* (2013.01); *C12N 2760/20134* (2013.01)

(58) Field of Classification Search

None

See application file for complete search history.

(56) References Cited

U.S. PATENT DOCUMENTS

| | | | | |
|---|---|---|---|---|
| 5,756,103 A * | 5/1998 | Paoletti et al. | ............ | 424/199.1 |
| 6,309,647 B1 | 10/2001 | Pasteur | | |
| 2004/0071675 A1* | 4/2004 | Mazarakis et al. | ........ | 424/93.21 |

FOREIGN PATENT DOCUMENTS

| | | |
|---|---|---|
| CN | 101884793 | 6/2010 |

OTHER PUBLICATIONS

UniProt Accession No. E2RP79 for TNFSF4, 2010.*

Baker et al., Protein Structure Predication and Structural Genomics, Science (2001) vol. 294, No. 5540, pp. 93-96.*

Attwood, T. The Babel of Bioinformatics, Science (2000) vol. 290, No. 5491, pp. 471-473.*

Liu J et al. "CD4OL expressed from the canarypox vector, ALVAC, can boost immunogenicity of HIV-1 canarypox vaccine in mice and enhance the in vitro expansion of viral specific CD8+T cell memory responses from HIV-1-infected and HIV-1-uninfected individuals." Vaccine 26 (2008) 4062-4072.

Faber et al. "Overexpression of the Rabies Virus Glycoprotein Results in Enhancement of Apoptosis and Antiviral Immune Response." Journal of Virology, Apr. 2002, p. 3374-3381. vol. 76, No. 7.

Liu J et al. "The adjuvancy of OX40 ligand (CD252) on an HIV-1 canarypox vaccine." Vaccine 27 (2009) 5077-5084.

Serghides L et al. "Evaluation of OX40 Ligand as a Costimulator of Human Antiviral Memory CD8 T Cell Responses Comparison with B7.1 and 4-1BBL." J Immunol 2005;175;6368-6377.

* cited by examiner

*Primary Examiner* — Michelle S Horning

(74) *Attorney, Agent, or Firm* — Judy Jarecki-Black; Chad Kitchen; Merial Inc.

(57) ABSTRACT

The present invention provides vectors that contain and co-express in vivo or in vitro immunogenic polypeptides or antigens together with an OX40L polypeptide, which functions as a genetic adjuvant. Together, the immunogenic polypeptide and the OX40L polypeptide elicit an immune response in animal or human, which is greater than the immune response elicited by the immunogenic polypeptide alone. In a particular example, the invention provides vectors encoding a Rabies G immunogenic polypeptide and a canine OX40L genetic adjuvant, which vectors elicit strong immune responses in canine against rabies virus.

16 Claims, 32 Drawing Sheets

Lane 1. 1Kb marker
2. ALVAC Hind III
3. vCP3006 P5 Hind III
4. ALVAC BamHI
5. vCP3006 P5 BamHI
6. ALVAC XbaI
7. vCP3006 P5 XbaI
8. 1Kb marker Lane 1. 1Kb marker
2. ALVAC Hind III - 17367 bp
3. vCP3006 P5 Hind III
4. ALVAC BamHI
5. vCP3006 P5 BamHI - 14322 bp for left C3 site
   5248 for right C3 site
6. ALVAC XbaI
7. vCP3006 P5 XbaI
8. 1Kb marker Fragment of vCP3006

Fragment of vCP3006 Sequence Key (complete sequence is as set forth in SEQ ID NO:2):

1st UPPER CASE Text: C3 Right arm (SEQ ID NO:3)

1st lower case Text: I3L promoter (SEQ ID NO:4)

2nd UPPER CASE Text: Synthetic Rabies G (SEQ ID NO:5)

2nd lower case Text: C3 right arm (SEQ ID NO:6)

Underlined Text is cloning VECTOR sequence

```
GCTTTATGAAGAGGAGGATTTTTACATTTTAAAATATCGGCACCGTGTTCTAGTAATAATTTTA
CCATTTCTATATCAGAAATACTTACGGCTAAATACAAAGACGTTGATAGTATATTTACGTTATT
GTATTTGCATTTTTTAAGTATATACCTTACTAAATTTATATCTCTATACCTTATAGCTTTATGC
AGTTCATTTATAAGTCTTCCATTACTCATTTCTGGTAATGAAGTATTATATATCATTATGATAT
TATCTCTATTTTATTCTAATAAAAACCGTTATCATGTTATTTATTATTTGTTATAATTATACTA
TTTAATAAATTATACCAAATACTTAGATACTTATTAATACCATCCTAGAACTTGTATTTCTTGC
CCCCTAAACTTGGACATGCACTCCATTAGGCGTTTCTTGTTTTCGACATCGTCCTCCTTAACAT
ATCCTACTGTTATGTGAGGATTCCACGGATTATCTACTGTGATATCACCAAACACGTCCTTCGA
ACAGGGTACCGCATTCAGCAGAACATTTCTTAGGGCTCTAAGTTCATCAGATACCTCCAGTTTC
ATAACTACAGCGCATCCTTTCGCTCCCAACTGTTTAGAGGCGTTACTCTGAGGAAAACACATCT
CTTCTTTACAGACTATAGAAATAGTCTGTAAATCTTGATCAGTTATTTGCTTTTTGAAATTTTC
AAATCTATCACATTGATCCATATTTGCTATTCCAAGAGTTATATGAGGAAAAATATCACATCCT
GTCATGTATTTTATTGTAACATTATTATAATCTGTAACATCAGTATCTAACCTAACGTCGTAAA
AGTTAACAGATGCCCAGTTACTATAATCCCAAGGAACCTTAACATCTAATCCCATTAAAATAGT
ATCCTTTCTACTATTTTTTTCATTGGCAAGTATGTGGCTTAGTTTACACAAAATTCCTGCCATT
TTGTAACGATAGCGAAGCAATAGCTTGTATGCTTTTTATTTGATTAACTAGTCATAAAAATCGG
GATCCCTCGAGatgagataaagtgaaaatatatatcattatattacaaagtacaattatttagg
tttaatcATGGTGCCCCAGGCCCTGCTGTTCGTGCCCCTGCTGGTGTTCCCCCTGTGCTTCGGC
AAGTTCCCCATCTACACCATCCCCGACAAGCTGGGCCCCTGGAGCCCCATCGACATCCACCACC
TGAGCTGCCCCAACAATCTGGTGGTGGAGGATGAGGGCTGCACCAATCTGAGCGGCTTCAGCTA
CATGGAGCTGAAAGTGGGCTACATCCTGGCCATCAAGATGAACGGCTTCACCTGCACCGGCGTG
GTGACCGAGGCCGAGACCTACACCAACTTTGTGGGCTACGTGACCACCACCTTCAAGCGGAAGC
```

*FIG. 7*

ACTTCAGACCTACCCCCGACGCCTGCAGAGCCGCCTACAACTGGAAGATGGCCGGCGACCCTAG
ATACGAGGAGAGCCTGCACAACCCCTACCCCGACTACAGATGGCTGCGGACCGTGAAAACCACC
AAGGAGTCCCTGGTGATCATCAGCCCTAGCGTGGCCGATCTGGACCCCTACGACAGAAGCCTGC
ACAGCAGAGTGTTCCCTAGCGGCAAGTGCAGCGGCGTGGCCGTGTCCAGCACCTACTGCAGCAC
CAACCACGACTACACCATCTGGATGCCCGAGAACCCTAGACTGGGCATGAGCTGCGACATCTTC
ACCAACAGCCGGGGCAAGAGAGCCAGCAAGGGCAGCGAGACCTGCGGCTTCGTGGACGAGAGAG
GCCTGTACAAGAGCCTGAAGGGCGCCTGCAAGCTGAAGCTGTGCGGCGTGCTGGGCCTGAGACT
GATGGACGGCACCTGGGTGGCCATGCAGACCAGCAACGAGACCAAGTGGTGCCCTCCTGACCAG
CTGGTGAACCTGCACGACTTCCGGAGCGATGAGATCGAGCACCTGGTGGTGGAAGAGCTGGTGC
GGAAGAGAGAGGAGTGCCTGGACGCCCTGGAGAGCATCATGACCACCAAGAGCGTGTCCTTCCG
GAGACTGAGCCACCTGAGAAAGCTGGTGCCCGGCTTTGGCAAGGCCTACACAATCTTCAACAAG
ACCCTGATGGAGGCCGATGCCCACTACAAGTCTGTGCGGACCTGGAACGAGATCCTGCCTAGCA
AGGGCTGCCTGAGAGTGGGCGGCAGATGCCACCCCCACGTGAACGGCGTGTTCTTCAACGGCAT
CATCCTGGGCCCTGACGGCAACGTGCTGATCCCTGAGATGCAGAGCAGCCTGCTGCAGCAGCAC
ATGGAACTGCTGGAGAGCAGCGTGATCCCCCTGGTGCACCCCCTGGCCGACCCCAGCACCGTGT
TCAAGGATGGCGACGAGGCCGAGGACTTCGTGGAGGTGCACCTGCCCGATGTGCACAACCAGGT
GTCCGGCGTGGACCTGGGCCTGCCCAACTGGGGCAAGTACGTGCTGCTGAGCGCCGGAGCCCTG
ACCGCCCTGATGCTGATCATCTTCCTGATGACCTGCTGCCGGAGGGTGAACAGAAGCGAGCCCA
CCCAGCACAACCTGAGAGGCACCGGCAGAGAGGTGTCCGTGACCCCCAGAGCGGCAAGATCAT
CAGCAGCTGGGAGAGCCACAAGAGCGGCGGAGAGACCAGACTATGAttttatgcccgggtttt
tatagctaattagtcaaatgtgagttaatattagtatactacattactaatttattacatattc
atttatatcaatctagtagcatttagcttttataaaacaatataactgaatagtacatacttta
ctaataagttataaataagagatacatatttatagtattttactttctacactgaatataataa
tataattatacaaatataattttaatactatatagtatataactgaaataaaataccagtgta
atatagttattatacatttataccacatcaaagatgagttataacatcagtgtcactgttagca
acagtagttatacgatgagtagttactctcgtatggcgttagtatgtatgtatcttctagtttt
cttagtaggcattataggaaacgtcaagcttataaggttattaatggtatctagaaatatatct
attataccgtttctcaacttgggaatagccgatttgctgtttgtgatattcacctttataca
ttatatacatactaagtaatttccattggcattttggtaaagcactttgtaaaattagttcttt
cttttttacttctaacatgtttgcaagtatatttttaataactgtaataagcgtatatagatat

*FIG. 7 (Continued)*

```
gtaaaaattacccttcctggatttacctataaatatgttaacattagaaatatgtacattacta
tattttcatatggattatttctattatactagggattcctgctctttactttagaaatactat
cgtaacaaaaaataacgacacgctgtgtattaatcattatcatgataatagagaaattgctgaa
ttgatttacaaagttattatctgtatcagatttattttaggatacctactacctacgataatta
tactcgtatgctatacgttactgat
```

FIG. 7 (Continued)

Synthetic codon-optimized rabies virus glycoprotein G (SEQ ID NO:1)

```
  1    MVPQALLFVP  LLVFPLCFGK  FPIYTIPDKL  GPWSPIDIHH  LSCPNNLVVE
 51    DEGCTNLSGF  SYMELKVGYI  LAIKMNGFTC  TGVVTEAETY  TNFVGYVTTT
101    FKRKHFRPTP  DACRAAYNWK  MAGDPRYEES  LHNPYPDYRW  LRTVKTTKES
151    LVIISPSVAD  LDPYDRSLHS  RVFPSGKCSG  VAVSSTYCST  NHDYTIWMPE
201    NPRLGMSCDI  FTNSRGKRAS  KGSETCGFVD  ERGLYKSLKG  ACKLKLCGVL
251    GLRLMDGTWV  AMQTSNETKW  CPPDQLVNLH  DFRSDEIEHL  VVEELVRKRE
301    ECLDALESIM  TTKSVSFRRL  SHLRKLVPGF  GKAYTIFNKT  LMEADAHYKS
351    VRTWNEILPS  KGCLRVGGRC  HPHVNGVFFN  GIILGPDGNV  LIPEMQSSLL
401    QQHMELLESS  VIPLVHPLAD  PSTVFKDGDE  AEDFVEVHLP  DVHNQVSGVD
451    LGLPNWGKYV  LLSAGALTAL  MLIIFLMTCC  RRVNRSEPTQ  HNLRGTGREV
501    SVTPQSGKII  SSWESHKSGG  ETRL*
```

*FIG. 8*

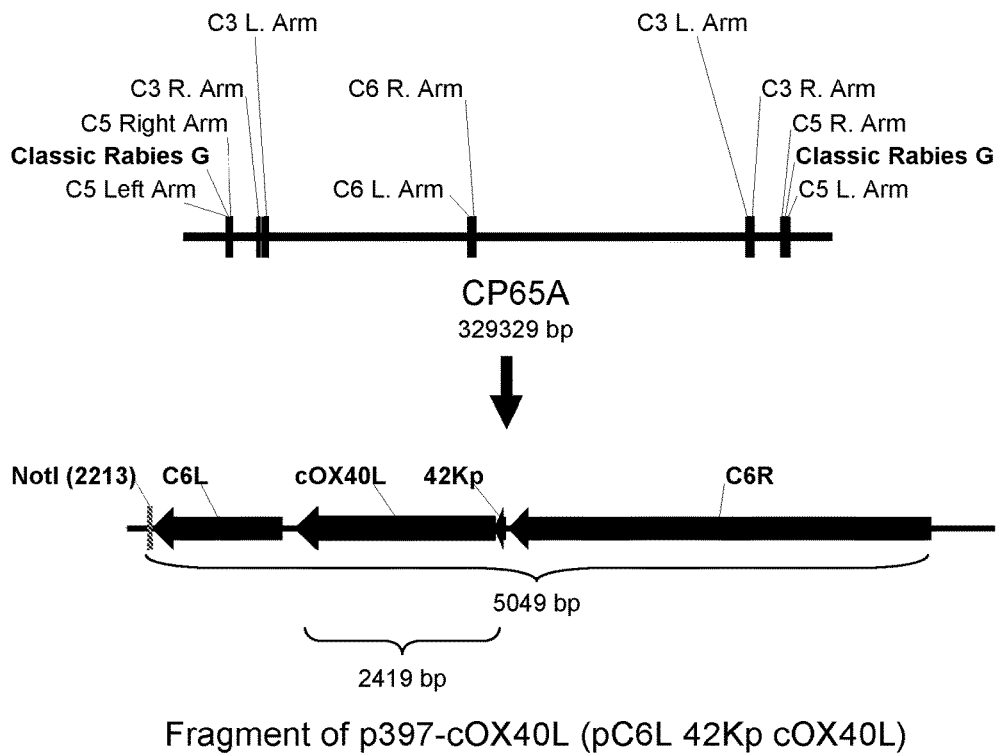
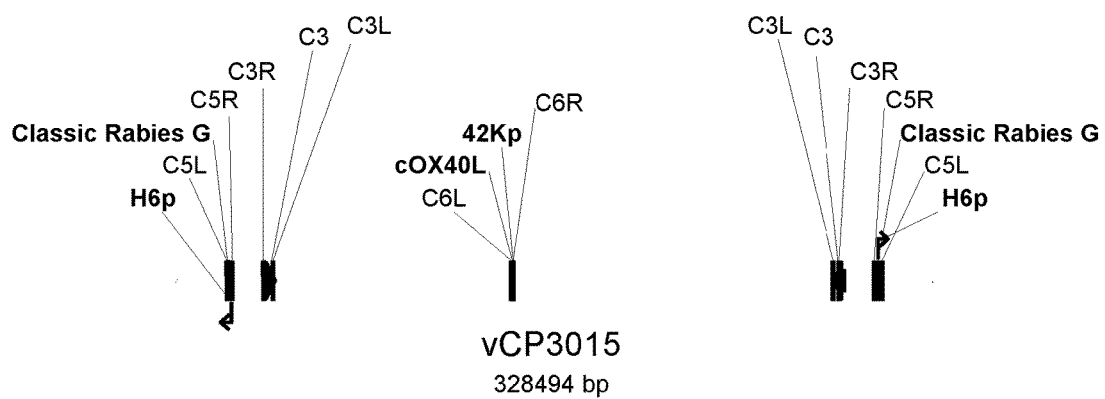
*FIG. 10*

Fragment of vCP3015

Fragment of vCP3015 C6R to C6L (SEQ ID NO:7) sequence key

C6R arm (1-1148): SEQ ID NO:8

42K promoter (1155-1186): SEQ ID NO:9 cOX40L (1187-1735): SEQ ID NO:10

C6L arm (1777-2141): SEQ ID NO:11

```
   1   GTTCTAAAGT TCTTTCCTCC GAAGGTATAG AACAAAGTAT TTCTTCTACA
  51   TCCTTACTAT TTATTGCAGC TTTTAACAGC CTATCACGTA TCCTATTTTT
 101   AGTATTGGTA GAACGTTTTA GTTCTAAAGT TAAAATATTA GACATAATTG
 151   GCATATTGCT TATTCCTTGC ATAGTTGAGT CTGTAGATCG TTTCAGTATA
 201   TCACTGATTA ATGTACTACT GTTATGATGA AATATAGAAT CGATATTGGC
 251   ATTTAACTGT TTTGTTATAC TAAGTCTAGA TTTTAAATCT TCTAGTAATA
 301   TGCTATTTAA TATAAAAGCT TCCACGTTTT TGTATACATT TCTTTCCATA
 351   TTAGTAGCTA CTACTAAATG ATTATCTTCT TTCATATCTT GTAGATAAGA
 401   TAGACTATCT TTATCTTTAT TAGTAGAAAA TACTTCTGGC CATACATCGT
 451   TAAATTTTTT TGTTGTTGTT AGATATAATA TTAAATATCT AGAGGATCCT
 501   ATTATTTGTG GTAAAATGTT TATAGAGTAA AATGATCTGG CTATTAAACA
 551   TAGGCCAGTT ACCATAGAAT GCTGCTTCCC GTTACAGTGT TTTACCATAA
 601   CCATAGATCT GCCTGTATTG TTGATACATA TAACAGCTGT AAATCCTAAA
 651   AAATTCCTAT CATAATTATT AATATTAGGT AATTCATTTC CATGTGAAAG
 701   ATAGACTAAT TTTATATCCT TTACCTCCAA ATAATTATTT ACATCTCTTA
 751   AACAATCTAT TTTAATATCA TTAACTGGTA TTTTATAATA TCCAGAAAGG
 801   TTTGAAGGGG TTGATGGAAT AAGTCTATTA ACATCGTTAA GTAAATTATT
 851   AATATCATGA ATCTTTATTA TATTATACCC ATAAGTTAAA TTTATATTTA
 901   CTTTCTCATC ATCTGACTTA GTTAGTTTGT AATAAGGTGT GTCTGAAAAA
 951   ATTAAAAGGT AATTCGTTGA ATGAAGCTGT ATTTGCTGTA TCATTTTTAT
1001   CTAATTTTGG AGATTAGCA GTACTTACTT CATTAGAAGA AGAATCTGCC
1051   AGTTCCTGTC TATTACTGAT ATTTCGTTTC ATTATTATAT GATTTATATT
```

*FIG. 15*

```
1101  TTACTTTTTC  AATTATATAT  ACTCATTTGA  CTAGTTAATC  AATAAAAAGA
1151  ATTCTCAAAA  TTGAAAATAT  ATAATTACAA  TATAAAATGG  AAGGAGTACA
1201  ACCATTAGAT  CAAATGTTG   GAAATACACC  AGGAAGAAGA  TTTCAAAAAA
1251  ATAAGTATT   ATTAGTAGCA  GCAATAATTC  AAGGTTTAGG  ATTATTATTA
1301  TGTTTTACAT  ATATATGTTT  ACACTTTTAT  GCATCTCAAG  TACCACCTCA
1351  ATATCCACCT  ATACAAAGTA  TAAGAGTTCA  GTTTACAAGA  TGTGAAAATG
1401  AAAAGGTTG   TATTATTACA  TCTCCAAGTA  AAGATGAAAC  TATGAAAGTA
1451  CAAGATAATT  CAATAATCAT  AAATTGTGAT  GGTTTTTACT  TAATTAGTTT
1501  AAAAGGATAT  TTTTCAGAAG  AATTATCATT  ATCTTTATAT  TATAGAAAAG
1551  GTAGAGGACC  TTTATTTTCT  TTATCAAAAG  TAACATCAGT  TGATTCTATT
1601  GGAGTTGCAT  ATTTGGCTTT  TAAAGATAAA  GTATATTTTA  ATGTTACAAC
1651  TCATTCTACT  AGTTATAAAG  ATATACAAGT  AAATGGTGGT  GAATTAATAT
1701  TAATACATCA  AAATCCTGGT  GGATTTGTG   CTTATTAATT  TTTATCCCGG
1751  GTTTTTATAG  CTAATTAGTC  ATTTTCGTA   AGTAAGTATT  TTTATTTAAT
1801  ACTTTTTATT  GTACTTATGT  TAAATATAAC  TGATGATAAC  AAAATCCATT
1851  ATGTATTATT  TATAACTGTA  ATTTCTTTAG  CGTAGTTAGA  TGTCCAATCT
1901  CTCTCAAATA  CATCGGCTAT  CTTTTAGTG   AGATTTTGAT  CTATGCAGTT
1951  GAAACTTATG  AACGCGTGAT  GATTAAAATG  TGAACCGTCC  AAATTTGCAG
2001  TCATTATATG  AGCGTATCTA  TTATCTACTA  TCATCATCTT  TGAGTTATTA
2051  ATATCATCTA  CTTTAGAATT  GATAGGAAAT  ATGAATACCT  TTGTAGTAAT
2101  ATCTATACTA  TCTACACCTA  ACTCATTAAG  ACTTTTGATA  G
```

*FIG. 15 (Continued)*

Predicted amino acid sequence of synthetic cOX40L (SEQ ID NO:12)

```
  1   MEGVQPLDQN VGNTPGRRFQ KNKVLLVAAI IQGLGLLLCF TYICLHFYAS
 51   QVPPQYPPIQ SIRVQFTRCE NEKGCIITSP SKDETMKVQD NSIIINCDGF
101   YLISLKGYFS EELSLSLYYR KGRGPLFSLS KVTSVDSIGV AYLAFKDKVY
151   FNVTTHSTSY KDIQVNGGEL ILIHQNPGGF CAY
```

Fragment of vCP3015

<u>C5 Right arm to Classic Rabies G:SEQ ID NO:13</u>

1st UPPER CASE Text: C5 right arm: SEQ ID NO:14 lower case Text: H6 promoter: SEQ ID NO:15

2nd UPPER CASE Text: Classic Rabies G: SEQ ID NO:16

<u>Underlined Text: Vector Sequence</u>

GCTATAAATATGCATTGGAAAAATAATCCATTTAAAGAAAGGATTCAAATACTACAAAACCTAAGCGATA
ATATGTTAACTAAGCTTATTCTTAACGACGCTTTAAATATACACAAATAAACATAATTTTTGTATAACCT
AACAAATAACTAAAACATAAAAATAATAAAAGGAAATGTAATATCGTAATTATTTTACTCAGGAATGGGG
TTAAATATTTATATCACGTGTATATCTATACTGTTATCGTATACTCTTTACAATTACTATTACGAATATG
CAAGAGATAATAAGATTACGTATTTAAGAGAATCTTGTCATGATAATTGGGTACGACATAGTGATAAATG
CTATTTCGCATCGTTACATAAAGTCAGTTGGAAAGATGGATTTGACAGATGTAACTTAATAGGTGCAAAA
ATGTTAAATAACAGCATTCTATCGGAAGATAGGATACCAGTTATATTATACAAAAATCACTGGTTGGATA
AAACAGATTCTGCAATATTCGTAAAAGATGAAGATTACTGCGAATTTGTAAACTATGACAATAAAAAGCC
ATTTATCTCAACGACATCGTGTAATTCTTCCATGTTTTATGTATGTGTTTCAGATATTATGAGATTACTA
TAAACTTTTTGTATACTTATATTCCGTAAACTATATTAATCATGAAGAAAATGAAAAAGTATAGAAGCTG
TTCACGAGCGGTTGTTGAAAACAACAAAATTATACATTCAAGATGGCTTACATATACGTCTGTGAGGCTA
TCATGGATAATGACAATGCATCTCTAAATAGGTTTTTGGACAATGGATTCGACCCTAACACGGAATATGG
TACTCTACAATCTCCTCTTGAAATGGCTGTAATGTTCAAGAATACCGAGGCTATAAAAATCTTGATGAGG
TATGGAGCTAAACCTGTAGTTACTGAATGCACAACTTCTTGTCTGCATGATGCGGTGTTGAGAGACGACT
ACAAAATAGTGAAAGATCTGTTGAAGAATAACTATGTAAACAATGTTCTTTACAGCGGAGGCTTTACTCC
TTTGTGTTTGGCAGCTTACCTTAACAAAGTTAATTTGGTTAAACTTCTATTGGCTCATTCGGCGGATGTA
GATATTTCAAACACGGATCGGTTAACTCCTCTACATATAGCCGTATCAAATAAAAATTTAACAATGGTTA
AACTTCTATTGAACAAAGGTGCTGATACTGACTTGCTGGATAACATGGGACGTACTCCTTTAATGATCGC
TGTACAATCTGGAAATATTGAAATATGTAGCACACTACTTAAAAAAAATAAAATGTCCAGAACTGGGAAA
AATTGATCTTGCCAGCTGTAATTCATGGTAGAAAAGAAGTGCTCAGGCTACTTTTCAACAAAGGAGCAGA
TGTAAACTACATCTTTGAAAGAAATGGAAAATCATATACTGTTTTGGAATTGATTAAAGAAAGTTACTCT
GAGACACAAAAGAGGTAGCTGAAGTGGTACTCTCAAAA<u>GCTTCCCGGGTTAATTAATTAGTTATTAGACA</u>
<u>AGGTGAAAACGAAACTATTTGTAGCTTAATTAATTAGAGC</u>ttctttattctatacttaaaaagtgaaaat
aaatacaaaggttcttgagggttgtgttaaattgaaagcgagaaataatcataaattatttcattatcgc
gatatccgttaagtttgtatcgtaATGGTTCCTCAAGCTCTCCTGTTTGTACCCCTTCTGGTTTTTCCGT

*FIG. 18*

```
TGTGTTTTGGAAAATTCCCTATTTACACAATCCCAGACAAGCTTGGTCCCTGGAGCCCGATTGACATACA
TCACCTCAGCTGCCCAAACAATTTGGTAGTGGAGGACGAAGGATGCACCAACCTGTCAGGGTTCTCCTAC
ATGGAACTTAAAGTTGGATACATCTTAGCCATAAAAATGAACGGGTTCACTTGCACAGGCGTTGTGACGG
AGGCTGAAACCTACACTAACTTCGTTGGTTATGTCACAACCACGTTCAAAAGAAAGCATTTCCGCCCAAC
ACCAGATGCATGTAGAGCCGCGTACAACTGGAAGATGGCCGGTGACCCCAGATATGAAGAGTCTCTACAC
AATCCGTACCCTGACTACCGCTGGCTTCGAACTGTAAAAACCACCAAGGAGTCTCTCGTTATCATATCTC
CAAGTGTAGCAGATTTGGACCCATATGACAGATCCCTTCACTCGAGGGTCTTCCCTAGCGGGAAGTGCTC
AGGAGTAGCGGTGTCTTCTACCTACTGCTCCACTAACCACGATTACACCATTTGGATGCCCGAGAATCCG
AGACTAGGGATGTCTTGTGACATTTTTACCAATAGTAGAGGGAAGAGAGCATCCAAAGGGAGTGAGACTT
GCGGCTTTGTAGATGAAAGAGGCCTATATAAGTCTTTAAAAGGAGCATGCAAACTCAAGTTATGTGGAGT
TCTAGGACTTAGACTTATGGATGGAACATGGGTCGCGATGCAAACATCAAATGAAACCAAATGGTGCCCT
CCCGATCAGTTGGTGAACCTGCACGACTTTCGCTCAGACGAAATTGAGCACCTTGTTGTAGAGGAGTTGG
TCAGGAAGAGAGAGGAGTGTCTGGATGCACTAGAGTCCATCATGACAACCAAGTCAGTGAGTTTCAGACG
TCTCAGTCATTTAAGAAAACTTGTCCCTGGGTTTGGAAAAGCATATACCATATTCAACAAGACCTTGATG
GAAGCCGATGCTCACTACAAGTCAGTCAGAACTTGGAATGAGATCCTCCCTTCAAAAGGGTGTTTAAGAG
TTGGGGGGAGGTGTCATCCTCATGTGAACGGGGTGTTTTTCAATGGTATAATATTAGGACCTGACGGCAA
TGTCTTAATCCCAGAGATGCAATCATCCCTCCTCCAGCAACATATGGAGTTGTTGGAATCCTCGGTTATC
CCCCTTGTGCACCCCTGGCAGACCCGTCTACCGTTTTCAAGGACGGTGACGAGGCTGAGGATTTTGTTG
AAGTTCACCTTCCCGATGTGCACAATCAGGTCTCAGGAGTTGACTTGGGTCTCCCGAACTGGGGGAAGTA
TGTATTACTGAGTGCAGGGGCCCTGACTGCCTTGATGTTGATAATTTTCCTGATGACATGTTGTAGAAGA
GTCAATCGATCAGAACCTACGCAACACAATCTCAGAGGGACAGGGAGGGAGGTGTCAGTCACTCCCCAAA
GCGGGAAGATCATATCTTCATGGGAATCACACAAGAGTGGGGGTGAGACCAGACTGTGA
```

FIG. 18 (Continued)

Predicted amino acid sequence of classical rabies virus G (SEQ ID NO:1)

```
  1    MVPQALLFVP LLVFPLCFGK FPIYTIPDKL GPWSPIDIHH LSCPNNLVVE
 51    DEGCTNLSGF SYMELKVGYI LAIKMNGFTC TGVVTEAETY TNFVGYVTTT
101    FKRKHFRPTP DACRAAYNWK MAGDPRYEES LHNPYPDYRW LRTVKTTKES
151    LVIISPSVAD LDPYDRSLHS RVFPSGKCSG VAVSSTYCST NHDYTIWMPE
201    NPRLGMSCDI FTNSRGKRAS KGSETCGFVD ERGLYKSLKG ACKLKLCGVL
251    GLRLMDGTWV AMQTSNETKW CPPDQLVNLH DFRSDEIEHL VVEELVRKRE
301    ECLDALESIM TTKSVSFRRL SHLRKLVPGF GKAYTIFNKT LMEADAHYKS
351    VRTWNEILPS KGCLRVGGRC HPHVNGVFFN GIILGPDGNV LIPEMQSSLL
401    QQHMELLESS VIPLVHPLAD PSTVFKDGDE AEDFVEVHLP DVHNQVSGVD
451    LGLPNWGKYV LLSAGALTAL MLIIFLMTCC RRVNRSEPTQ HNLRGTGREV
501    SVTPQSGKII SSWESHKSGG ETRL*
```

*FIG. 19* vCP3012 C6 Right arm to C6 Left arm: SEQ ID NO:17
1st UPPER CASE=C6R arm (SEQ 18); 2nd UC=cOX40L (SEQ 10)
1st lower case=42K (SEQ 9); 2nd LC=C6L arm (SEQ 19); Vector=underlined GTTCTAAAGTTCTTTCCTCCGAAGGTATAGAACAAAGTATTTCTTCTACATCCTTACTATTTATTGCAGC
TTTTAACAGCCTATCACGTATCCTATTTTTAGTATTGGTAGAACGTTTTAGTTCTAAAGTTAAAATATTA
GACATAATTGGCATATTGCTTATTCCTTGCATAGTTGAGTCTGTAGATCGTTTCAGTATATCACTGATTA
ATGTACTACTGTTATGATGAAATATAGAATCGATATTGGCATTTAACTGTTTTGTTATACTAAGTCTAGA
TTTTAAATCTTCTAGTAATATGCTATTTAATATAAAAGCTTCCACGTTTTTGTATACATTTCTTTCCATA
TTAGTAGCTACTACTAAATGATTATCTTCTTTCATATCTTGTAGATAAGATAGACTATCTTTATCTTTAT
TAGTAGAAAATACTTCTGGCCATACATCGTTAAATTTTTTGTTGTTGTTAGATATAATATTAAATATCT
AGAGGATCCTATTATTTGTGGTAAAATGTTTATAGAGTAAAATGATCTGGCTATTAAACATAGGCCAGTT
ACCATAGAATGCTGCTTCCCGTTACAGTGTTTTACCATAACCATAGATCTGCCTGTATTGTTGATACATA
TAACAGCTGTAAATCCTAAAAAATTCCTATCATAATTATTAATATTAGGTAATTCATTTCCATGTGAAAG
ATAGACTAATTTTATATCCTTTACCTCCAAATAATTATTTACATCTCTTAAACAATCTATTTTAATATCA
TTAACTGGTATTTTATAATATCCAGAAAGGTTTGAAGGGGTTGATGGAATAAGTCTATTAACATCGTTAA
GTAAATTATTAATATCATGAATCTTTATTATATTATACCCATAAGTTAAATTTATATTTACTTTCTCATC
ATCTGACTTAGTTAGTTTGTAATAAGGTGTGTCTGAAAAAATTAAAAGGTAATTCGTTGAATGAAGCTGT
ATTTGCTGTATCATTTTTATCTAATTTTGGAGATTTAGCAGTACTTACTTCATTAGAAGAAGAATCTGCC
AGTTCCTGTCTATTACTGATATTTCGTTTCATTATTATATGATTTATATTTTACTTTTTCAATTATATAT
ACTCATTTGACTAGTTAATCAATAAAAA<u>GAATTC</u>tcaaaattgaaaatatataattacaatataaaATGG
AAGGAGTACAACCATTAGATCAAAATGTTGGAAATACACCAGGAAGAAGATTTCAAAAAAATAAAGTATT
ATTAGTAGCAGCAATAATTCAAGGTTTAGGATTATTATTATGTTTTACATATATATGTTTACACTTTTAT
GCATCTCAAGTACCACCTCAATATCCACCTATACAAAGTATAAGAGTTCAGTTTACAAGATGTGAAAATG
AAAAAGGTTGTATTATTACATCTCCAAGTAAAGATGAAACTATGAAAGTACAAGATAATTCAATAATCAT
AAATTGTGATGGTTTTTACTTAATTAGTTTAAAAGGATATTTTTCAGAAGAATTATCATTATCTTTATAT
TATAGAAAAGGTAGAGGACCTTTATTTTCTTTATCAAAAGTAACATCAGTTGATTCTATTGGAGTTGCAT
ATTTGGCTTTTAAAGATAAAGTATATTTTAATGTTACAACTCATTCTACTAGTTATAAAGATATACAAGT
AAATGGTGGTGAATTAATATTAATACATCAAAATCCTGGTGGATTTTGTGCTTATTAA<u>TTTTTATCCCGG
GTTTTTATAGCTAATTAGTCATTTTT</u>cgtaagtaagtatttttatttaatacttttattgtacttatgt
taaatataactgatgataacaaaatccattatgtattatttataactgtaatttctttagcgtagttaga
tgtccaatctctctcaaatacatcggctatcttttagtgagattttgatctatgcagttgaaacttatg
aacgcgtgatgattaaaatgtgaaccgtccaaatttgcagtcattatatgagcgtatctattatctacta
tcatcatctttgagttattaatatcatctactttagaattgataggaaatatgaataccttttgtagtaat
atctatactatctacacctaactcattaagacttttgatag  *FIG. 26*

Fragment of vCP3012 showing synthetic rabies virus G and flanking regions (5900 bp of 329138 bp)

*FIG. 27*

Fragment of vCP3012 containing C3R arm to C3L arm (SEQ ID NO:20)

1st UPPER CASE Text: C3R arm (SEQ ID NO:21)

*1st lower case Text: I3L promoter (SEQ ID NO:4)*

2nd BLACK Text: Synthetic Rabies G (SEQ ID NO:5)

*2nd lower case Text: C3R arm (SEQ ID NO:22)*

TGTAATGGGGTTTTACCTAAATCATCTTGTTCGTTTATAGGCACTCCGTGATTTATAAGTAACGCTATTA
TATCGTAACTACAATTATTTTTAAGTGCCTTTATGAGATACTGTTTATGCAAAAATAAACTTTTATCTAT
TTTAATACTATTATCTAACAATATCCTAATTAAATCTATATTCTTATACTTTATAGCGTAATGTAACGGA
GTTTCAAAATTTCTAGTTTGTATATTAAGATCAATATTAAAATCTATAAATATTTTATACATATCATCAG
ATATCTTATCATACAGTACATCGTAATAATTTAGAAAGAATCTATTACAATTAACACCTTTTTTTAATAA
ATATCTAGTTAATGACTTATTGTTTCTATATACAGAAATATATAACGGACTATTTCCAGAATGTATCTGT
TCTATGTCAGCGCCAGAATCTATTAGTAGTTTAGCAATTTCTGTATTATCTAAACTAGCAGCTTTATGAA
GAGGAGGATTTTTACATTTTAAAATATCGGCACCGTGTTCTAGTAATAATTTTACCATTTCTATATCAGA
AATACTTACGGCTAAATACAAAGACGTTGATAGTATATTTACGTTATTGTATTTGCATTTTTTAAGTATA
TACCTTACTAAATTTATATCTCTATACCTTATAGCTTTATGCAGTTCATTTATAAGTCTTCCATTACTCA
TTTCTGGTAATGAAGTATTATATATCATTATGATATTATCTCTATTTTATTCTAATAAAAACCGTTATCA
TGTTATTTATTATTTGTTATAATTATACTATTTAATAAATTATACCAAATACTTAGATACTTATTAATAC
CATCCTAGAACTTGTATTTCTTGCCCCCTAAACTTGGACATGCACTCCATTAGGCGTTTCTTGTTTTCGA
CATCGTCCTCCTTAACATATCCTACTGTTATGTGAGGATTCCACGGATTATCTACTGTGATATCACCAAA
CACGTCCTTCGAACAGGGTACCGCATTCAGCAGAACATTTCTTAGGGCTCTAAGTTCATCAGATACCTCC
AGTTTCATAACTACAGCGCATCCTTTCGCTCCCAACTGTTTAGAGGCGTTACTCTGAGGAAAACACATCT
CTTCTTTACAGACTATAGAAATAGTCTGTAAATCTTGATCAGTTATTTGCTTTTTGAAATTTTCAAATCT
ATCACATTGATCCATATTTGCTATTCCAAGAGTTATATGAGGAAAAATATCACATCCTGTCATGTATTTT
ATTGTAACATTATTATAATCTGTAACATCAGTATCTAACCTAACGTCGTAAAAGTTAACAGATGCCCAGT
TACTATAATCCCAAGGAACCTTAACATCTAATCCCATTAAAATAGTATCCTTTCTACTATTTTTTTCATT
GGCAAGTATGTGGCTTAGTTTACACAAAATTCCTGCCATTTTGTAACGATAGCGAAGCAATAGCTTGTAT
GCTTTTTATTTGATTAACTAGTCATAAAAATCGGGATCCCTCGAGatgagataaagtgaaaatatatatc
attatattacaaagtacaattatttaggtttaatcATGGTGCCCCAGGCCCTGCTGTTCGTGCCCCTGCT
GGTGTTCCCCCTGTGCTTCGGCAAGTTCCCCATCTACACCATCCCCGACAAGCTGGGCCCCTGGAGCCCC
ATCGACATCCACCACCTGAGCTGCCCCAACAATCTGGTGGTGGAGGATGAGGGCTGCACCAATCTGAGCG
GCTTCAGCTACATGGAGCTGAAAGTGGGCTACATCCTGGCCATCAAGATGAACGGCTTCACCTGCACCGG
CGTGGTGACCGAGGCCGAGACCTACACCAACTTTGTGGGCTACGTGACCACCACCTTCAAGCGGAAGCAC

*FIG. 28*

```
TTCAGACCTACCCCCGACGCCTGCAGAGCCGCCTACAACTGGAAGATGGCCGGCGACCCTAGATACGAGG
AGAGCCTGCACAACCCCTACCCCGACTACAGATGGCTGCGGACCGTGAAAACCACCAAGGAGTCCCTGGT
GATCATCAGCCCTAGCGTGGCCGATCTGGACCCCTACGACAGAAGCCTGCACAGCAGAGTGTTCCCTAGC
GGCAAGTGCAGCGGCGTGGCCGTGTCCAGCACCTACTGCAGCACCAACCACGACTACACCATCTGGATGC
CCGAGAACCCTAGACTGGGCATGAGCTGCGACATCTTCACCAACAGCCGGGGCAAGAGAGCCAGCAAGGG
CAGCGAGACCTGCGGCTTCGTGGACGAGAGAGGCCTGTACAAGAGCCTGAAGGGCGCCTGCAAGCTGAAG
CTGTGCGGCGTGCTGGGCCTGAGACTGATGGACGGCACCTGGGTGGCCATGCAGACCAGCAACGAGACCA
AGTGGTGCCCTCCTGACCAGCTGGTGAACCTGCACGACTTCCGGAGCGATGAGATCGAGCACCTGGTGGT
GGAAGAGCTGGTGCGGAAGAGAGAGGAGTGCCTGGACGCCCTGGAGAGCATCATGACCACCAAGAGCGTG
TCCTTCCGGAGACTGAGCCACCTGAGAAAGCTGGTGCCCGGCTTTGGCAAGGCCTACACAATCTTCAACA
AGACCCTGATGGAGGCCGATGCCCACTACAAGTCTGTGCGGACCTGGAACGAGATCCTGCCTAGCAAGGG
CTGCCTGAGAGTGGGCGGCAGATGCCACCCCCACGTGAACGGCGTGTTCTTCAACGGCATCATCCTGGGC
CCTGACGGCAACGTGCTGATCCCTGAGATGCAGAGCAGCCTGCTGCAGCAGCACATGGAACTGCTGGAGA
GCAGCGTGATCCCCCTGGTGCACCCCCTGGCCGACCCCAGCACCGTGTTCAAGGATGGCGACGAGGCCGA
GGACTTCGTGGAGGTGCACCTGCCCGATGTGCACAACCAGGTGTCCGGCGTGGACCTGGGCCTGCCCAAC
TGGGGCAAGTACGTGCTGCTGAGCGCCGGAGCCCTGACCGCCCTGATGCTGATCATCTTCCTGATGACCT
GCTGCCGGAGGGTGAACAGAAGCGAGCCCACCCAGCACAACCTGAGAGGCACCGGCAGAGAGGTGTCCGT
GACCCCCAGAGCGGCAAGATCATCAGCAGCTGGGAGAGCCACAAGAGCGGCGGAGAGACCAGACTATGA
TTTTTATGCCCGGGTTTTTATAGCTAATTAGTcaaatgtgagttaatattagtatactacattactaatt
tattacatattcatttatatcaatctagtagcatttagcttttataaaacaatataactgaatagtacat
actttactaataagttataaataagagatacatatttatagtattttactttctacactgaatataataa
tataattatacaaatataattttaatactatatagtatataactgaaataaaataccagtgtaatatag
ttattatacatttataccacatcaaagatgagttataacatcagtgtcactgttagcaacagtagttata
cgatgagtagttactctcgtatggcgttagtatgtatgtatcttctagttttcttagtaggcattatagg
aaacgtcaagcttataaggttattaatggtatctagaaatatatctattataccgtttctcaacttggga
atagccgatttgctgtttgtgatattcatacctttatacattatatacactaagtaatttccattggc
attttggtaaagcactttgtaaaattagttctttcttttttacttctaacatgtttgcaagtatatttt
aataactgtaataagcgtatatagatatgtaaaattacccttcctggatttacctataaatatgttaac
attagaaatatgtacattactatatttttcatatggattatttctattatactagggattcctgctcttt
actttagaaatactatcgtaacaaaaaataacgacacgctgtgtattaatcattatcatgataatagaga
aattgctgaattgatttacaaagttattatctgtatcagatttattttaggatacctactacctacgata
attatactcgtatgctatacgttactgat
```

Fragment of vCP3012 - rabies virus G and flanking regions
4191 bp (of 329138)

FIG. 29

Fragment of vCP3012 - rabies virus G and flanking regions (SEQ ID NO:23)
1st UPPER CASE Text: C5R arm (SEQ ID NO:24)
*lower case Text: H6 promoter (SEQ ID NO:15)*
2nd UPPER CASE Text: Classic Rabies G (SEQ ID NO:16)
<u>Underlined Text: vector sequence</u>

GCTATAAATATGCATTGGAAAAATAATCCATTTAAAGAAAGGATTCAAATACTACAAAACCTAAGCGATAATATGTT
AACTAAGCTTATTCTTAACGACGCTTTAAATATACACAAATAAACATAATTTTTGTATAACCTAACAAATAACTAAA
ACATAAAAATAATAAAAGGAAATGTAATATCGTAATTATTTTACTCAGGAATGGGGTTAAATATTTATATCACGTGT
ATATCTATACTGTTATCGTATACTCTTTACAATTACTATTACGAATATGCAAGAGATAATAAGATTACGTATTTAAG
AGAATCTTGTCATGATAATTGGGTACGACATAGTGATAAATGCTATTTCGCATCGTTACATAAAGTCAGTTGGAAAG
ATGGATTTGACAGATGTAACTTAATAGGTGCAAAAATGTTAAATAACAGCATTCTATCGGAAGATAGGATACCAGTT
ATATTATACAAAAATCACTGGTTGGATAAAACAGATTCTGCAATATTCGTAAAAGATGAAGATTACTGCGAATTTGT
AAACTATGACAATAAAAAGCCATTTATCTCAACGACATCGTGTAATTCTTCCATGTTTTATGTATGTGTTTCAGATA
TTATGAGATTACTATAAACTTTTTGTATACTTATATTCCGTAAACTATATTAATCATGAAGAAAATGAAAAAGTATA
GAAGCTGTTCACGAGCGGTTGTTGAAAACAACAAAATTATACATTCAAGATGGCTTACATATACGTCTGTGAGGCTA
TCATGGATAATGACAATGCATCTCTAAATAGGTTTTTGGACAATGGATTCGACCCTAACACGGAATATGGTA
CTCTACAATCTCCTCTTGAAATGGCTGTAATGTTCAAGAATACCGAGGCTATAAAAATCTTGATGAGGTA
TGGAGCTAAACCTGTAGTTACTGAATGCACAACTTCTTGTCTGCATGATGCGGTGTTGAGAGACGACTAC
AAAATAGTGAAAGATCTGTTGAAGAATAACTATGTAAACAATGTTCTTTACAGCGGAGGCTTTACTCCTT
TGTGTTTGGCAGCTTACCTTAACAAAGTTAATTTGGTTAAACTTCTATTGGCTCATTCGGCGGATGTAGA
TATTTCAAACACGGATCGGTTAACTCCTCTACATATAGCCGTATCAAATAAAAATTTAACAATGGTTAAA
CTTCTATTGAACAAAGGTGCTGATACTGACTTGCTGGATAACATGGGACGTACTCCTTTAATGATCGCTG
TACAATCTGGAAATATTGAAATATGTAGCACACTACTTAAAAAAAATAAAATGTCCAGAACTGGGAAAAA
TTGATCTTGCCAGCTGTAATTCATGGTAGAAAAGAAGTGCTCAGGCTACTTTTCAACAAAGGAGCAGATG
TAAACTACATCTTTGAAAGAAATGGAAAATCATATACTGTTTTGGAATTGATTAAAGAAAGTTACTCTGA
GACACAAAAGAGGTAGCTGAAGTGGTACTCTCAAAAG<u>CTTCCCGGGTTAATTAATTAGTTATTAGACAAG
GTGAAAACGAAACTATTTGTAGCTTAATTAATTAGAGC</u>*ttctttattctatacttaaaaagtgaaaataa
atacaaaggttcttgagggttgtgttaaattgaaagcgagaaataatcataaattatttcattatcgcga
tatccgttaagtttgtatcgta*ATGGTTCCTCAAGCTCTCCTGTTTGTACCCCTTCTGGTTTTTCCGTTG
TGTTTTGGAAAATTCCCTATTTACACAATCCCAGACAAGCTTGGTCCCTGGAGCCCGATTGACATACATC
ACCTCAGCTGCCCAAACAATTTGGTAGTGGAGGACGAAGGATGCACCAACCTGTCAGGGTTCTCCTACATGG
AACTTAAAGTTGGATACATCTTAGCCATAAAAATGAACGGGTTCACTTGCACAGGCGTTGTGACGGAGGCTGAAACC

*FIG. 30*

```
TACACTAACTTCGTTGGTTATGTCACAACCACGTTCAAAAGAAAGCATTTCCGCCCAACACCAGATGCATGTAGAGC
CGCGTACAACTGGAAGATGGCCGGTGACCCCAGATATGAAGAGTCTCTACACAATCCGTACCCTGACTACCGCTGGC
TTCGAACTGTAAAAACCACCAAGGAGTCTCTCGTTATCATATCTCCAAGTGTAGCAGATTTGGACCCATATGACAGA
TCCCTTCACTCGAGGGTCTTCCCTAGCGGGAAGTGCTCAGGAGTAGCGGTGTCTTCTACCTACTGCTCCACTAACCA
CGATTACACCATTTGGATGCCCGAGAATCCGAGACTAGGGATGTCTTGTGACATTTTTACCAATAGTAGAGGGAAGA
GAGCATCCAAAGGGAGTGAGACTTGCGGCTTTGTAGATGAAAGAGGCCTATATAAGTCTTTAAAAGGAGCATGCAAA
CTCAAGTTATGTGGAGTTCTAGGACTTAGACTTATGGATGGAACATGGGTCGCGATGCAAACATCAAATGAAACCAA
ATGGTGCCCTCCCGATCAGTTGGTGAACCTGCACGACTTTCGCTCAGACGAAATTGAGCACCTTGTTGTAGAGGAGT
TGGTCAGGAAGAGAGAGGAGTGTCTGGATGCACTAGAGTCCATCATGACAACCAAGTCAGTGAGTTTCAGACGTCTC
AGTCATTTAAGAAAACTTGTCCCTGGGTTTGGAAAAGCATATACCATATTCAACAAGACCTTGATGGAAGCCGATGC
TCACTACAAGTCAGTCAGAACTTGGAATGAGATCCTCCCTTCAAAAGGGTGTTTAAGAGTTGGGGGGAGGTGTCATC
CTCATGTGAACGGGGTGTTTTTCAATGGTATAATATTAGGACCTGACGGCAATGTCTTAATCCCAGAGATGCAATCA
TCCCTCCTCCAGCAACATATGGAGTTGTTGGAATCCTCGGTTATCCCCCTTGTGCACCCCCTGGCAGACCCGTCTAC
CGTTTTCAAGGACGGTGACGAGGCTGAGGATTTTGTTGAAGTTCACCTTCCCGATGTGCACAATCAGGTCTCAGGAG
TTGACTTGGGTCTCCCGAACTGGGGGAAGTATGTATTACTGAGTGCAGGGGCCCTGACTGCCTTGATGTTGATAATT
TTCCTGATGACATGTTGTAGAAGAGTCAATCGATCAGAACCTACGCAACACAATCTCAGAGGGACAGGGAGGGAGGT
GTCAGTCACTCCCCAAAGCGGGAAGATCATATCTTCATGGGAATCACACAAGAGTGGGGGTGAGACCAGACTGTGA
```

FIG. 30 (Continued)

Non-primer sequences disclosed in this application

| SEQ ID NO | DNA/ PRT | Sequence Description |
|---|---|---|
| 1 | PRT | Predicted Rabies G AA sequence (for both wild type and synthetic codon-optimized) |
| 2 | DNA | Subsequence of recombinant vCP3006 covering the flanking C3 arms, the I3L promoter as well as the synthetic rabies G |
| 3 | DNA | vCP3006 C3L arm |
| 4 | DNA | vCP3006 I3L promoter |
| 5 | DNA | vCP3006 synthetic rabies G |
| 6 | DNA | vCP3006 C3R arm |
| 7 | DNA | Fragment of vCP3015 containing C6R arm to C6L arm |
| 8 | DNA | vCP3015 C6R arm |
| 9 | DNA | vCP3015 42K promoter |
| 10 | DNA | vCP3015 cOX40L |
| 11 | DNA | vCP3015 C6L arm |
| 12 | PRT | cOX40L predicted AA sequence |
| 13 | DNA | Fragment of vCP3015 containing C5R arm to Classic Rabies G |
| 14 | DNA | vCP3015 C5R arm |
| 15 | DNA | vCP3015 H6 promoter |
| 16 | DNA | Classic rabies G gene (wild type) |
| 17 | DNA | vCP3012 C6R arm to C6L arm |
| 18 | DNA | vCP3012 C6R arm |
| 19 | DNA | vCP3012 C6L arm |
| 20 | DNA | vCP3012 C3R arm to C3L arm |
| 21 | DNA | vCP3012 C3R arm |
| 22 | DNA | vCP3012 C3L arm |
| 23 | DNA | Fragment of vCP3012 - rabies virus G and flanking regions |
| 24 | DNA | vCP3012 C5R arm |
| 63 | PRT | Felis catus OX40L |
| 64 | PRT | Equus caballus OX40L |
| 65 | PRT | Bos taurus OX40L |
| 66 | PRT | Sus scrofa OX40L |
| 67 | PRT | Pan troglodytes OX40L |
| 68 | DNA | Plasmid p397-cOX40L (pC6 42Kp cOX40L) |
| 69 | DNA | Plasmid p397-Syn Rabies G (pC3 I3Lp Syn Rabies G) |
| 70 | PRT | Gallus gallus OX40L |
| 71 | PRT | Ovis aries OX40L |

*FIG. 36*

| Primer name | Sequences (5'→3') | Gene | SEQ ID |
|---|---|---|---|
| C5R.1R primer | CTCTTGCATATTCGTAATAGTAATTG | | 25 |
| C5R.1F primer | ATTCTATCGGAAGATAGGATACCAG | | 26 |
| C5R.2R primer | TCAACAACCGCTCGTGAACAGCTTC | | 27 |
| C5R.2F primer | ATGCACAACTTCTTGTCTGCATGATG | | 28 |
| C5R.3R primer | TACGGCTATATGTAGAGGAGTTAACC | | 29 |
| C5R.3F primer | CTCTGAGACACAAAAGAGGTAGCTG | | 30 |
| C5L.1F primer | CATCATGAGCAACGCGTTAGTATAT | | 31 |
| C5L.1R primer | TTAGAAATTATGCATTTTAGA | | 32 |
| C5L.2R primer | GGAGATACCTTTAGATATGGATCTG | Classic G/C5 | 33 |
| C5L.3R primer | TTGTAACCATAGTATATCTTAGCGC | | 34 |
| 7634CXL-F primer | GTTCTCGTAGGAGAGAACTATTGAC | | 35 |
| 7635CXL-R primer | CGTCTTCAGCTGTAAACAAATATAATG | | 36 |
| CP65.1F primer | ATGGTTCCTCAGGCTCTCCTGTTTG | | 37 |
| CP65.1R primer | TCACAGTCTGGTCTCACCCCCACTC | | 38 |
| CP65.2R primer | GACCCATGTTCCATCCATAA | | 39 |
| CP65.3F primer | GTCTCACCCCCACTCTTGTGTG | | 40 |
| CP65.4F primer | GAAAACGGTAGACGGGTCTG | | 41 |
| C3R.1F primer | CATAGCTTTATGTAAAGGAGTAT | | 42 |
| C3R.2F primer | TGTAATGGGGTTTTACCTAA | | 43 |
| C3R.3F primer | GCTTTATGAAGAGGAGGATTTT | | 44 |
| C3R.4F primer | GCATTCAGCAGAACATTTCT | | 45 |
| C3L.1F primer | TAGTTACTCTCGTATGGCGT | | 46 |
| C3L.1R primer | ATCAGTAACGTATAGCATACG | | 47 |
| C3L.2R primer | TACATATTTCTAATGTTAACATATT | | 48 |
| I3L.1F primer | GGATCCCTCGAGATGAGATA | Synthetic G/C3 | 49 |
| RabG.PF primer | ATAGCTTGTATGCTTTTTATTTGAT | | 50 |
| RabG.PR primer | GAACAGCAGGGCCTGGGGCACCATG | | 51 |
| RabG.1F primer | GTGAAAACCACCAAGGAGTC | | 52 |
| RabG.1R primer | TTCTGTTCACCCTCCGGCAG | | 53 |
| RabG.2R primer | TGGTGAAGATGTCGCAGCTCATGCC | | 54 |
| RabG.2F primer | ACCACCAAGAGCGTGTCCTT | | 55 |
| RabG.3F primer | TTCCTGATGACCTGCTGCCGGA | | 56 |
| C6R.1F primer | GTTCTAAAGTTCTTTCCTCC | | 57 |
| C6R.2F primer | TCTTTCATATCTTGTAGATAAGA | | 58 |
| C6R.3F primer | TGAAGGGGTTGATGGAATAA | cOX40L/C6 | 59 |
| C6L.1R primer | CTATCAAAAGTCTTAATGAGTTAGG | | 60 |
| OX40L.1F primer | ATGGAAGGAGTACAACCATTAGATC | | 61 |
| OX40L.1R primer | TTAATAAGCACAAAATCCACCAGGA | | 62 |

*FIG. 37*

```
SEQ NO:12 (dog); SEQ NO:63 (cat); SEQ NO:64 (horse); SEQ ID NO:65 (cow)
SEQ NO:66 (pig); SEQ NO:67 (chimp); SEQ NO:71 (sheep)
SEQ NO:70 (chicken; first 50 AA not shown for this alignment)
                      51                                              100
SEQ ID: 12     (1)  -MEGVQPLDQNVGNTPGRRFQKNKVLLVAAIIQGLGLLLCFTYICLHFYA
SEQ ID: 63     (1)  -MEGVQPLDENVGNAPGRRFQSNKLLLVTAVIQGLGLLLCFTYICLHFYA
SEQ ID: 67     (1)  -MERVQPLEENVGNAARPRFERNKLLLVASVIQGLGLLLCFTYICLHFSA
SEQ ID: 64     (1)  -MEGVQPLEENVGNTPGRRFQRNKLLLVTSIIQGLGLLLCLTYVCLHFYT
SEQ ID: 65     (1)  -MEGVQPLDENVGNVPGRRFLRNKLLLVASIIQGLGLLLCLTYICLHFYA
SEQ ID: 71     (1)  -MEGVQPLDENVGNAPGRRFLRNKLLLVASIIQGLGLLLCLTYICLHFYA
SEQ ID: 66     (1)  -MEGVQPLDENVGNAPGRRLLRNKLLLVASVIQGLGLLLCLTYICLHLYA
SEQ ID: 70    (51)  KEPAGMRSDDEWRGWQKGQAKRNTLYLVSAATQWILLLACLIYLGTDSLQ
                     101                                              150
SEQ ID: 12    (50)  SQVPPQYPPIQSIRVQFTRCENEKGCIITSPSKDETMKVQDNSIINCDG
SEQ ID: 63    (50)  SQVPPQYPPIQSIKVQFTKCGNGTGCIITSPNKDETMKVQDNSIINCDG
SEQ ID: 67    (50)  LQVSHRYPRIQSIKVQFTEYKKEKGFILTSQKEDEVMKVQNNSVIINCDG
SEQ ID: 64    (50)  SQVPSQYPPIQSIRVQFTSCENEKGFIITSPNQDEIMKVQDNSIINCDG
SEQ ID: 65    (50)  -QVPSQYPPIQSIRVQFTKCENENGFIITSPDADGTMKVQNNSIIITCDG
SEQ ID: 71    (50)  -QVPSQYPPIQSIRVRFT-CENENGFIITSPDADGTMKVQNNSIIITCDG
SEQ ID: 66    (50)  -QVPSQYPPIQSIKVQFTKCENDNGFIITPSSKDGTMKVQNNSIINCDG
SEQ ID: 70   (101)  -LWTPHSDKVKWTYIRYTGQ-SIAGVAMNLSAEFTSIPVINGSIMIPCDG
                     151                                              200
SEQ ID: 12   (100)  FYLISLKGYFSEELSLSLYYR-------KGRGPLFSLSKVTSVDSIGVAY
SEQ ID: 63   (100)  FYLISLKGYFSEELSLSLYYR-------KGRKPLFSLSKVKSVDSIGVAH
SEQ ID: 67   (100)  FYLISLKGYFSQEVNISLHYQ-------KDEEPLFQLKKVRSVNSLMVAS
SEQ ID: 64   (100)  FYLISLKGYFSQEQLSLSLHYR-------KGREPLSSLSKVRSVNSIMVAY
SEQ ID: 65    (99)  FYLISLKGYFSQELSLRLLYR-------KGREPLFSLNMVKIVDSVTVAY
SEQ ID: 71    (98)  FYLISLKGYFSQKLSLRLLYR-------KGREPLFSLNMVKIVDSVTVAY
SEQ ID: 66    (99)  FYLISLKGYFSQELSLMLQYR-------KGRKPLFSLNKVKSVDSVTVAD
SEQ ID: 70   (149)  LYVVSLKGVLSPDLEKSSLKLMMKNTESKNAAPLWERDVQNSSNAVDLIT
                     201                                241
SEQ ID: 12   (143)  LAFKDKVYFNVTTHSTSYKDIQVNGGELILIHQNPGGFCAY
SEQ ID: 63   (143)  LAFKDKVYFNVTTHNTSYKDIQVNGGELIVILQNPGGFCVL
SEQ ID: 67   (143)  LTYKDKVYLNVTTDNTSLDDFHVNGGELILIHQNPGEFCVL
SEQ ID: 64   (143)  LAFKDKVYLNVTTHNTSCDDIQVNGGELILIHQNPGGFCAY
SEQ ID: 65   (142)  LRFKDKVYLNMTTQNASCEDIQVNGGELILIHQNPGGFCVY
SEQ ID: 71   (141)  LRFKDKVYLNVTTQNASCEDIQVNGGELILIHQNPGGFCVY
SEQ ID: 66   (142)  LAFKDKVFLNVTTHSASCEDIQVNGGELILIHQNPGGFCVY
SEQ ID: 70   (199)  MLYLF-AQNNIILSTSSNATIQCLTFSLVLLNP---VFCNP
```

|        | SEQ 12 | SEQ 63 | SEQ 67 | SEQ 64 | SEQ 65 | SEQ 71 | SEQ 66 | SEQ 70 |
|--------|--------|--------|--------|--------|--------|--------|--------|--------|
| SEQ 12 |        | 89     | 68     | 86     | 81     | 81     | 81     | 22     |
| SEQ 63 |        |        | 69     | 82     | 79     | 79     | 82     | 22     |
| SEQ 67 |        |        |        | 73     | 69     | 70     | 69     | 22     |
| SEQ 64 |        |        |        |        | 84     | 83     | 81     | 23     |
| SEQ 65 |        |        |        |        |        | 98     | 88     | 24     |
| SEQ 71 |        |        |        |        |        |        | 88     | 24     |
| SEQ 66 |        |        |        |        |        |        |        | 24     |
| SEQ 70 |        |        |        |        |        |        |        |        |

*FIG. 38*

```
                            SEQUENCE LISTING

<160> NUMBER OF SEQ ID NOS: 71

<210> SEQ ID NO 1
    <211> LENGTH: 524
    <212> TYPE: PRT
    <213> ORGANISM: Rabies virus

<400> SEQUENCE: 1

Met Val Pro Gln Ala Leu Leu Phe Val Pro Leu Leu Val Phe Pro Leu
    1               5                   10                  15

Cys Phe Gly Lys Phe Pro Ile Tyr Thr Ile Pro Asp Lys Leu Gly Pro
                    20                  25                  30

Trp Ser Pro Ile Asp Ile His His Leu Ser Cys Pro Asn Asn Leu Val
                35                  40                  45

Val Glu Asp Glu Gly Cys Thr Asn Leu Ser Gly Phe Ser Tyr Met Glu
            50                  55                  60

Leu Lys Val Gly Tyr Ile Leu Ala Ile Lys Met Asn Gly Phe Thr Cys
    65                  70                  75                  80

Thr Gly Val Val Thr Glu Ala Glu Thr Tyr Thr Asn Phe Val Gly Tyr
                    85                  90                  95

Val Thr Thr Thr Phe Lys Arg Lys His Phe Arg Pro Thr Pro Asp Ala
                    100                 105                 110

Cys Arg Ala Ala Tyr Asn Trp Lys Met Ala Gly Asp Pro Arg Tyr Glu
                115                 120                 125

Glu Ser Leu His Asn Pro Tyr Pro Asp Tyr Arg Trp Leu Arg Thr Val
            130                 135                 140

Lys Thr Thr Lys Glu Ser Leu Val Ile Ile Ser Pro Ser Val Ala Asp
    145                 150                 155                 160

Leu Asp Pro Tyr Asp Arg Ser Leu His Ser Arg Val Phe Pro Ser Gly
                    165                 170                 175

Lys Cys Ser Gly Val Ala Val Ser Ser Thr Tyr Cys Ser Thr Asn His
                    180                 185                 190

Asp Tyr Thr Ile Trp Met Pro Glu Asn Pro Arg Leu Gly Met Ser Cys
                195                 200                 205

Asp Ile Phe Thr Asn Ser Arg Gly Lys Arg Ala Ser Lys Gly Ser Glu
            210                 215                 220

Thr Cys Gly Phe Val Asp Glu Arg Gly Leu Tyr Lys Ser Leu Lys Gly
    225                 230                 235                 240

Ala Cys Lys Leu Lys Leu Cys Gly Val Leu Gly Leu Arg Leu Met Asp
                    245                 250                 255

Gly Thr Trp Val Ala Met Gln Thr Ser Asn Glu Thr Lys Trp Cys Pro
                    260                 265                 270

Pro Asp Gln Leu Val Asn Leu His Asp Phe Arg Ser Asp Glu Ile Glu
                275                 280                 285

His Leu Val Val Glu Glu Leu Val Arg Lys Arg Glu Glu Cys Leu Asp
            290                 295                 300

Ala Leu Glu Ser Ile Met Thr Thr Lys Ser Val Ser Phe Arg Arg Leu
    305                 310                 315                 320
```

```
Ser His Leu Arg Lys Leu Val Pro Gly Phe Gly Lys Ala Tyr Thr Ile
                325                 330                 335

Phe Asn Lys Thr Leu Met Glu Ala Asp Ala His Tyr Lys Ser Val Arg
            340                 345                 350

Thr Trp Asn Glu Ile Leu Pro Ser Lys Gly Cys Leu Arg Val Gly Gly
        355                 360                 365

Arg Cys His Pro His Val Asn Gly Val Phe Phe Asn Gly Ile Ile Leu
    370                 375                 380

Gly Pro Asp Gly Asn Val Leu Ile Pro Glu Met Gln Ser Ser Leu Leu
385                 390                 395                 400

Gln Gln His Met Glu Leu Leu Glu Ser Ser Val Ile Pro Leu Val His
                405                 410                 415

Pro Leu Ala Asp Pro Ser Thr Val Phe Lys Asp Gly Asp Glu Ala Glu
            420                 425                 430

Asp Phe Val Glu Val His Leu Pro Asp Val His Asn Gln Val Ser Gly
        435                 440                 445

Val Asp Leu Gly Leu Pro Asn Trp Gly Lys Tyr Val Leu Leu Ser Ala
    450                 455                 460

Gly Ala Leu Thr Ala Leu Met Leu Ile Ile Phe Leu Met Thr Cys Cys
465                 470                 475                 480

Arg Arg Val Asn Arg Ser Glu Pro Thr Gln His Asn Leu Arg Gly Thr
                485                 490                 495

Gly Arg Glu Val Ser Val Thr Pro Gln Ser Gly Lys Ile Ile Ser Ser
            500                 505                 510

Trp Glu Ser His Lys Ser Gly Gly Glu Thr Arg Leu
        515                 520
```

<210> SEQ ID NO 2
<211> LENGTH: 3609
<212> TYPE: DNA
<213> ORGANISM: Artificial Sequence
<220> FEATURE:
<223> OTHER INFORMATION: Subsequence of recombinant vCP3006 covering the flanking C3 arms, the I3L promoter as well as the synthetic rabies G

<400> SEQUENCE: 2

```
gctttatgaa gaggaggatt tttacatttt aaaatatcgg caccgtgttc tagtaataat     60
tttaccattt ctatatcaga aatacttacg gctaaataca aagacgttga tagtatattt    120
acgttattgt atttgcattt tttaagtata taccttacta aatttatatc tctatacctt    180
atagctttat gcagttcatt tataagtctt ccattactca tttctggtaa tgaagtatta    240
tatatcatta tgatattatc tctattttat tctaataaaa accgttatca tgttatttat    300
tatttgttat aattatacta tttaataaat tataccaaat acttagatac ttattaatac    360
catcctagaa cttgtatttc ttgcccccta aacttggaca tgcactccat taggcgtttc    420
ttgttttcga catcgtcctc cttaacatat cctactgtta tgtgaggatt ccacggatta    480
tctactgtga tatcaccaaa cacgtccttc gaacagggta ccgcattcag cagaacattt    540
cttagggctc taagttcatc agatacctcc agtttcataa ctacagcgca tcctttcgct    600
cccaactgtt tagaggcgtt actctgagga aaacacatct cttctttaca gactatagaa    660
atagtctgta aatcttgatc agttatttgc tttttgaaat tttcaaatct atcacattga    720
tccatatttg ctattccaag agttatatga ggaaaaatat cacatcctgt catgtatttt    780
attgtaacat tattataatc tgtaacatca gtatctaacc taacgtcgta aaagttaaca    840
```

```
gatgcccagt tactataatc ccaaggaacc ttaacatcta atcccattaa aatagtatcc     900
tttctactat ttttttcatt ggcaagtatg tggcttagtt tacacaaaat tcctgccatt     960
ttgtaacgat agcgaagcaa tagcttgtat gcttttt att tgattaacta gtcataaaaa   1020
tcgggatccc tcgagatgag ataaagtgaa aatatatatc attatattac aaagtacaat    1080
tatttaggtt taatcatggt gccccaggcc ctgctgttcg tgccctgct ggtgttcccc     1140
ctgtgcttcg gcaagttccc catctacacc atccccgaca agctgggccc ctggagcccc    1200
atcgacatcc accacctgag ctgccccaac aatctggtgg tggaggatga gggctgcacc    1260
aatctgagcg gcttcagcta catggagctg aaagtgggct acatcctggc catcaagatg    1320
aacggcttca cctgcaccgg cgtggtgacc gaggccgaga cctacaccaa ctttgtgggc    1380
tacgtgacca ccaccttcaa gcggaagcac ttcagaccta cccccgacgc ctgcagagcc    1440
gcctacaact ggaagatggc cggcgaccct agatacgagg agagcctgca acccctac     1500
cccgactaca gatggctgcg gaccgtgaaa accaccaagg agtccctggt gatcatcagc    1560
cctagcgtgg ccgatctgga cccctacgac agaagcctgc acagcagagt gttccctagc    1620
ggcaagtgca gcgcgtggc cgtgtccagc acctactgca gcaccaacca cgactacacc    1680
atctggatgc ccgagaaccc tagactgggc atgagctgcg acatcttcac caacagccgg    1740
ggcaagagag ccagcaaggg cagcgagacc tgcggcttcg tggacgagag aggcctgtac    1800
aagagcctga agggcgcctg caagctgaag ctgtgcggcg tgctgggcct gagactgatg    1860
gacggcacct gggtggccat gcagaccagc aacgagacca gtggtgccc tcctgaccag    1920
ctggtgaacc tgcacgactt ccggagcgat gagatcgagc acctggtggt ggaagagctg    1980
gtgcggaaga gagaggagtg cctggacgcc ctggagagca tcatgaccac caagagcgtg    2040
tccttccgga gactgagcca cctgagaaag ctggtgcccg gctttggcaa ggcctacaca    2100
atcttcaaca gaccctgat ggaggccgat gcccactaca gtctgtgcg gacctggaac     2160
gagatcctgc ctagcaaggg ctgcctgaga gtgggcggca gatgccaccc ccacgtgaac    2220
ggcgtgttct tcaacggcat catcctgggc cctgacggca acgtgctgat ccctgagatg    2280
cagagcagcc tgctgcagca gcacatggaa ctgctggaga gcagcgtgat cccctggtg    2340
cacccctgg ccgaccccag caccgtgttc aaggatggcg acgaggccga ggacttcgtg    2400
gaggtgcacc tgcccgatgt gcacaaccag gtgtccggcg tggacctggg cctgcccaac    2460
tggggcaagt acgtgctgct gagcgccgga gccctgaccg ccctgatgct gatcatcttc    2520
ctgatgacct gctgccggag ggtgaacaga agcgagccca cccagcacaa cctgagaggc    2580
accggcagag aggtgtccgt gacccccag agcggcaaga tcatcagcag ctgggagagc    2640
cacaagagcg gcgagagac cagactatga ttttatgcc cgggttttta tagctaatta    2700
gtcaaatgtg agttaatatt agtatactac attactaatt tattacatat tcatttatat    2760
caatctagta gcatttagct tttataaaac aatataactg aatagtacat actttactaa    2820
taagttataa ataagagata catatttata gtattttact ttctacactg aatataataa    2880
tataattata caaatataat ttttaatact atatagtata taactgaaat aaaataccag    2940
tgtaatatag ttattataca tttataccac atcaaagatg agttataaca tcagtgtcac    3000
tgttagcaac agtagttata cgatgagtag ttactctcgt atggcgttag tatgtatgta    3060
tcttctagtt ttcttagtag gcattatagg aaacgtcaag cttataaggt tattaatggt    3120
atctagaaat atatctatta taccgtttct caacttggga atagccgatt tgctgtttgt    3180
```

```
gatattcata cctttataca ttatatacat actaagtaat ttccattggc attttggtaa   3240
agcactttgt aaaattagtt cttttctttt tacttctaac atgtttgcaa gtatattttt   3300
aataactgta ataagcgtat atagatatgt aaaaattacc cttcctggat ttacctataa   3360
atatgttaac attagaaata tgtacattac tatatttttc atgggatta tttctattat    3420 actagggatt cctgctcttt actttagaaa tactatcgta acaaaaaata acgacacgct   3480
gtgtattaat cattatcatg ataatagaga aattgctgaa ttgatttaca aagttattat   3540
ctgtatcaga tttattttag gatacctact acctacgata attatactcg tatgctatac   3600
gttactgat                                                           3609

<210> SEQ ID NO 3
<211> LENGTH: 991
<212> TYPE: DNA
<213> ORGANISM: Artificial Sequence
<220> FEATURE:
<223> OTHER INFORMATION: vCP3006 C3 Right arm

<400> SEQUENCE: 3
gctttatgaa gaggaggatt tttacatttt aaaatatcgg caccgtgttc tagtaataat     60
tttaccattt ctatatcaga aatacttacg gctaaataca aagacgttga tagtatattt    120
acgttattgt atttgcattt tttaagtata taccttacta aatttatatc tctataccTt    180
atagctttat gcagttcatt tataagtctt ccattactca tttctggtaa tgaagtatta    240
tatatcatta tgatattatc tctattttat tctaataaaa accgttatca tgttatttat    300
tatttgttat aattatacta tttaataaat tataccaaat acttagatac ttattaatac    360
catcctagaa cttgtatttc ttgcccccta aacttggaca tgcactccat taggcgtttc    420
ttgttttcga catcgtcctc cttaacatat cctactgtta tgtgaggatt ccacggatta    480
tctactgtga tatcaccaaa cacgtccttc gaacagggta ccgcattcag cagaacattt    540
cttagggctc taagttcatc agatacctcc agtttcataa ctacagcgca tcctttcgct    600
cccaactgtt tagaggcgtt actctgagga aaacacatct cttctttaca gactatagaa    660
atagtctgta aatcttgatc agttattgc tttttgaaat tttcaaatct atcacattga     720
tccatatttg ctattccaag agttatatga ggaaaaatat cacatcctgt catgtatttt    780
attgtaacat tattataatc tgtaacatca gtatctaacc taacgtcgta aaagttaaca    840
gatgcccagt tactataatc ccaaggaacc ttaacatcta atcccattaa aatagtatcc    900
tttctactat tttttcatt ggcaagtatg tggcttagtt tacacaaaat tcctgccatt    960
ttgtaacgat agcgaagcaa tagcttgtat g                                    991

<210> SEQ ID NO 4
<211> LENGTH: 60
<212> TYPE: DNA
<213> ORGANISM: Artificial Sequence
<220> FEATURE:
<223> OTHER INFORMATION: I3L promoter

<400> SEQUENCE: 4
atgagataaa gtgaaaatat atatcattat attacaaagt acaattattt aggtttaatc     60

<210> SEQ ID NO 5
<211> LENGTH: 2667
<212> TYPE: DNA
<213> ORGANISM: Artificial Sequence
<220> FEATURE:
<223> OTHER INFORMATION: Synthetic codon-optimized rabies G gene
```

<400> SEQUENCE: 5

```
gctttatgaa gaggaggatt tttacatttt aaaatatcgg caccgtgttc tagtaataat      60
tttaccattt ctatatcaga aatacttacg gctaaataca aagacgttga tagtatattt     120
acgttattgt atttgcattt tttaagtata taccttacta aatttatatc tctataccttt    180
atagctttat gcagttcatt tataagtctt ccattactca tttctggtaa tgaagtatta    240
tatatcatta tgatattatc tctattttat tctaataaaa accgttatca tgttatttat    300
tatttgttat aattatacta tttaataaat tataccaaat acttagatac ttattaatac    360
catcctagaa cttgtatttc ttgcccccta aacttggaca tgcactccat taggcgtttc    420
ttgttttcga catcgtcctc cttaacatat cctactgtta tgtgaggatt ccacggatta    480
tctactgtga tatcaccaaa cacgtccttc gaacagggta ccgcattcag cagaacattt    540
cttagggctc taagttcatc agatacctcc agtttcataa ctacagcgca tcctttcgct    600
cccaactgtt tagaggcgtt actctgagga aaacacatct cttctttaca gactatagaa    660
atagtctgta aatcttgatc agttatttgc tttttgaaat tttcaaatct atcacattga    720
tccatatttg ctattccaag agttatatga ggaaaaatat cacatcctgt catgtattt     780
attgtaacat tattataatc tgtaacatca gtatctaacc taacgtcgta aaagttaaca    840
gatgcccagt tactataatc ccaaggaacc ttaacatcta atcccattaa aatagtatcc    900
tttctactat ttttttcatt ggcaagtatg tggcttagtt tacacaaaat tcctgccatt    960
ttgtaacgat agcgaagcaa tagcttgtat gcttttttatt tgattaacta gtcataaaaa   1020
tcgggatccc tcgagatgag ataaagtgaa aatatatatc attatattac aaagtacaat   1080
tatttaggtt taatcatggt gccccaggcc ctgctgttcg tgccctgct ggtgttcccc     1140
ctgtgcttcg gcaagttccc catctacacc atccccgaca agctgggccc ctggagcccc   1200
atcgacatcc accacctgag ctgccccaac aatctggtgg tggaggatga gggctgcacc   1260
aatctgagcg gcttcagcta catggagctg aaagtgggct acatcctggc catcaagatg   1320
aacggcttca cctgcaccgg cgtggtgacc gaggccgaga cctacaccaa ctttgtgggc   1380
tacgtgacca ccaccttcaa gcggaagcac ttcagaccta cccccgacgc ctgcagagcc   1440
gcctacaact ggaagatggc cggcgaccct agatacgagg agagcctgca caaccctac    1500
cccgactaca gatggctgcg gaccgtgaaa accaccaagg agtccctggt gatcatcagc   1560
cctagcgtgg ccgatctgga cccctacgac agaagcctgc acagcagagt gttccctagc   1620
ggcaagtgca gcggcgtggc cgtgtccagc acctactgca gcaccaacca cgactacacc   1680
atctggatgc ccgagaaccc tagactgggc atgagctgcg acatcttcac caacagccgg   1740
ggcaagagag ccagcaaggg cagcgagacc tgcggcttcg tggacgagag aggcctgtac   1800
aagagcctga agggcgcctg caagctgaag ctgtgcggcg tgctgggcct gagactgatg   1860
gacggcaccct gggtggccat gcagaccagc aacgagacca gtggtgccc tcctgaccag   1920
ctggtgaacc tgcacgactt ccggagcgat gagatcgagc acctggtggt ggaagagctg   1980
gtgcggaaga gagaggagtg cctggacgcc ctggagagca tcatgaccac caagagcgtg   2040
tccttccgga gactgagcca cctgagaaag ctggtgcccg ctttggcaa ggcctacaca    2100
atcttcaaca gaccctgat ggaggccgat gcccactaca gtctgtgcg gacctggaac     2160
gagatcctgc ctagcaaggg ctgcctgaga gtgggcggca gatgcacccc cacgtgaac    2220
ggcgtgttct tcaacggcat catcctgggc cctgacggca acgtgctgat ccctgagatg   2280
```
cagagcagcc tgctgcagca gcacatggaa ctgctggaga gcagcgtgat cccctggtg      2340 caccccctgg ccgaccccag caccgtgttc aaggatggcg acgaggccga ggacttcgtg      2400
gaggtgcacc tgcccgatgt gcacaaccag gtgtccggcg tggacctggg cctgcccaac      2460
tggggcaagt acgtgctgct gagcgccgga gccctgaccg ccctgatgct gatcatcttc      2520
ctgatgacct gctgccggag ggtgaacaga agcgagccca cccagcacaa cctgagaggc      2580
accggcagag aggtgtccgt gaccccccag agcggcaaga tcatcagcag ctgggagagc      2640
cacaagagcg gcggagagac cagacta                                          2667

<210> SEQ ID NO 6
<211> LENGTH: 939
<212> TYPE: DNA
<213> ORGANISM: Artificial Sequence
<220> FEATURE:
<223> OTHER INFORMATION: vCP3006 C3 right arm

<400> SEQUENCE: 6 ttttatgcc cgggttttta tagctaatta gtcaaatgtg agttaatatt agtatactac       60
attactaatt tattacatat tcatttatat caatctagta gcatttagct tttataaaac      120
aatataactg aatagtacat actttactaa taagttataa ataagagata catatttata      180
gtattttact ttctacactg aatataataa tataattata caaatataat ttttaatact     240
atatagtata taactgaaat aaaataccag tgtaatatag ttattataca tttataccac      300
atcaaagatg agttataaca tcagtgtcac tgttagcaac agtagttata cgatgagtag      360
ttactctcgt atggcgttag tatgtatgta tcttctagtt ttcttagtag gcattatagg      420
aaacgtcaag cttataaggt tattaatggt atctagaaat atatctatta taccgtttct      480
caacttggga atagccgatt tgctgtttgt gatattcata cctttataca ttatatacat      540
actaagtaat ttccattggc attttggtaa agcactttgt aaaattagtt ctttcttttt      600
tacttctaac atgtttgcaa gtatatttt aataactgta ataagcgtat atagatatgt       660
aaaaattacc cttcctggat ttacctataa atatgttaac attagaaata tgtacattac      720 tatattttc atatggatta tttctattat actagggatt cctgctcttt actttagaaa      780
tactatcgta acaaaaaata acgacacgct gtgtattaat cattatcatg ataatagaga      840
aattgctgaa ttgatttaca aagttattat ctgtatcaga tttattttag gatacctact      900
acctacgata attatactcg tatgctatac gttactgat                             939

<210> SEQ ID NO 7
<211> LENGTH: 2141
<212> TYPE: DNA
<213> ORGANISM: Artificial Sequence
<220> FEATURE:
<223> OTHER INFORMATION: Fragment of vCP3015 C6R to C6L

<400> SEQUENCE: 7
gttctaaagt tctttcctcc gaaggtatag aacaaagtat tcttctaca tccttactat       60 ttattgcagc ttttaacagc ctatcacgta tcctattttt agtattggta gaacgttta      120 gttctaaagt taaatatta gacataattg gcatattgct tattccttgc atagttgagt      180
ctgtagatcg tttcagtata tcactgatta atgtactact gttatgatga aatatagaat      240
cgatattggc atttaactgt tttgttatac taagtctaga ttttaaatct tctagtaata     300
tgctatttaa tataaaagct tccacgtttt tgtatacatt tctttccata ttagtagcta     360
ctactaaatg attatcttct ttcatatctt gtagataaga tagactatct ttatcttat      420

```
tagtagaaaa tacttctggc catacatcgt taaattttt tgttgttgtt agatataata      480
ttaaatatct agaggatcct attatttgtg gtaaaatgtt tatagagtaa aatgatctgg     540
ctattaaaca taggccagtt accatagaat gctgcttccc gttacagtgt tttaccataa     600
ccatagatct gcctgtattg ttgatacata taacagctgt aaatcctaaa aaattcctat     660
cataattatt aatattaggt aattcatttc catgtgaaag atagactaat tttatatcct     720
ttacctccaa ataattattt acatctctta aacaatctat tttaatatca ttaactggta     780
ttttataata tccagaaagg tttgaagggg ttgatggaat aagtctatta acatcgttaa     840
gtaaattatt aatatcatga atctttatta tattataccc ataagttaaa tttatattta     900
ctttctcatc atctgactta gttagtttgt aataaggtgt gtctgaaaaa attaaaaggt     960
aattcgttga atgaagctgt atttgctgta tcatttttat ctaattttgg agatttagca    1020
gtacttactt cattagaaga agaatctgcc agttcctgtc tattactgat atttcgtttc    1080
attattatat gatttatatt ttacttttc aattatatat actcatttga ctagttaatc    1140
aataaaaaga attctcaaaa ttgaaaatat ataattacaa tataaaatgg aaggagtaca    1200
accattagat caaaatgttg gaaatacacc aggaagaaga tttcaaaaaa ataaagtatt    1260
attagtagca gcaataattc aaggtttagg attattatta tgttttacat atatatgttt    1320
acacttttat gcatctcaag taccacctca atatccacct atacaaagta taagagttca    1380
gtttacaaga tgtgaaaatg aaaaaggttg tattattaca tctccaagta aagatgaaac    1440
tatgaaagta caagataatt caataatcat aaattgtgat ggttttttact taattagttt    1500 aaaaggatat ttttcagaag aattatcatt atctttatat tatagaaaag gtagaggacc    1560
tttattttct ttatcaaaag taacatcagt tgattctatt ggagttgcat atttggcttt    1620
taaagataaa gtatattta atgttacaac tcattctact agttataaag atatacaagt    1680
aaatggtggt gaattaatat taatacatca aaatcctggt ggattttgtg cttattaatt    1740
tttatcccgg gttttatag ctaattagtc attttttcgta agtaagtatt tttatttaat    1800 acttttatt gtacttatgt taaatataac tgatgataac aaaatccatt atgtattatt    1860
tataactgta atttctttag cgtagttaga tgtccaatct ctctcaaata catcggctat    1920 cttttagtg agattttgat ctatgcagtt gaaacttatg aacgcgtgat gattaaaatg    1980
tgaaccgtcc aaatttgcag tcattatatg agcgtatcta ttatctacta tcatcatctt    2040
tgagttatta atatcatcta ctttagaatt gataggaaat atgaatacct ttgtagtaat    2100
atctatacta tctacaccta actcattaag acttttgata g                       2141
```

<210> SEQ ID NO 8
<211> LENGTH: 1148
<212> TYPE: DNA
<213> ORGANISM: Artificial Sequence
<220> FEATURE:
<223> OTHER INFORMATION: vCP3015 C6R

<400> SEQUENCE: 8

```
gttctaaagt tctttcctcc gaaggtatag aacaaagtat ttcttctaca tccttactat      60
ttattgcagc tttaacagc ctatcacgta tcctattttt agtattggta gaacgttta      120 gttctaaagt taaaatatta gacataattg gcatattgct tattccttgc atagttgagt    180
ctgtagatcg tttcagtata tcactgatta atgtactact gttatgatga aatatagaat    240
cgatattggc atttaactgt tttgttatac taagtctaga ttttaaatct tctagtaata    300
```

```
tgctatttaa tataaaagct tccacgtttt tgtatacatt tctttccata ttagtagcta      360
ctactaaatg attatcttct ttcatatctt gtagataaga tagactatct ttatctttat      420
tagtagaaaa tacttctggc catacatcgt taaatttttt tgttgttgtt agatataata      480
ttaaatatct agaggatcct attatttgtg gtaaaatgtt tatagagtaa aatgatctgg      540
ctattaaaca taggccagtt accatagaat gctgcttccc gttacagtgt tttaccataa      600
ccatagatct gcctgtattg ttgatacata aacagctgt aaatcctaaa aaattcctat       660
cataattatt aatattaggt aattcatttc catgtgaaag atagactaat tttatatcct      720
ttacctccaa ataattattt acatctctta aacaatctat tttaatatca ttaactggta      780
ttttataata tccagaaagg tttgaagggg ttgatggaat aagtctatta acatcgttaa      840
gtaaattatt aatatcatga atctttatta tattataccc ataagttaaa tttatattta      900
ctttctcatc atctgactta gttagtttgt aataaggtgt gtctgaaaaa attaaaaggt      960
aattcgttga atgaagctgt atttgctgta tcattttat ctaatttgg agatttagca       1020 gtacttactt cattagaaga agaatctgcc agttcctgtc tattactgat atttcgtttc     1080
attattatat gattatatt ttactttttc aattatatat actcatttga ctagttaatc      1140
aataaaaa                                                              1148

<210> SEQ ID NO 9
<211> LENGTH: 36
<212> TYPE: DNA
<213> ORGANISM: Artificial Sequence
<220> FEATURE:
<223> OTHER INFORMATION: 42K promoter

<400> SEQUENCE: 9
attctcaaaa ttgaaaatat ataattacaa tataaa                                36

<210> SEQ ID NO 10
<211> LENGTH: 549
<212> TYPE: DNA
<213> ORGANISM: Artificial Sequence
<220> FEATURE:
<223> OTHER INFORMATION: cOX40L

<400> SEQUENCE: 10
atggaaggag tacaaccatt agatcaaaat gttggaaata caccaggaag aagatttcaa      60
aaaaataaag tattattagt agcagcaata attcaaggtt taggattatt attatgtttt     120
acatatatat gtttacactt ttatgcatct caagtaccac tcaatatcc acctatacaa      180 agtataagag ttcagtttac aagatgtgaa atgaaaaag gttgtattat tacatctcca     240
agtaaagatg aaactatgaa agtacaagat aattcaataa tcataaattg tgatggtttt     300
tacttaatta gtttaaaagg atattttcca gaagaattat cattatcttt atattataga    360
aaaggtagag gacctttatt ttctttatca aagtaacat cagttgattc tattggagtt     420
gcatatttgg cttttaaaga taagtatat tttaatgtta caactcattc tactagttat    480
aaagatatac aagtaaatgg tggtgaatta atattaatac atcaaaatcc tggtggattt    540
tgtgcttat                                                            549

<210> SEQ ID NO 11
<211> LENGTH: 364
<212> TYPE: DNA
<213> ORGANISM: Artificial Sequence
<220> FEATURE:
<223> OTHER INFORMATION: vCP3015 C6L arm
```

<400> SEQUENCE: 11
gtaagtaagt atttttattt aatacttttt attgtactta tgttaaatat aactgatgat 60
aacaaaatcc attatgtatt atttataact gtaatttctt tagcgtagtt agatgtccaa 120
tctctctcaa atacatcggc tatcttttta gtgagatttt gatctatgca gttgaaactt 180
atgaacgcgt gatgattaaa atgtgaaccg tccaaatttg cagtcattat atgagcgtat 240
ctattatcta ctatcatcat ctttgagtta ttaatatcat ctactttaga attgatagga 300
aatatgaata cctttgtagt aatatctata ctatctacac ctaactcatt aagacttttg 360
atag 364

<210> SEQ ID NO 12
<211> LENGTH: 183
<212> TYPE: PRT
<213> ORGANISM: Artificial Sequence
<220> FEATURE:
<223> OTHER INFORMATION: Predicted amino acid sequence of synthetic cOX40L

<400> SEQUENCE: 12

Met Glu Gly Val Gln Pro Leu Asp Gln Asn Val Gly Asn Thr Pro Gly
1 5 10 15

Arg Arg Phe Gln Lys Asn Lys Val Leu Leu Val Ala Ala Ile Ile Gln
20 25 30

Gly Leu Gly Leu Leu Leu Cys Phe Thr Tyr Ile Cys Leu His Phe Tyr
35 40 45

Ala Ser Gln Val Pro Pro Gln Tyr Pro Pro Ile Gln Ser Ile Arg Val
50 55 60

Gln Phe Thr Arg Cys Glu Asn Glu Lys Gly Cys Ile Ile Thr Ser Pro
65 70 75 80

Ser Lys Asp Glu Thr Met Lys Val Gln Asp Asn Ser Ile Ile Ile Asn
85 90 95

Cys Asp Gly Phe Tyr Leu Ile Ser Leu Lys Gly Tyr Phe Ser Glu Glu
100 105 110

Leu Ser Leu Ser Leu Tyr Tyr Arg Lys Gly Arg Gly Pro Leu Phe Ser
115 120 125

Leu Ser Lys Val Thr Ser Val Asp Ser Ile Gly Val Ala Tyr Leu Ala
130 135 140

Phe Lys Asp Lys Val Tyr Phe Asn Val Thr Thr His Ser Thr Ser Tyr
145 150 155 160

Lys Asp Ile Gln Val Asn Gly Gly Glu Leu Ile Leu Ile His Gln Asn
165 170 175

Pro Gly Gly Phe Cys Ala Tyr
180

<210> SEQ ID NO 13
<211> LENGTH: 3279
<212> TYPE: DNA
<213> ORGANISM: Artificial Sequence
<220> FEATURE:
<223> OTHER INFORMATION: Fragment of vCP3015 C5 Right arm to Classic Rabies G

<400> SEQUENCE: 13
gctataaata tgcattggaa aaataatcca tttaaagaaa ggattcaaat actacaaaac 60
ctaagcgata atatgttaac taagcttatt cttaacgacg ctttaaatat acacaaataa 120

-continued

```
acataatttt tgtataacct aacaaataac taaaacataa aaataataaa aggaaatgta      180
atatcgtaat tattttactc aggaatgggg ttaaatattt atatcacgtg tatatctata      240
ctgttatcgt atactcttta caattactat tacgaatatg caagagataa taagattacg      300
tatttaagag aatcttgtca tgataattgg gtacgacata gtgataaatg ctatttcgca      360
tcgttacata aagtcagttg aaagatgga tttgacagat gtaacttaat aggtgcaaaa       420
atgttaaata acagcattct atcggaagat aggataccag ttatattata caaaaatcac      480
tggttggata aaacagattc tgcaatattc gtaaagatg aagattactg cgaatttgta       540
aactatgaca ataaaaagcc atttatctca cgacatcgt gtaattcttc catgttttat       600
gtatgtgttt cagatattat gagattacta taaactttt gtatacttat attccgtaaa       660
ctatattaat catgaagaaa atgaaaaagt atagaagctg ttcacgagcg gttgttgaaa      720
acaacaaaat tatacattca agatggctta catatacgtc tgtgaggcta tcatggataa      780
tgacaatgca tctctaaata ggttttgga caatggattc gaccctaaca cggaatatgg       840
tactctacaa tctcctcttg aaatggctgt aatgttcaag aataccgagg ctataaaaat      900
cttgatgagg tatggagcta aacctgtagt tactgaatgc acaacttctt gtctgcatga      960
tgcggtgttg agagacgact acaaaatagt gaaagatctg ttgaagaata actatgtaaa     1020
caatgttctt tacagcggag ctttactcc tttgtgtttg gcagcttacc ttaacaaagt      1080
taatttggtt aaacttctat tggctcattc ggcggatgta gatatttcaa acacggatcg     1140
gttaactcct ctacatatag ccgtatcaaa taaaaattta acaatggtta aacttctatt     1200
gaacaaaggt gctgatactg acttgctgga taacatggga cgtactcctt taatgatcgc     1260
tgtacaatct ggaaatattg aaatatgtag cacactactt aaaaaaaata aaatgtccag     1320
aactgggaaa aattgatctt gccagctgta attcatggta gaaagaagt gctcaggcta      1380 cttttcaaca aaggagcaga tgtaaactac atctttgaaa gaaatggaaa atcatatact     1440
gttttggaat tgattaaaga aagttactct gagacacaaa agaggtagct gaagtggtac     1500
tctcaaaagc ttcccgggtt aattaattag ttattagaca aggtgaaaac gaaactattt     1560
gtagcttaat taattagagc ttcttttattc tatacttaaa aagtgaaaat aaatacaaag     1620
gttcttgagg gttgtgttaa attgaaagcg agaaataatc ataaattatt tcattatcgc     1680
gatatccgtt aagtttgtat cgtaatggtt cctcaagctc tcctgtttgt accccttctg     1740
gtttttccgt tgtgttttgg aaaattccct atttacacaa tcccagacaa gcttggtccc     1800
tggagcccga ttgacataca tcacctcagc tgcccaaaca atttggtagt ggaggacgaa     1860
ggatgcacca acctgtcagg gttctcctac atggaactta agttggata catcttagcc      1920 ataaaaatga acgggttcac ttgcacaggc gttgtgacgg aggctgaaac ctacactaac     1980
ttcgttggtt atgtcacaac cacgttcaaa agaaagcatt tccgcccaac accagatgca     2040
tgtagagccg cgtacaactg gaagatggcc ggtgacccca gatatgaaga gtctctacac     2100
aatccgtacc ctgactaccg ctggcttcga actgtaaaaa ccaccaagga gtctctcgtt     2160
atcatatctc caagtgtagc agatttggac ccatatgaca gatcccttca ctcgagggtc     2220
ttccctagcg ggaagtgctc aggagtagcg gtgtcttcta cctactgctc cactaaccac     2280
gattacacca tttggatgcc cgagaatccg agactaggga tgtcttgtga cattttacc     2340 aatagtagag ggaagagagc atccaaaggg agtgagactt gcggctttgt agatgaaaga     2400
ggcctatata agtcttttaaa aggagcatgc aaactcaagt tatgtggagt tctaggactt    2460
agacttatgg atggaacatg ggtcgcgatg caaacatcaa atgaaaccaa atggtgccct    2520
```

-continued

```
cccgatcagt tggtgaacct gcacgacttt cgctcagacg aaattgagca ccttgttgta    2580
gaggagttgg tcaggaagag agaggagtgt ctggatgcac tagagtccat catgacaacc    2640
aagtcagtga gtttcagacg tctcagtcat ttaagaaaac ttgtccctgg gtttggaaaa    2700
gcatatacca tattcaacaa gaccttgatg gaagccgatg ctcactacaa gtcagtcaga    2760
acttggaatg agatcctccc ttcaaaaggg tgtttaagag ttgggggagg tgtcatcct     2820 catgtgaacg gggtgttttt caatggtata atattaggac ctgacggcaa tgtcttaatc    2880
ccagagatgc aatcatccct cctccagcaa catatggagt tgttggaatc ctcggttatc    2940
ccccttgtgc accccctggc agaccgtct accgttttca aggacggtga cgaggctgag     3000
gattttgttg aagttcacct tcccgatgtg cacaatcagg tctcaggagt tgacttgggt    3060
ctcccgaact gggggaagta tgtattactg agtgcagggg ccctgactgc cttgatgttg    3120
ataattttcc tgatgacatg ttgtagaaga gtcaatcgat cagaacctac gcaacacaat    3180
ctcagaggga cagggaggga ggtgtcagtc actccccaaa gcgggaagat catatcttca    3240
tgggaatcac acaagagtgg gggtgagacc agactgtga                          3279
```

<210> SEQ ID NO 14
<211> LENGTH: 1508
<212> TYPE: DNA
<213> ORGANISM: Artificial Sequence
<220> FEATURE:
<223> OTHER INFORMATION: vCP3015 C5R

<400> SEQUENCE: 14

```
gctataaata tgcattggaa aaataatcca tttaagaaaa ggattcaaat actacaaaac     60
ctaagcgata atatgttaac taagcttatt cttaacgacg ctttaaatat acacaaataa    120
acataatttt tgtataacct aacaaataac taaaacataa aaataataaa aggaaatgta    180
atatcgtaat tattttactc aggaatgggg ttaaatattt atatcacgtg tatatctata    240
ctgttatcgt atactcttta caattactat tacgaatatg caagagataa taagattacg    300
tatttaagag aatcttgtca tgataattgg gtacgacata gtgataaatg ctatttcgca    360
tcgttacata aagtcagttg gaaagatgga tttgacagat gtaacttaat aggtgcaaaa    420
atgttaaata acagcattct atcggaagat aggataccag ttatattata caaaaatcac    480
tggttggata aaacagattc tgcaatattc gtaaagatg aagattactg cgaatttgta    540
aactatgaca ataaaaagcc atttatctca acgacatcgt gtaattcttc catgttttat    600
gtatgtgttt cagatattat gagattacta taaactttt gtatacttat attccgtaaa    660
ctatattaat catgaagaaa atgaaaaagt atagaagctg ttcacgagcg gttgttgaaa    720
acaacaaaat tatacattca agatggctta catacgtc tgtgaggcta tcatggataa     780
tgacaatgca tctctaaata ggttttttgga caatggattc gaccctaaca cggaatatgg    840
tactctacaa tctcctcttg aaatggctgt aatgttcaag aataccgagg ctataaaaat    900
cttgatgagg tatggagcta aacctgtagt tactgaatgc acaacttctt gtctgcatga    960
tgcggtgttg agagacgact acaaaatagt gaaagatctg ttgaagaata actatgtaaa    1020
caatgttctt tacagcggag ctttactccc tttgtgtttg gcagcttacc ttaacaaagt    1080
taatttggtt aaacttctat tggctcattc ggcggatgta gatatttcaa acacggatcg    1140
gttaactcct ctacatatag ccgtatcaaa taaaaattta acaatggtta aacttctatt    1200
gaacaaaggt gctgatactg acttgctgga taacatggga cgtactcctt taatgatcgc    1260
```

| | |
|---|---|
| tgtacaatct ggaaatattg aaatatgtag cacactactt aaaaaaaata aaatgtccag | 1320 |
| aactgggaaa aattgatctt gccagctgta attcatggta gaaagaagt gctcaggcta | 1380 |
| cttttcaaca aaggagcaga tgtaaactac atctttgaaa gaatggaaa atcatatact | 1440 |
| gttttggaat tgattaaaga aagttactct gagacacaaa agaggtagct gaagtggtac | 1500 |
| tctcaaaa | 1508 |

<210> SEQ ID NO 15
<211> LENGTH: 124
<212> TYPE: DNA
<213> ORGANISM: Artificial Sequence
<220> FEATURE:
<223> OTHER INFORMATION: vCP3015 H6 promoter

<400> SEQUENCE: 15

| | |
|---|---|
| ttctttattc tatacttaaa aagtgaaaat aaatacaaag gttcttgagg gttgtgttaa | 60 |
| attgaaagcg agaaataatc ataaattatt tcattatcgc gatatccgtt aagtttgtat | 120 |
| cgta | 124 |

<210> SEQ ID NO 16
<211> LENGTH: 1572
<212> TYPE: DNA
<213> ORGANISM: Artificial Sequence
<220> FEATURE:
<223> OTHER INFORMATION: Classic rabies G gene (wild type)

<400> SEQUENCE: 16

```
atggttcctc aagctctcct gtttgtaccc cttctggttt ttccgttgtg ttttggaaaa     60
ttccctattt acacaatccc agacaagctt ggtccctgga gcccgattga catacatcac    120
ctcagctgcc caaacaattt ggtagtggag gacgaaggat gcaccaacct gtcagggttc    180
tcctacatgg aacttaaagt tggatacatc ttagccataa aaatgaacgg gttcacttgc    240
acaggcgttg tgacggaggc tgaaacctac actaacttcg ttggttatgt cacaaccacg    300
ttcaaaagaa agcatttccg cccaacacca gatgcatgta gagccgcgta caactggaag    360
atggccggtg accccagata tgaagagtct ctacacaatc cgtaccctga ctaccgctgg    420
cttcgaactg taaaaaccac caaggagtct ctcgttatca tatctccaag tgtagcagat    480
ttggacccat atgacagatc ccttcactcg agggtcttcc ctagcgggaa gtgctcagga    540
gtagcggtgt cttctaccta ctgctccact aaccacgatt acaccatttg gatgcccgag    600
aatccgagac tagggatgtc ttgtgacatt tttaccaata gtagagggaa gagagcatcc    660
aaagggagtg agacttgcgg ctttgtagat gaaagaggcc tatataagtc tttaaaagga    720
gcatgcaaac tcaagttatg tggagttcta ggacttagac ttatggatgg aacatgggtc    780
gcgatgcaaa catcaaatga aaccaaatgg tgccctcccg atcagttggt gaacctgcac    840
gactttcgct cagacgaaat tgagcacctt gttgtagagg agttggtcag gaagagagag    900
gagtgtctgg atgcactaga gtccatcatg acaaccaagt cagtgagttt cagacgtctc    960
agtcatttaa gaaaacttgt ccctgggttt ggaaaagcat ataccatatt caacaagacc   1020
ttgatggaag ccgatgctca ctacaagtca gtcagaactt ggaatgagat cctcccttca   1080
aaagggtgtt taagagttgg ggggaggtgt catcctcatg tgaacggggt gtttttcaat   1140
ggtataatat taggacctga cggcaatgtc ttaatcccag agatgcaatc atccctcctc   1200
cagcaacata tggagttgtt ggaatcctcg gttatccccc ttgtgcaccc cctggcagac   1260
ccgtctaccg ttttcaagga cggtgacgag gctgaggatt ttgttgaagt tcaccttccc   1320
```

| gatgtgcaca atcaggtctc aggagttgac ttgggtctcc cgaactgggg gaagtatgta | 1380 |
| ttactgagtg caggggccct gactgccttg atgttgataa ttttcctgat gacatgttgt | 1440 |
| agaagagtca atcgatcaga acctacgcaa cacaatctca gagggacagg gagggaggtg | 1500 |
| tcagtcactc cccaaagcgg gaagatcata tcttcatggg aatcacacaa gagtgggggt | 1560 |
| gagaccagac tg | 1572 |

<210> SEQ ID NO 17
<211> LENGTH: 2141
<212> TYPE: DNA
<213> ORGANISM: Artificial Sequence
<220> FEATURE:
<223> OTHER INFORMATION: vCP3012 C6 Right arm to C6 Left arm

<400> SEQUENCE: 17

| gttctaaagt tctttcctcc gaaggtatag aacaaagtat ttcttctaca tccttactat | 60 |
| ttattgcagc tttaacagc ctatcacgta tcctattttt agtattggta gaacgtttta | 120 |
| gttctaaagt taaaatatta gacataattg gcatattgct tattccttgc atagttgagt | 180 |
| ctgtagatcg tttcagtata tcactgatta atgtactact gttatgatga atatagaat | 240 |
| cgatattggc atttaactgt tttgttatac taagtctaga ttttaaatct tctagtaata | 300 |
| tgctatttaa tataaaagct tccacgtttt tgtatacatt tctttccata ttagtagcta | 360 |
| ctactaaatg attatcttct ttcatatctt gtagataaga tagactatct ttatctttat | 420 |
| tagtagaaaa tacttctggc catacatcgt taaattttt tgttgttgtt agatataata | 480 |
| ttaaatatct agaggatcct attatttgtg gtaaaatgtt tatagagtaa aatgatctgg | 540 |
| ctattaaaca taggccagtt accatagaat gctgcttccc gttacagtgt tttaccataa | 600 |
| ccatagatct gcctgtattg ttgatacata taacagctgt aaatcctaaa aaattcctat | 660 |
| cataattatt aatattaggt aattcatttc catgtgaaag atagactaat tttatatcct | 720 |
| ttacctccaa ataattattt acatctctta aacaatctat tttaatatca ttaactggta | 780 |
| ttttataata tccagaaagg tttgaagggg ttgatggaat aagtctatta acatcgttaa | 840 |
| gtaaattatt aatatcatga atctttatta tattataccc ataagttaaa tttatattta | 900 |
| ctttctcatc atctgactta gttagtttgt aataaggtgt gtctgaaaaa attaaaaggt | 960 |
| aattcgttga atgaagctgt atttgctgta tcatttttat ctaattttgg agatttagca | 1020 |
| gtacttactt cattagaaga agaatctgcc agttcctgtc tattactgat atttcgtttc | 1080 |
| attattatat gatttatatt ttactttttc aattatatat actcatttga ctagttaatc | 1140 |
| aataaaaaga attctcaaaa ttgaaaatat ataattacaa tataaaatgg aaggagtaca | 1200 |
| accattagat caaaatgttg gaaatacacc aggaagaaga tttcaaaaaa ataaagtatt | 1260 |
| attagtagca gcaataattc aaggtttagg attattatta tgttttacat atatatgttt | 1320 |
| acactttat gcatctcaag taccacctca atatccacct atacaaagta taagagttca | 1380 |
| gtttacaaga tgtgaaaatg aaaaaggttg tattattaca tctccaagta aagatgaaac | 1440 |
| tatgaaagta caagataatt caataatcat aaattgtgat ggttttttact taattagttt | 1500 |
| aaaaggatat ttttcagaag aattatcatt atctttatat tatagaaaag gtagaggacc | 1560 |
| tttatttct ttatcaaaag taacatcagt tgattctatt ggagttgcat atttggcttt | 1620 |
| taaagataaa gtatattta atgttacaac tcattctact agttataaag atatacaagt | 1680 |
| aaatggtggt gaattaatat taatacatca aaatcctggt ggattttgtg cttattaatt | 1740 |

```
tttatcccgg gttttttatag ctaattagtc attttttcgta agtaagtatt tttatttaat    1800 acttttatt gtacttatgt taaatataac tgatgataac aaaatccatt atgtattatt      1860
tataactgta atttctttag cgtagttaga tgtccaatct ctctcaaata catcggctat      1920 cttttttagtg agattttgat ctatgcagtt gaaacttatg aacgcgtgat gattaaaatg    1980
tgaaccgtcc aaatttgcag tcattatatg agcgtatcta ttatctacta tcatcatctt      2040
tgagttatta atatcatcta ctttagaatt gataggaaat atgaataccct ttgtagtaat    2100 atctatacta tctacaccta actcattaag acttttgata g                         2141

<210> SEQ ID NO 18
<211> LENGTH: 1148
<212> TYPE: DNA
<213> ORGANISM: Artificial Sequence
<220> FEATURE:
<223> OTHER INFORMATION: vCP3012 C6R arm

<400> SEQUENCE: 18
gttctaaagt tctttcctcc gaaggtatag aacaaagtat ttcttctaca tccttactat       60
ttattgcagc ttttaacagc ctatcacgta tcctattttt agtattggta gaacgtttta     120
gttctaaagt taaatatatta gacataattg gcatattgct tattccttgc atagttgagt    180
ctgtagatcg tttcagtata tcactgatta atgtactact gttatgatga aatatagaat     240
cgatattggc atttaactgt tttgttatac taagtctaga ttttaaatct tctagtaata    300
tgctatttaa tataaaagct tccacgtttt tgtatacatt tctttccata ttagtagcta    360
ctactaaatg attatcttct ttcatatctt gtagataaga tagactatct ttatctttat    420
tagtagaaaa tacttctggc catacatcgt taaattttttt tgttgttgtt agatataata   480
ttaaatatct agaggatcct attatttgtg gtaaaatgtt tatagagtaa atgatctgg     540 ctattaaaca taggccagtt accatagaat gctgcttccc gttacagtgt tttaccataa    600
ccatagatct gcctgtattg ttgatacata taacagctgt aaatcctaaa aaattcctat    660
cataattatt aatattaggt aattcatttc catgtgaaag atagactaat tttatatcct    720
ttacctccaa ataattattt acatctctta aacaatctat tttaatatca ttaactggta    780
ttttataata tccagaaagg tttgaagggg ttgatggaat aagtctatta acatcgttaa    840
gtaaattatt aatatcatga atctttatta tattataccc ataagttaaa tttatattta   900
ctttctcatc atctgactta gttagttttgt aataaggtgt gtctgaaaaa attaaaaggt    960
aattcgttga atgaagctgt atttgctgta tcattttttat ctaattttgg agatttagca    1020
gtacttactt cattagaaga agaatctgcc agttcctgtc tattactgat atttcgtttc    1080
attattatat gatttatatt ttactttttc aattatatat actcatttga ctagttaatc    1140
aataaaaa                                                              1148

<210> SEQ ID NO 19
<211> LENGTH: 365
<212> TYPE: DNA
<213> ORGANISM: Artificial Sequence
<220> FEATURE:
<223> OTHER INFORMATION: vCP3012 C6L arm

<400> SEQUENCE: 19
cgtaagtaag tatttttatt taatactttt tattgtactt atgttaaata taactgatga      60
taacaaaatc cattatgtat tatttataac tgtaattctc ttagcgtagt tagatgtcca     120
atctctctca aatacatcgg ctatcttttt agtgagattt tgatctatgc agttgaaact    180
```

```
tatgaacgcg tgatgattaa aatgtgaacc gtccaaattt gcagtcatta tatgagcgta    240
tctattatct actatcatca tctttgagtt attaatatca tctactttag aattgatagg    300
aaatatgaat acctttgtag taatatctat actatctaca cctaactcat taagactttt    360
gatag                                                                365

<210> SEQ ID NO 20
<211> LENGTH: 4089
<212> TYPE: DNA
<213> ORGANISM: Artificial Sequence
<220> FEATURE:
<223> OTHER INFORMATION: vCP3012 C3R arm to C3L arm

<400> SEQUENCE: 20
tgtaatgggg ttttacctaa atcatcttgt tcgtttatag gcactccgtg atttataagt     60
aacgctatta tatcgtaact acaattattt ttaagtgcct ttatgagata ctgtttatgc    120
aaaaataaac ttttatctat tttaatacta ttatctaaca atatcctaat taaatctata    180
ttcttatact ttatagcgta atgtaacgga gtttcaaaat ttctagtttg tatattaaga    240
tcaatattaa aatctataaa tattttatac atatcatcag atatcttatc atacagtaca    300
tcgtaataat ttagaaagaa tctattacaa ttaacacctt tttttaataa atatctagtt    360
aatgacttat tgtttctata tacagaaata tataacggac tatttccaga atgtatctgt    420
tctatgtcag cgccagaatc tattagtagt ttagcaattt ctgtattatc taaactagca    480 gcttatgaa gaggaggatt tttacatttt aaaatatcgg caccgtgttc tagtaataat    540
tttaccattt ctatatcaga aatacttacg gctaaataca aagacgttga tagtatattt    600
acgttattgt atttgcattt tttaagtata taccttacta aatttatatc tctataccct    660
atagctttat gcagttcatt tataagtctt ccattactca tttctggtaa tgaagtatta    720
tatatcatta tgatattatc tctattttat tctaataaaa accgttatca tgttatttat    780
tatttgttat aattatacta tttaataaat tataccaaat acttagatac ttattaatac    840
catcctagaa cttgtatttc ttgccccta aacttggaca tgcactccat taggcgtttc    900
ttgttttcga catcgtcctc cttaacatat cctactgtta tgtgaggatt ccacggatta    960
tctactgtga tatcaccaaa cacgtccttc gaacagggta ccgcattcag cagaacattt   1020
cttagggctc taagttcatc agatacctcc agtttcataa ctacagcgca tcctttcgct   1080
cccaactgtt tagaggcgtt actctgagga aaacacatct cttctttaca gactatagaa   1140
atagtctgta atcttgatc agttatttgc tttttgaaat tttcaaatct atcacattga   1200
tccatatttg ctattccaag agttatatga ggaaaaatat cacatcctgt catgtatttt   1260
attgtaacat tattataatc tgtaacatca gtatctaacc taacgtcgta aaagttaaca   1320
gatgcccagt tactataatc ccaaggaacc ttaacatcta atcccattaa aatagtatcc   1380
tttctactat ttttttcatt ggcaagtatg tggcttagtt tacacaaaat tcctgccatt   1440
ttgtaacgat agcgaagcaa tagcttgtat gctttttatt tgattaacta gtcataaaaa   1500
tcgggatccc tcgagatgag ataaagtgaa aatatatatc attatattac aaagtacaat   1560
tatttaggtt taatcatggt gccccaggcc ctgctgttcg tgcccctgct ggtgttcccc   1620
ctgtgcttcg gcaagttccc catctacacc atccccgaca agctgggccc ctggagcccc   1680
atcgacatcc accacctgag ctgccccaac aatctggtgg tggaggatga gggctgcacc   1740
aatctgagcg gcttcagcta catggagctg aaagtgggct acatcctggc catcaagatg   1800
```

```
aacggcttca cctgcaccgg cgtggtgacc gaggccgaga cctacaccaa ctttgtgggc    1860
tacgtgacca ccaccttcaa gcggaagcac ttcagaccta cccccgacgc ctgcagagcc    1920
gcctacaact ggaagatggc cggcgaccct agatacgagg agagcctgca caacccctac    1980
cccgactaca gatggctgcg gaccgtgaaa accaccaagg agtccctggt gatcatcagc    2040
cctagcgtgg ccgatctgga cccctacgac agaagcctgc acagcagagt gttccctagc    2100
ggcaagtgca gcggcgtggc cgtgtccagc acctactgca gcaccaacca cgactacacc    2160
atctggatgc ccgagaaccc tagactgggc atgagctgcg acatcttcac caacagccgg    2220
ggcaagagag ccagcaaggg cagcgagacc tgcggcttcg tggacgagag aggcctgtac    2280
aagagcctga agggcgcctg caagctgaag ctgtgcggcg tgctgggcct gagactgatg    2340
gacggcacct gggtggccat gcagaccagc aacgagacca gtggtgcccc tcctgaccag    2400
ctggtgaacc tgcacgactt ccggagcgat gagatcgagc acctggtggt ggaagagctg    2460
gtgcggaaga gagaggagtg cctggacgcc ctggagagca tcatgaccac caagagcgtg    2520
tccttccgga gactgagcca cctgagaaag ctggtgcccg gctttggcaa ggcctacaca    2580
atcttcaaca agaccctgat ggaggccgat gcccactaca agtctgtgcg gacctggaac    2640
gagatcctgc ctagcaaggg ctgcctgaga gtgggcggag gatgccaccc ccacgtgaac    2700
ggcgtgttct tcaacggcat catcctgggc cctgacggca acgtgctgat ccctgagatg    2760
cagagcagcc tgctgcagca gcacatggaa ctgctggaga gcagcgtgat ccccctggtg    2820
caccccctgg ccgaccccag caccgtgttc aaggatggcg acgaggccga ggacttcgtg    2880
gaggtgcacc tgcccgatgt gcacaaccag gtgtccggcg tggacctggg cctgcccaac    2940
tggggcaagt acgtgctgct gagcgccgga gccctgaccg ccctgatgct gatcatcttc    3000
ctgatgacct gctgccggag ggtgaacaga agcgagccca cccagcacaa cctgagaggc    3060
accggcagag aggtgtccgt gaccccccag agcggcaaga tcatcagcag ctgggagagc    3120
cacaagagcg gcgagagac cagactatga ttttatgcc cgggttttta tagctaatta    3180
gtcaaatgtg agttaatatt agtatactac attactaatt tattacatat tcatttatat    3240
caatctagta gcatttagct tttataaaac aatataactg aatagtacat actttactaa    3300
taagttataa ataagagata catatttata gtattttact ttctacactg aatataataa    3360
tataattata caaatataat ttttaatact atatagtata taactgaaat aaaataccag    3420
tgtaatatag ttattataca tttataccac atcaaagatg agttataaca tcagtgtcac    3480
tgttagcaac agtagttata cgatgagtag ttactctcgt atggcgttag tatgtatgta    3540
tcttctagtt ttcttagtag gcattatagg aaacgtcaag cttataaggt tattaatggt    3600
atctagaaat atatctatta taccgtttct caacttggga atagccgatt tgctgtttgt    3660
gatattcata cctttataca ttatatacat actaagtaat ttccattggc attttggtaa    3720
agcactttgt aaaattagtt cttttctttt tacttctaac atgtttgcaa gtatattttt    3780
aataactgta ataagcgtat atagatatgt aaaaattacc cttcctggat ttacctataa    3840
atatgttaac attagaaata tgtacattac tatattttt atatggatta tttctattat    3900
actagggatt cctgctcttt actttagaaa tactatcgta acaaaaaata acgacacgct    3960
gtgtattaat cattatcatg ataatagaga aattgctgaa ttgatttaca aagttattat    4020
ctgtatcaga tttattttag gatacctact acctacgata attatactcg tatgctatac    4080
gttactgat                                                           4089
```

<210> SEQ ID NO 21
<211> LENGTH: 1471
<212> TYPE: DNA
<213> ORGANISM: Artificial Sequence
<220> FEATURE:
<223> OTHER INFORMATION: vCP3012 C3R arm

<400> SEQUENCE: 21

```
tgtaatgggg ttttacctaa atcatcttgt tcgtttatag gcactccgtg atttataagt      60
aacgctatta tatcgtaact acaattattt ttaagtgcct ttatgagata ctgtttatgc     120
aaaaataaac ttttatctat tttaatacta ttatctaaca atatcctaat taaatctata     180
ttcttatact ttatagcgta atgtaacgga gtttcaaaat ttctagtttg tatattaaga     240
tcaatattaa aatctataaa tattttatac atatcatcag atatcttatc atacagtaca     300
tcgtaataat ttagaaagaa tctattacaa ttaaacacctt tttttaataa atatctagtt    360
aatgacttat tgtttctata tacagaaata taacggac tatttccaga atgtatctgt       420
tctatgtcag cgccagaatc tattagtagt ttagcaattt ctgtattatc taaactagca    480
gctttatgaa gaggaggatt tttacatttt aaaatatcgg caccgtgttc tagtaataat    540
tttaccattt ctatatcaga aatacttacg gctaaataca aagacgttga tagtatattt    600
acgttattgt atttgcattt tttaagtata taccttacta aatttatatc tctataccctt   660
atagctttat gcagttcatt tataagtctt ccattactca tttctggtaa tgaagtatta    720
tatatcatta tgatattatc tctatttat tctaataaaa accgttatca tgttatttat     780
tatttgttat aattatacta tttaataaat tataccaaat acttagatac ttattaatac    840
catcctagaa cttgtatttc ttgcccccta aacttggaca tgcactccat taggcgtttc    900
ttgttttcga catcgtcctc cttaacatat cctactgtta tgtgaggatt ccacggatta    960
tctactgtga tatcaccaaa cacgtccttc gaacagggta ccgcattcag cagaacattt   1020
cttagggctc taagttcatc agatacctcc agtttcataa ctacagcgca tcctttcgct   1080
cccaactgtt tagaggcgtt actctgagga aaacacatct cttctttaca gactatagaa   1140
atagtctgta atcttgatc agttattttgc tttttgaaat tttcaaatct atcacattga   1200
tccatatttg ctattccaag agttatatga ggaaaaatat cacatcctgt catgtatttt   1260
attgtaacat tattataatc tgtaacatca gtatctaacc taacgtcgta aaagttaaca   1320
gatgcccagt tactataatc ccaaggaacc ttaacatcta atcccattaa aatagtatcc   1380
tttctactat ttttttcatt ggcaagtatg tggcttagtt tacacaaaat tcctgccatt   1440
ttgtaacgat agcgaagcaa tagcttgtat g                                   1471
```

<210> SEQ ID NO 22
<211> LENGTH: 907
<212> TYPE: DNA
<213> ORGANISM: Artificial Sequence
<220> FEATURE:
<223> OTHER INFORMATION: vCP3012 C3R arm

<400> SEQUENCE: 22

```
caaatgtgag ttaatattag tatactacat tactaattta ttacatattc atttatatca      60
atctagtagc atttagcttt tataaaacaa tataactgaa tagtacatac tttactaata    120
agttataaat aagagataca tatttatagt attttacttt ctacactgaa tataataata    180
taattataca aatataattt ttaatactat atagtatata actgaaataa ataccagtg     240
taatatagtt attatacatt tataccacat caaagatgag ttataacatc agtgtcactg    300
```

```
ttagcaacag tagttatacg atgagtagtt actctcgtat ggcgttagta tgtatgtatc    360
ttctagtttt cttagtaggc attataggaa acgtcaagct tataaggtta ttaatggtat    420
ctagaaatat atctattata ccgtttctca acttgggaat agccgatttg ctgtttgtga    480
tattcatacc tttatacatt atatacatac taagtaattt ccattggcat tttggtaaag    540
cactttgtaa aattagttct ttcttttta cttctaacat gtttgcaagt atattttaa     600 taactgtaat aagcgtatat agatatgtaa aaattacccct tcctggattt acctataaat    660
atgttaacat tagaaatatg tacattacta tattttcat atggattatt tctattatac    720
tagggattcc tgctctttac tttagaaata ctatcgtaac aaaaaataac gacacgctgt    780
gtattaatca ttatcatgat aatagagaaa ttgctgaatt gatttacaaa gttattatct    840
gtatcagatt tattttagga tacctactac ctacgataat tatactcgta tgctatacgt    900
tactgat                                                               907

<210> SEQ ID NO 23
<211> LENGTH: 3279
<212> TYPE: DNA
<213> ORGANISM: Artificial Sequence
<220> FEATURE:
<223> OTHER INFORMATION: Fragment of vCP3012 - rabies virus G and
      flanking regions

<400> SEQUENCE: 23
gctataaata tgcattggaa aaataatcca tttaagaaaa ggattcaaat actacaaaac     60
ctaagcgata atatgttaac taagcttatt cttaacgacg cttttaaatat acacaaataa    120 acataatttt tgtataacct aacaaataac taaaacataa aaataataaa aggaaatgta    180
atatcgtaat tatttactc aggaatgggg ttaaatattt atatcacgtg tatatctata    240
ctgttatcgt atactcttta caattactat tacgaatatg caagagataa taagattacg    300
tatttaagag aatcttgtca tgataattgg gtacgacata gtgataaatg ctatttcgca    360
tcgttacata aagtcagttg gaaagatgga tttgacagat gtaacttaat aggtgcaaaa    420
atgttaaata acagcattct atcggaagat aggataccag ttatattata caaaaatcac    480
tggttggata aaacagattc tgcaatattc gtaaagatg aagattactg cgaatttgta    540
aactatgaca ataaaaagcc atttatctca cgacatcgt gtaattcttc catgttttat    600
gtatgtgttt cagatattat gagattacta taaacttttt gtatacttat attccgtaaa    660
ctatattaat catgaagaaa atgaaaaagt atagaagctg ttcacgagcg gttgttgaaa    720
acaacaaaat tatacattca agatggctta catatacgtc tgtgaggcta tcatggataa    780
tgacaatgca tctctaaata ggttttttgga caatggattc gaccctaaca cggaatatgg    840
tactctacaa tctcctcttg aaatggctgt aatgttcaag aataccgagg ctataaaaat    900
cttgatgagg tatggagcta aacctgtagt tactgaatgc acaacttctt gtctgcatga    960
tgcggtgttg agagacgact acaaaatagt gaaagatctg ttgaagaata actatgtaaa   1020
caatgttctt tacagcggag gctttactcc tttgtgtttg gcagcttacc ttaacaaagt   1080
taatttggtt aaaacttctat tggctcattc ggcggatgta gatatttcaa acacggatcg   1140
gttaactcct ctacatatag ccgtatcaaa taaaaattta acaatggtta aacttctatt   1200
gaacaaaggt gctgatactg acttgctgga taacatggga cgtactcctt taatgatcgc   1260
tgtacaatct ggaaatattg aaatatgtag cacactacta aaaaaaaata aaatgtccag   1320
aactgggaaa aattgatctt gccagctgta attcatggta gaaaagaagt gctcaggcta   1380
```

| | |
|---|---:|
| cttttcaaca aaggagcaga tgtaaactac atctttgaaa gaaatggaaa atcatatact | 1440 |
| gttttggaat tgattaaaga aagttactct gagacacaaa agaggtagct gaagtggtac | 1500 |
| tctcaaaagc ttcccgggtt aattaattag ttattagaca aggtgaaaac gaaactattt | 1560 |
| gtagcttaat taattagagc ttctttattc tatacttaaa aagtgaaaat aaatacaaag | 1620 |
| gttcttgagg gttgtgttaa attgaaagcg agaaataatc ataaattatt tcattatcgc | 1680 |
| gatatccgtt aagtttgtat cgtaatggtt cctcaagctc tcctgtttgt accccttctg | 1740 |
| gttttccgt tgtgttttgg aaaattccct atttacacaa tcccagacaa gcttggtccc | 1800 |
| tggagcccga ttgacataca tcacctcagc tgcccaaaca atttggtagt ggaggacgaa | 1860 |
| ggatgcacca acctgtcagg gttctcctac atggaactta agttggata catcttagcc | 1920 |
| ataaaaatga acgggttcac ttgcacaggc gttgtgacgg aggctgaaac ctacactaac | 1980 |
| ttcgttggtt atgtcacaac cacgttcaaa agaaagcatt tccgcccaac accagatgca | 2040 |
| tgtagagccg cgtacaactg gaagatggcc ggtgacccca gatatgaaga gtctctacac | 2100 |
| aatccgtacc ctgactaccg ctggcttcga actgtaaaaa ccaccaagga gtctctcgtt | 2160 |
| atcatatctc caagtgtagc agatttggac ccatatgaca gatcccttca ctcgagggtc | 2220 |
| ttccctagcg ggaagtgctc aggagtagcg gtgtcttcta cctactgctc cactaaccac | 2280 |
| gattacacca tttggatgcc cgagaatccg agactaggga tgtcttgtga cattttacc | 2340 |
| aatagtagag ggaagagagc atccaaaggg agtgagactt gcggctttgt agatgaaaga | 2400 |
| ggcctatata agtctcttaaa aggagcatgc aaactcaagt tatgtggagt tctaggactt | 2460 |
| agacttatgg atggaacatg ggtcgcgatg caaacatcaa atgaaaccaa atggtgccct | 2520 |
| cccgatcagt tggtgaacct gcacgacttt cgctcagacg aaattgagca ccttgttgta | 2580 |
| gaggagttgg tcaggaagag agaggagtgt ctggatgcac tagagtccat catgacaacc | 2640 |
| aagtcagtga gtttcagacg tctcagtcat ttaagaaaac ttgtccctgg gtttggaaaa | 2700 |
| gcatatacca tattcaacaa gaccttgatg gaagccgatg ctcactacaa gtcagtcaga | 2760 |
| acttggaatg agatcctccc ttcaaaaggg tgtttaagag ttgggggggag tgtcatcct | 2820 |
| catgtgaacg gggtgttttt caatggtata atattaggac ctgacggcaa tgtcttaatc | 2880 |
| ccagagatgc aatcatccct cctccagcaa catatggagt tgttggaatc ctcggttatc | 2940 |
| ccccttgtgc accccctggc agaccccgtct accgttttca aggacggtga cgaggctgag | 3000 |
| gattttgttg aagttcacct tccccgatgtg cacaatcagg tctcaggagt tgacttgggt | 3060 |
| ctcccgaact gggggaagta tgtattactg agtgcagggg ccctgactgc cttgatgttg | 3120 |
| ataattttcc tgatgacatg ttgtagaaga gtcaatcgat cagaacctac gcaacacaat | 3180 |
| ctcagaggga cagggaggga ggtgtcagtc actccccaaa gcgggaagat catatcttca | 3240 |
| tgggaatcac acaagagtgg gggtgagacc agactgtga | 3279 |

<210> SEQ ID NO 24
<211> LENGTH: 3279
<212> TYPE: DNA
<213> ORGANISM: Artificial Sequence
<220> FEATURE:
<223> OTHER INFORMATION: vCP3012 C5R arm

<400> SEQUENCE: 24

| | |
|---|---:|
| gctataaata tgcattggaa aaataatcca tttaagaaa ggattcaaat actacaaaac | 60 |
| ctaagcgata atatgttaac taagcttatt cttaacgacg cttttaatat acacaaataa | 120 |
| acataatttt tgtataacct aacaaataac taaaacataa aaataataaa aggaaatgta | 180 |

```
atatcgtaat tattttactc aggaatgggg ttaaatattt atatcacgtg tatatctata    240
ctgttatcgt atactctta caattactat tacgaatatg caagagataa taagattacg     300
tatttaagag aatcttgtca tgataattgg gtacgacata gtgataaatg ctatttcgca    360
tcgttacata aagtcagttg gaaagatgga tttgacagat gtaacttaat aggtgcaaaa    420
atgttaaata acagcattct atcggaagat aggataccag ttatattata caaaaatcac    480
tggttggata aaacgattc tgcaatattc gtaaagatg aagattactg cgaatttgta      540
aactatgaca ataaaaagcc atttatctca acgacatcgt gtaattcttc catgttttat    600
gtatgtgttt cagatattat gagattacta taaactttt gtatacttat attccgtaaa     660
ctatattaat catgaagaaa atgaaaaagt atagaagctg ttcacgagcg gttgttgaaa    720
acaacaaaat tatacattca agtggctta catatacgtc tgtgaggcta tcatggataa     780
tgacaatgca tctctaaata ggttttggga caatggattc gaccctaaca cggaatatgg    840
tactctacaa tctcctcttg aaatggctgt aatgttcaag aataccgagg ctataaaaat    900
cttgatgagg tatggagcta aacctgtagt tactgaatgc acaacttctt gtctgcatga    960
tgcggtgttg agagacgact acaaaatagt gaaagatctg ttgaagaata actatgtaaa   1020
caatgttctt tacagcggag ctttactcc tttgtgtttg gcagcttacc ttaacaaagt    1080
taatttggtt aaacttctat tggctcattc ggcggatgta gatatttcaa acacggatcg   1140
gttaactcct ctacatatag ccgtatcaaa taaaaattta acaatggtta aacttctatt   1200 gaacaaggt gctgatactg acttgctgga taacatggga cgtactcctt taatgatcgc    1260
tgtacaatct ggaaatattg aaatatgtag cacactactt aaaaaaaata aaatgtccag   1320
aactgggaaa aattgatctt gccagctgta attcatggta gaaagaagt gctcaggcta    1380 cttttcaaca aaggagcaga tgtaaactac atctttgaaa gaaatggaaa atcatatact   1440
gttttggaat tgattaaaga aagttactct gagacacaaa agaggtagct gaagtggtac   1500
tctcaaaagc ttcccggggtt aattaattag ttattagaca aggtgaaaac gaaactattt   1560
gtagcttaat taattagagc ttcttattc tatacttaaa aagtgaaaat aaatacaaag    1620
gttcttgagg gttgtgttaa attgaaagcg agaaataatc ataaattatt tcattatcgc   1680
gatatccgtt aagtttgtat cgtaatggtt cctcaagctc tcctgttgt accccttctg    1740 gttttttccgt tgtgttttgg aaaattccct atttacacaa tcccagacaa gcttggtccc   1800
tggagcccga ttgacataca tcacctcagc tgcccaaaca atttggtagt ggaggacgaa    1860
ggatgcacca acctgtcagg gttctcctac atggaactta aagttggata catcttagcc    1920
ataaaaatga acgggttcac ttgcacaggc gttgtgacgg aggctgaaac ctacactaac    1980
ttcgttggtt atgtcacaac cacgttcaaa agaaagcatt tccgcccaac accagatgca    2040
tgtagagccg cgtacaactg gaagatggcc ggtgacccca gatatgaaga gtctctacac    2100
aatccgtacc ctgactaccg ctggcttcga actgtaaaaa ccaccaagga gtctctcgtt    2160
atcatatctc caagtgtagc agatttggac ccatatgaca gatcccttca ctcgagggtc    2220
ttccctagcg ggaagtgctc aggagtagcg gtgtcttcta cctactgctc cactaaccac    2280
gattaccaca tttggatgcc cgagaatccg agactaggga tgtcttgtga catttttacc    2340
aatagtagag ggaagagagc atccaaaggg agtgagactt gcggctttgt agatgaaaga    2400
ggcctatata agtcttttaaa aggagcatgc aaactcaagt tatgtggagt tctaggactt    2460
agacttatgg atggaacatg ggtcgcgatg caaacatcaa atgaaaccaa atggtgccct    2520
```

```
cccgatcagt tggtgaacct gcacgacttt cgctcagacg aaattgagca ccttgttgta    2580
gaggagttgg tcaggaagag agaggagtgt ctggatgcac tagagtccat catgacaacc    2640
aagtcagtga gtttcagacg tctcagtcat ttaagaaaac ttgtccctgg gtttggaaaa    2700
gcatatacca tattcaacaa gaccttgatg gaagccgatg ctcactacaa gtcagtcaga    2760
acttggaatg agatcctccc ttcaaaaggg tgtttaagag ttgggggggag gtgtcatcct    2820 catgtgaacg gggtgttttt caatggtata atattaggac ctgacggcaa tgtcttaatc    2880
ccagagatgc aatcatccct cctccagcaa catatggagt tgttggaatc ctcggttatc    2940
ccccttgtgc accccctggc agacccgtct accgttttca aggacggtga cgaggctgag    3000
gattttgttg aagttcacct tcccgatgtg cacaatcagg tctcaggagt tgacttgggt    3060
ctcccgaact gggggaagta tgtattactg agtgcagggg ccctgactgc cttgatgttg    3120
ataattttcc tgatgacatg ttgtagaaga gtcaatcgat cagaacctac gcaacacaat    3180
ctcagaggga cagggaggga ggtgtcagtc actccccaaa gcgggaagat catatcttca    3240
tgggaatcac acaagagtgg gggtgagacc agactgtga                           3279
```

<210> SEQ ID NO 25
<211> LENGTH: 26
<212> TYPE: DNA
<213> ORGANISM: Artificial Sequence
<220> FEATURE:
<223> OTHER INFORMATION: C5R.1R primer

<400> SEQUENCE: 25
ctcttgcata ttcgtaatag taattg                                         26

<210> SEQ ID NO 26
<211> LENGTH: 25
<212> TYPE: DNA
<213> ORGANISM: Artificial Sequence
<220> FEATURE:
<223> OTHER INFORMATION: C5R.1F primer

<400> SEQUENCE: 26
attctatcgg aagataggat accag                                          25

<210> SEQ ID NO 27
<211> LENGTH: 25
<212> TYPE: DNA
<213> ORGANISM: Artificial Sequence
<220> FEATURE:
<223> OTHER INFORMATION: C5R.2R primer

<400> SEQUENCE: 27
tcaacaaccg ctcgtgaaca gcttc                                          25

<210> SEQ ID NO 28
<211> LENGTH: 26
<212> TYPE: DNA
<213> ORGANISM: Artificial Sequence
<220> FEATURE:
<223> OTHER INFORMATION: C5R.2F primer

<400> SEQUENCE: 28
atgcacaact tcttgtctgc atgatg                                         26

<210> SEQ ID NO 29
<211> LENGTH: 26
<212> TYPE: DNA
<213> ORGANISM: Artificial Sequence

```
<220> FEATURE:
<223> OTHER INFORMATION: C5R.3R primer

<400> SEQUENCE: 29
tacggctata tgtagaggag ttaacc                                        26

<210> SEQ ID NO 30
<211> LENGTH: 25
<212> TYPE: DNA
<213> ORGANISM: Artificial Sequence
<220> FEATURE:
<223> OTHER INFORMATION: C5R.3F primer

<400> SEQUENCE: 30
ctctgagaca caaagaggt agctg                                          25

<210> SEQ ID NO 31
<211> LENGTH: 25
<212> TYPE: DNA
<213> ORGANISM: Artificial Sequence
<220> FEATURE:
<223> OTHER INFORMATION: C5L.1F primer

<400> SEQUENCE: 31
catcatgagc aacgcgttag tatat                                         25

<210> SEQ ID NO 32
<211> LENGTH: 21
<212> TYPE: DNA
<213> ORGANISM: Artificial Sequence
<220> FEATURE:
<223> OTHER INFORMATION: C5L.1R primer

<400> SEQUENCE: 32
ttagaaatta tgcattttag a                                             21

<210> SEQ ID NO 33
<211> LENGTH: 25
<212> TYPE: DNA
<213> ORGANISM: Artificial Sequence
<220> FEATURE:
<223> OTHER INFORMATION: C5L.2R primer

<400> SEQUENCE: 33
ggagatacct ttagatatgg atctg                                         25

<210> SEQ ID NO 34
<211> LENGTH: 25
<212> TYPE: DNA
<213> ORGANISM: Artificial Sequence
<220> FEATURE:
<223> OTHER INFORMATION: C5L.3R primer

<400> SEQUENCE: 34
ttgtaaccat agtatatctt agcgc                                         25

<210> SEQ ID NO 35
<211> LENGTH: 25
<212> TYPE: DNA
<213> ORGANISM: Artificial Sequence
<220> FEATURE:
<223> OTHER INFORMATION: 7634CXL-F primer

<400> SEQUENCE: 35
gttctcgtag gagagaacta ttgac                                         25
```

```
<210> SEQ ID NO 36
<211> LENGTH: 27
<212> TYPE: DNA
<213> ORGANISM: Artificial Sequence
<220> FEATURE:
<223> OTHER INFORMATION: 7635CXL-R primer

<400> SEQUENCE: 36
cgtcttcagc tgtaaacaaa tataatg                                          27

<210> SEQ ID NO 37
<211> LENGTH: 25
<212> TYPE: DNA
<213> ORGANISM: Artificial Sequence
<220> FEATURE:
<223> OTHER INFORMATION: CP65.1F primer

<400> SEQUENCE: 37
atggttcctc aggctctcct gtttg                                            25

<210> SEQ ID NO 38
<211> LENGTH: 25
<212> TYPE: DNA
<213> ORGANISM: Artificial Sequence
<220> FEATURE:
<223> OTHER INFORMATION: CP65.1R primer

<400> SEQUENCE: 38
tcacagtctg gtctcacccc cactc                                            25

<210> SEQ ID NO 39
<211> LENGTH: 20
<212> TYPE: DNA
<213> ORGANISM: Artificial Sequence
<220> FEATURE:
<223> OTHER INFORMATION: CP65.2R primer

<400> SEQUENCE: 39
gacccatgtt ccatccataa                                                  20

<210> SEQ ID NO 40
<211> LENGTH: 22
<212> TYPE: DNA
<213> ORGANISM: Artificial Sequence
<220> FEATURE:
<223> OTHER INFORMATION: CP65.3F primer

<400> SEQUENCE: 40
gtctcacccc cactcttgtg tg                                               22

<210> SEQ ID NO 41
<211> LENGTH: 20
<212> TYPE: DNA
<213> ORGANISM: Artificial Sequence
<220> FEATURE:
<223> OTHER INFORMATION: CP65.4F primer

<400> SEQUENCE: 41
gaaaacggta gacgggtctg                                                  20

<210> SEQ ID NO 42
<211> LENGTH: 23
<212> TYPE: DNA
<213> ORGANISM: Artificial Sequence
<220> FEATURE:
<223> OTHER INFORMATION: C3R.1F primer
```

```
<400> SEQUENCE: 42
catagcttta tgtaaaggag tat                                              23

<210> SEQ ID NO 43
<211> LENGTH: 20
<212> TYPE: DNA
<213> ORGANISM: Artificial Sequence
<220> FEATURE:
<223> OTHER INFORMATION: C3R.2F primer

<400> SEQUENCE: 43
tgtaatgggg ttttacctaa                                                  20

<210> SEQ ID NO 44
<211> LENGTH: 22
<212> TYPE: DNA
<213> ORGANISM: Artificial Sequence
<220> FEATURE:
<223> OTHER INFORMATION: C3R.3F primer

<400> SEQUENCE: 44
gctttatgaa gaggaggatt tt                                               22

<210> SEQ ID NO 45
<211> LENGTH: 20
<212> TYPE: DNA
<213> ORGANISM: Artificial Sequence
<220> FEATURE:
<223> OTHER INFORMATION: C3R.4F primer

<400> SEQUENCE: 45
gcattcagca gaacatttct                                                  20

<210> SEQ ID NO 46
<211> LENGTH: 20
<212> TYPE: DNA
<213> ORGANISM: Artificial Sequence
<220> FEATURE:
<223> OTHER INFORMATION: C3L.1F primer

<400> SEQUENCE: 46
tagttactct cgtatggcgt                                                  20

<210> SEQ ID NO 47
<211> LENGTH: 21
<212> TYPE: DNA
<213> ORGANISM: Artificial Sequence
<220> FEATURE:
<223> OTHER INFORMATION: C3L.1R primer

<400> SEQUENCE: 47
atcagtaacg tatagcatac g                                                21

<210> SEQ ID NO 48
<211> LENGTH: 25
<212> TYPE: DNA
<213> ORGANISM: Artificial Sequence
<220> FEATURE:
<223> OTHER INFORMATION: C3L.2R primer

<400> SEQUENCE: 48
tacatatttc taatgttaac atatt                                            25

<210> SEQ ID NO 49
```

```
<211> LENGTH: 20
<212> TYPE: DNA
<213> ORGANISM: Artificial Sequence
<220> FEATURE:
<223> OTHER INFORMATION: I3L.1F primer

<400> SEQUENCE: 49
ggatccctcg agatgagata                                             20

<210> SEQ ID NO 50
<211> LENGTH: 25
<212> TYPE: DNA
<213> ORGANISM: Artificial Sequence
<220> FEATURE:
<223> OTHER INFORMATION: RabG.PF primer

<400> SEQUENCE: 50
atagcttgta tgctttttat ttgat                                       25

<210> SEQ ID NO 51
<211> LENGTH: 25
<212> TYPE: DNA
<213> ORGANISM: Artificial Sequence
<220> FEATURE:
<223> OTHER INFORMATION: RabG.PR primer

<400> SEQUENCE: 51
gaacagcagg gcctggggca ccatg                                       25

<210> SEQ ID NO 52
<211> LENGTH: 20
<212> TYPE: DNA
<213> ORGANISM: Artificial Sequence
<220> FEATURE:
<223> OTHER INFORMATION: RabG.1F primer

<400> SEQUENCE: 52
gtgaaaacca ccaaggagtc                                             20

<210> SEQ ID NO 53
<211> LENGTH: 20
<212> TYPE: DNA
<213> ORGANISM: Artificial Sequence
<220> FEATURE:
<223> OTHER INFORMATION: RabG.1R primer

<400> SEQUENCE: 53
ttctgttcac cctccggcag                                             20

<210> SEQ ID NO 54
<211> LENGTH: 25
<212> TYPE: DNA
<213> ORGANISM: Artificial Sequence
<220> FEATURE:
<223> OTHER INFORMATION: RabG.2R primer

<400> SEQUENCE: 54
tggtgaagat gtcgcagctc atgcc                                       25

<210> SEQ ID NO 55
<211> LENGTH: 20
<212> TYPE: DNA
<213> ORGANISM: Artificial Sequence
<220> FEATURE:
<223> OTHER INFORMATION: RabG.2F primer

<400> SEQUENCE: 55
```

```
accaccaaga gcgtgtcctt                                               20

<210> SEQ ID NO 56
<211> LENGTH: 22
<212> TYPE: DNA
<213> ORGANISM: Artificial Sequence
<220> FEATURE:
<223> OTHER INFORMATION: RabG.3F primer

<400> SEQUENCE: 56
ttcctgatga cctgctgccg ga                                            22

<210> SEQ ID NO 57
<211> LENGTH: 20
<212> TYPE: DNA
<213> ORGANISM: Artificial Sequence
<220> FEATURE:
<223> OTHER INFORMATION: C6R.1F primer

<400> SEQUENCE: 57
gttctaaagt tctttcctcc                                               20

<210> SEQ ID NO 58
<211> LENGTH: 23
<212> TYPE: DNA
<213> ORGANISM: Artificial Sequence
<220> FEATURE:
<223> OTHER INFORMATION: C6R.2F primer

<400> SEQUENCE: 58
tctttcatat cttgtagata aga                                           23

<210> SEQ ID NO 59
<211> LENGTH: 20
<212> TYPE: DNA
<213> ORGANISM: Artificial Sequence
<220> FEATURE:
<223> OTHER INFORMATION: C6R.3F primer

<400> SEQUENCE: 59
tgaaggggtt gatggaataa                                               20

<210> SEQ ID NO 60
<211> LENGTH: 25
<212> TYPE: DNA
<213> ORGANISM: Artificial Sequence
<220> FEATURE:
<223> OTHER INFORMATION: C6L.1R primer

<400> SEQUENCE: 60
ctatcaaaag tcttaatgag ttagg                                         25

<210> SEQ ID NO 61
<211> LENGTH: 25
<212> TYPE: DNA
<213> ORGANISM: Artificial Sequence
<220> FEATURE:
<223> OTHER INFORMATION: OX40L.1F primer

<400> SEQUENCE: 61
atggaaggag tacaaccatt agatc                                         25

<210> SEQ ID NO 62
<211> LENGTH: 25
<212> TYPE: DNA
```

<213> ORGANISM: Artificial Sequence
<220> FEATURE:
<223> OTHER INFORMATION: C5R.1R primer

<400> SEQUENCE: 62
ttaataagca caaatccac cagga                                    25

<210> SEQ ID NO 63
<211> LENGTH: 183
<212> TYPE: PRT
<213> ORGANISM: Felis catus

<400> SEQUENCE: 63

Met Glu Gly Val Gln Pro Leu Asp Glu Asn Val Gly Asn Ala Pro Gly
1               5                   10                  15

Arg Arg Phe Gln Ser Asn Lys Leu Leu Leu Val Thr Ala Val Ile Gln
            20                  25                  30

Gly Leu Gly Leu Leu Leu Cys Phe Thr Tyr Ile Cys Leu His Phe Tyr
        35                  40                  45

Ala Ser Gln Val Pro Pro Gln Tyr Pro Pro Ile Gln Ser Ile Lys Val
    50                  55                  60

Gln Phe Thr Lys Cys Gly Asn Gly Thr Gly Cys Ile Ile Thr Ser Pro
65                  70                  75                  80

Asn Lys Asp Glu Thr Met Lys Val Gln Asp Asn Ser Ile Ile Ile Asn
                85                  90                  95

Cys Asp Gly Phe Tyr Leu Ile Ser Leu Lys Gly Tyr Phe Ser Glu Glu
            100                 105                 110

Leu Ser Leu Ser Leu Tyr Tyr Arg Lys Gly Arg Lys Pro Leu Phe Ser
        115                 120                 125

Leu Ser Lys Val Lys Ser Val Asp Ser Ile Gly Val Ala His Leu Ala
    130                 135                 140

Phe Lys Asp Lys Val Tyr Phe Asn Val Thr Thr His Asn Thr Ser Tyr
145                 150                 155                 160

Lys Asp Ile Gln Val Asn Gly Gly Glu Leu Ile Val Ile Leu Gln Asn
                165                 170                 175

Pro Gly Gly Phe Cys Val Leu
            180

<210> SEQ ID NO 64
<211> LENGTH: 183
<212> TYPE: PRT
<213> ORGANISM: Equus caballus

<400> SEQUENCE: 64

Met Glu Gly Val Gln Pro Leu Glu Glu Asn Val Gly Asn Thr Pro Gly
1               5                   10                  15

Arg Arg Phe Gln Arg Asn Lys Leu Leu Leu Val Thr Ser Ile Ile Gln
            20                  25                  30

Gly Leu Gly Leu Leu Leu Cys Leu Thr Tyr Val Cys Leu His Phe Tyr
        35                  40                  45

Thr Ser Gln Val Pro Ser Gln Tyr Pro Pro Ile Gln Ser Ile Arg Val
    50                  55                  60

Gln Phe Thr Ser Cys Glu Asn Glu Lys Gly Phe Ile Ile Thr Ser Pro
65                  70                  75                  80

Asn Gln Asp Glu Ile Met Lys Val Gln Asp Asn Ser Ile Ile Ile Asn
                85                  90                  95

Cys Asp Gly Phe Tyr Leu Ile Ser Leu Lys Gly Tyr Phe Ser Gln Glu

```
                    100                 105                 110
Leu Ser Leu Ser Leu His Tyr Arg Lys Gly Arg Glu Pro Leu Ser Ser
            115                 120                 125

Leu Ser Lys Val Arg Ser Val Asn Ser Ile Met Val Ala Tyr Leu Ala
            130                 135                 140

Phe Lys Asp Lys Val Tyr Leu Asn Val Thr Thr His Asn Thr Ser Cys
145                 150                 155                 160

Asp Asp Ile Gln Val Asn Gly Gly Glu Leu Ile Leu Ile His Gln Asn
                165                 170                 175

Pro Gly Gly Phe Cys Ala Tyr
            180

<210> SEQ ID NO 65
<211> LENGTH: 182
<212> TYPE: PRT
<213> ORGANISM: Bos taurus

<400> SEQUENCE: 65

Met Glu Gly Val Gln Pro Leu Asp Glu Asn Val Gly Asn Val Pro Gly
1               5                   10                  15

Arg Arg Phe Leu Arg Asn Lys Leu Leu Leu Val Ala Ser Ile Ile Gln
            20                  25                  30

Gly Leu Gly Leu Leu Leu Cys Leu Thr Tyr Ile Cys Leu His Phe Tyr
        35                  40                  45

Ala Gln Val Pro Ser Gln Tyr Pro Pro Ile Gln Ser Ile Arg Val Gln
    50                  55                  60

Phe Thr Lys Cys Glu Asn Glu Asn Gly Phe Ile Thr Ser Pro Asp
65                  70                  75                  80

Ala Asp Gly Thr Met Lys Val Gln Asn Asn Ser Ile Ile Ile Thr Cys
                85                  90                  95

Asp Gly Phe Tyr Leu Ile Ser Leu Lys Gly Tyr Phe Ser Gln Glu Leu
            100                 105                 110

Ser Leu Arg Leu Leu Tyr Arg Lys Gly Arg Glu Pro Leu Phe Ser Leu
            115                 120                 125

Asn Met Val Lys Ile Val Asp Ser Val Thr Val Ala Tyr Leu Arg Phe
            130                 135                 140

Lys Asp Lys Val Tyr Leu Asn Met Thr Thr Gln Asn Ala Ser Cys Glu
145                 150                 155                 160

Asp Ile Gln Val Asn Gly Gly Glu Leu Ile Leu Ile His Gln Asn Pro
                165                 170                 175

Gly Gly Phe Cys Val Tyr
            180

<210> SEQ ID NO 66
<211> LENGTH: 182
<212> TYPE: PRT
<213> ORGANISM: sus scrofa

<400> SEQUENCE: 66

Met Glu Gly Val Gln Pro Leu Asp Glu Asn Val Gly Asn Ala Pro Gly
1               5                   10                  15

Arg Arg Leu Leu Arg Asn Lys Leu Leu Leu Val Ala Ser Val Ile Gln
            20                  25                  30

Gly Leu Gly Leu Leu Leu Cys Leu Thr Tyr Ile Cys Leu His Leu Tyr
        35                  40                  45

Ala Gln Val Pro Ser Gln Tyr Pro Pro Ile Gln Ser Ile Lys Val Gln
```

```
                50              55              60
Phe Thr Lys Cys Glu Asn Asp Asn Gly Phe Ile Ile Thr Pro Ser Ser
 65                  70                  75                  80

Lys Asp Gly Thr Met Lys Val Gln Asn Asn Ser Ile Ile Ile Asn Cys
                 85                  90                  95

Asp Gly Phe Tyr Leu Ile Ser Leu Lys Gly Tyr Phe Ser Gln Glu Leu
            100                 105                 110

Ser Leu Met Leu Gln Tyr Arg Lys Gly Arg Lys Pro Leu Phe Ser Leu
        115                 120                 125

Asn Lys Val Lys Ser Val Asp Ser Val Thr Val Ala Asp Leu Ala Phe
130                 135                 140

Lys Asp Lys Val Phe Leu Asn Val Thr Thr His Ser Ala Ser Cys Glu
145                 150                 155                 160

Asp Ile Gln Val Asn Gly Gly Glu Leu Ile Leu Ile His Gln Asn Pro
                165                 170                 175

Gly Gly Phe Cys Val Tyr
            180

<210> SEQ ID NO 67
<211> LENGTH: 183
<212> TYPE: PRT
<213> ORGANISM: pan troglodytes

<400> SEQUENCE: 67

Met Glu Arg Val Gln Pro Leu Glu Glu Asn Val Gly Asn Ala Ala Arg
  1               5                  10                  15

Pro Arg Phe Glu Arg Asn Lys Leu Leu Leu Val Ala Ser Val Ile Gln
             20                  25                  30

Gly Leu Gly Leu Leu Leu Cys Phe Thr Tyr Ile Cys Leu His Phe Ser
         35                  40                  45

Ala Leu Gln Val Ser His Arg Tyr Pro Arg Ile Gln Ser Ile Lys Val
     50                  55                  60

Gln Phe Thr Glu Tyr Lys Lys Glu Lys Gly Phe Ile Leu Thr Ser Gln
 65                  70                  75                  80

Lys Glu Asp Glu Val Met Lys Val Gln Asn Asn Ser Val Ile Ile Asn
                 85                  90                  95

Cys Asp Gly Phe Tyr Leu Ile Ser Leu Lys Gly Tyr Phe Ser Gln Glu
            100                 105                 110

Val Asn Ile Ser Leu His Tyr Gln Lys Asp Glu Glu Pro Leu Phe Gln
        115                 120                 125

Leu Lys Lys Val Arg Ser Val Asn Ser Leu Met Val Ala Ser Leu Thr
130                 135                 140

Tyr Lys Asp Lys Val Tyr Leu Asn Val Thr Thr Asp Asn Thr Ser Leu
145                 150                 155                 160

Asp Asp Phe His Val Asn Gly Gly Glu Leu Ile Leu Ile His Gln Asn
                165                 170                 175

Pro Gly Glu Phe Cys Val Leu
            180

<210> SEQ ID NO 68
<211> LENGTH: 5049
<212> TYPE: DNA
<213> ORGANISM: Artificial Sequence
<220> FEATURE:
<223> OTHER INFORMATION: Plasmid p397-cOX40L (pC6 42Kp cOX40L)

<400> SEQUENCE: 68
```

-continued

```
ggaaattgta aacgttaata ttttgttaaa attcgcgtta aatttttgtt aaatcagctc    60 atttttaac  caataggccg aaatcggcaa atcccttat  aaatcaaaag aatagaccga   120 gataggttg  agtgttgttc cagtttggaa caagagtcca ctattaaaga acgtggactc   180
caacgtcaaa gggcgaaaaa ccgtctatca gggcgatggc ccactacgtg aaccatcacc   240
ctaatcaagt tttttggggt cgaggtgccg taaagcacta atcggaacc  ctaaagggag   300 cccccgattt agagcttgac ggggaaagcc ggcgaacgtg gcgagaaagg aagggaagaa   360
agcgaaagga gcgggcgcta gggcgctggc aagtgtagcg gtcacgctgc gcgtaaccac   420
cacacccgcc gcgcttaatg cgccgctaca gggcgcgtcg cgccattcgc cattcaggct   480
gcgcaactgt tgggaagggc gatcggtgcg ggcctcttcg ctattacgcc agctggcgaa   540
agggggatgt gctgcaaggc gattaagttg ggtaacgcca gggttttccc agtcacgacg   600
ttgtaaaacg acggccagtg aattgtaata cgactcacta tagggcgaat gggtaccttt   660
cataaataca agtttgatta aacttaagtt gttctaaagt tctttcctcc gaaggtatag   720
aacaaagtat ttcttctaca tccttactat ttattgcagc ttttaacagc ctatcacgta   780 tcctatttt  agtattggta gaacgtttta gttctaaagt taaaatatta gacataattg   840
gcatattgct tattccttgc atagttgagt ctgtagatcg tttcagtata tcactgatta   900
atgtactact gttatgatga aatatagaat cgatattggc atttaactgt tttgttatac   960
taagtctaga ttttaaatct tctagtaata tgctatttaa tataaaagct tccacgtttt  1020
tgtatacatt tctttccata ttagtagcta ctactaaatg attatcttct ttcatatctt  1080
gtagataaga tagactatct ttatctttat tagtagaaaa tacttctggc catacatcgt  1140
taaatttttt tgttgttgtt agatataata ttaaatatct agaggatcct attatttgtg  1200
gtaaaatgtt tatagagtaa aatgatctgg ctattaaaca taggccagtt accatagaat  1260
gctgcttccc gttacagtgt tttaccataa ccatagatct gcctgtattg ttgatacata  1320
taacagctgt aaatcctaaa aaattcctat cataattatt aatattaggt aattcatttc  1380
catgtgaaag atagactaat tttatatcct ttacctccaa ataattattt acatctctta  1440
aacaatctat tttaatatca ttaactggta ttttataata tccagaaagg tttgaagggg  1500
ttgatggaat aagtctatta acatcgttaa gtaaattatt aatatcatga atctttatta  1560
tattataccc ataagttaaa tttatattta ctttctcatc atctgactta gttagtttgt  1620
aataaggtgt gtctgaaaaa attaaaaggt aattcgttga atgaagctgt atttgctgta  1680
tcatttttat ctaattttgg agatttagca gtacttactt cattagaaga agaatctgcc  1740
agttcctgtc tattactgat atttcgtttc attattatat gatttatatt ttacttttc   1800 aattatatat actcatttga ctagttaatc aataaaaaga attctcaaaa ttgaaaatat  1860
ataattacaa tataaaatgg aaggagtaca accattagat caaaatgttg gaaatacacc  1920
aggaagaaga tttcaaaaaa ataaagtatt attagtagca gcaataattc aaggtttagg  1980
attattatta tgttttacat atatatgttt acactttat  gcatctcaag taccacctca  2040
atatccacct atacaaagta taagagttca gttacaagaa tgtgaaaatg aaaaaggttg  2100
tattattaca tctccaagta aagatgaaac tatgaaagta caagataatt caataatcat  2160
aaattgtgat ggttttttact taattagttt aaaaggatat ttttcagaag aattatcatt  2220
atctttatat tatagaaaag gtagaggacc tttattttct ttatcaaaag taacatcagt  2280
tgattctatt ggagttgcat atttggcttt taaagataaa gtatatttta atgttacaac  2340
```

```
tcattctact agttataaag atatacaagt aaatggtggt gaattaatat taatacatca   2400
aaatcctggt ggattttgtg cttattaatt tttatcccgg ttttttatag ctaattagtc   2460
atttttcgta agtaagtatt tttatttaat acttttttatt gtacttatgt taaatataac   2520
tgatgataac aaaatccatt atgtattatt tataactgta atttctttag cgtagttaga   2580
tgtccaatct ctctcaaata catcggctat cttttttagtg agattttgat ctatgcagtt   2640
gaaacttatg aacgcgtgat gattaaaatg tgaaccgtcc aaatttgcag tcattatatg   2700
agcgtatcta ttatctacta tcatcatctt tgagttatta atatcatcta ctttagaatt   2760
gataggaaat atgaatacct ttgtagtaat atctatacta tctacaccta actcattaag   2820
acttttgata ggcggccgcg agctccagct tttgttccct ttagtgaggg ttaattccga   2880
gcttggcgta atcatggtca tagctgtttc ctgtgtgaaa ttgttatccg ctcacaattc   2940
cacacaacat acgagccgga agcataaagt gtaaagcctg gggtgcctaa tgagtgagct   3000
aactcacatt aattgcgttg cgctcactgc ccgctttcca gtcgggaaac ctgtcgtgcc   3060
agctgcatta atgaatcggc caacgcgcgg ggagaggcgg tttgcgtatt gggcgctctt   3120
ccgcttcctc gctcactgac tcgctgcgct cggtcgttcg gctgcggcga gcggtatcag   3180
ctcactcaaa ggcggtaata cggttatcca cagaatcagg gataacgca ggaaagaaca   3240 tgtgagcaaa aggccagcaa aaggccagga accgtaaaaa ggccgcgttg ctggcgtttt   3300
tccataggct ccgcccccct gacgagcatc acaaaaatcg acgctcaagt cagaggtggc   3360
gaaacccgac aggactataa agataccagg cgtttccccc tggaagctcc ctcgtgcgct   3420
ctcctgttcc gaccctgccg cttaccggat acctgtccgc ctttctccct cgggaagcg   3480 tggcgctttc tcatagctca cgctgtaggt atctcagttc ggtgtaggtc gttcgctcca   3540
agctgggctg tgtgcacgaa ccccccgttc agcccgaccg ctgcgcctta ccggtaact   3600 atcgtcttga gtccaacccg gtaagacacg acttatcgcc actggcagca gccactggta   3660
acaggattag cagagcgagg tatgtaggcg gtgctacaga gttcttgaag tggtggccta   3720
actacggcta cactagaagg acagtatttg gtatctgcgc tctgctgaag ccagttacct   3780
tcggaaaaag agttggtagc tcttgatccg gcaaacaaac caccgctggt agcggtggtt   3840
tttttgtttg caagcagcag attacgcgca gaaaaaaagg atctcaagaa gatcctttga   3900
tcttttctac ggggtctgac gctcagtgga acgaaaactc acgttaaggg attttggtca   3960
tgagattatc aaaaaggatc ttcacctaga tccttttaaa ttaaaaatga agttttaaat   4020
caatctaaag tatatatgag taaacttggt ctgacagtta ccaatgctta atcagtgagg   4080
cacctatctc agcgatctgt ctatttcgtt catccatagt tgcctgactc cccgtcgtgt   4140
agataactac gatacgggag ggcttaccat ctggccccag tgctgcaatg ataccgcgag   4200
acccacgctc accggctcca gatttatcag caataaacca gccagccgga agggccgagc   4260
gcagaagtgg tcctgcaact ttatccgcct ccatccagtc tattaattgt tgccgggaag   4320
ctagagtaag tagttcgcca gttaatagtt tgcgcaacgt tgttgccatt gctacaggca   4380
tcgtggtgtc acgctcgtcg tttggtatgg cttcattcag ctccggttcc caacgatcaa   4440
ggcgagttac atgatccccc atgttgtgca aaaaagcggt tagctccttc ggtcctccga   4500
tcgttgtcag aagtaagttg gccgcagtgt tatcactcat ggttatggca gcactgcata   4560
attctcttac tgtcatgcca tccgtaagat gcttttctgt gactggtgag tactcaacca   4620
agtcattctg agaatagtgt atgcggcgac cgagttgctc ttgcccggcg tcaatacggg   4680
ataataccgc gccacatagc agaactttaa aagtgctcat cattggaaaa cgttcttcgg   4740
```

```
ggcgaaaaact ctcaaggatc ttaccgctgt tgagatccag ttcgatgtaa cccactcgtg    4800
cacccaactg atcttcagca tcttttactt tcaccagcgt ttctgggtga gcaaaaacag    4860
gaaggcaaaa tgccgcaaaa aagggaataa gggcgacacg gaaatgttga atactcatac    4920
tcttcctttt tcaatattat tgaagcattt atcagggtta ttgtctcatg agcggataca    4980
tatttgaatg tatttagaaa aataaacaaa tagggggttcc gcgcacattt ccccgaaaag    5040
tgccacctg                                                             5049

<210> SEQ ID NO 69
<211> LENGTH: 7865
<212> TYPE: DNA
<213> ORGANISM: Artificial Sequence
<220> FEATURE:
<223> OTHER INFORMATION: Plasmid p397-Syn Rabies G (pC3 I3Lp Syn Rabies
      G)

<400> SEQUENCE: 69
agcttggcgt aatcatggtc atagctgttt cctgtgtgaa attgttatcc gctcacaatt      60
ccacacaaca tacgagccgg aagcataaag tgtaaagcct ggggtgccta atgagtgagc     120
taactcacat taattgcgtt gcgctcactg cccgctttcc agtcgggaaa cctgtcgtgc     180
cagctgcatt aatgaatcgg ccaacgcgcg gggagaggcg gtttgcgtat tgggcgctct     240
tccgcttcct cgctcactga ctcgctgcgc tcggtcgttc ggctgcggcg agcggtatca     300
gctcactcaa aggcggtaat acggttatcc acagaatcag gggataacgc aggaaagaac     360
atgtgagcaa aaggccagca aaaggccagg aaccgtaaaa aggccgcgtt gctggcgttt     420
ttccataggc tccgcccccc tgacgagcat cacaaaaatc gacgctcaag tcagaggtgg     480
cgaaacccga caggactata aagataccag gcgtttcccc ctggaagctc cctcgtgcgc     540
tctcctgttc cgaccctgcc gcttaccgga tacctgtccg cctttctccc ttcgggaagc     600
gtggcgcttt ctcatagctc acgctgtagg tatctcagtt cggtgtaggt cgttcgctcc     660
aagctgggct gtgtgcacga accccccgtt cagcccgacc gctgcgcctt atccggtaac     720
tatcgtcttg agtccaaccc ggtaagacac gacttatcgc cactggcagc agccactggt     780
aacaggatta gcagagcgag gtatgtaggc ggtgctacag agttcttgaa gtggtggcct     840
aactacggct acactagaag gacagtattt ggtatctgcg ctctgctgaa gccagttacc     900
ttcggaaaaa gagttggtag ctcttgatcc ggcaaacaaa ccaccgctgg tagcggtggt     960
ttttttgttt gcaagcagca gattacgcgc agaaaaaaag gatctcaaga agatcctttg    1020
atcttttcta cggggtctga cgctcagtgg aacgaaaact cacgttaagg gattttggtc    1080
atgagattat caaaaaggat cttcacctag atccttttaa attaaaaatg aagttttaaa    1140
tcaatctaaa gtatatatga gtaaacttgg tctgacagtt accaatgctt aatcagtgag    1200
gcacctatct cagcgatctg tctatttcgt tcatccatag ttgcctgact ccccgtcgtg    1260
tagataacta cgatacggga gggcttacca tctggcccca gtgctgcaat gataccgcga    1320
gacccacgct caccggctcc agatttatca gcaataaacc agccagccgg aagggccgag    1380
cgcagaagtg gtcctgcaac tttatccgcc tccatccagt ctattaattg ttgccgggaa    1440
gctagagtaa gtagttcgcc agttaatagt ttgcgcaacg ttgttgccat tgctacaggc    1500
atcgtggtgt cacgctcgtc gtttggtatg gcttcattca gctccggttc ccaacgatca    1560
aggcgagtta catgatcccc catgttgtgc aaaaaagcgg ttagctcctt cggtcctccg    1620
atcgttgtca gaagtaagtt ggccgcagtg ttatcactca tggttatggc agcactgcat    1680
```

-continued

```
aattctctta ctgtcatgcc atccgtaaga tgcttttctg tgactggtga gtactcaacc   1740
aagtcattct gagaatagtg tatgcggcga ccgagttgct cttgcccggc gtcaatacgg   1800
gataataccg cgccacatag cagaacttta aaagtgctca tcattggaaa acgttcttcg   1860
gggcgaaaac tctcaaggat cttaccgctg ttgagatcca gttcgatgta acccactcgt   1920
gcacccaact gatcttcagc atcttttact ttcaccagcg tttctgggtg agcaaaaaca   1980
ggaaggcaaa atgccgcaaa aaagggaata agggcgacac ggaaatgttg aatactcata   2040
ctcttccttt ttcaatatta ttgaagcatt tatcagggtt attgtctcat gagcggatac   2100
atatttgaat gtatttagaa aaataaacaa ataggggttc cgcgcacatt tccccgaaaa   2160
gtgccacctg acgtctaaga accattatt atcatgacat taacctataa aaataggcgt   2220
atcacgaggc cctttcgtct cgcgcgtttc ggtgatgacg tgaaaacct ctgacacatg   2280
cagctcccgg agacggtcac agcttgtctg taagcggatg ccgggagcag acaagcccgt   2340
cagggcgcgt cagcgggtgt tggcgggtgt cggggctggc ttaactatgc ggcatcagag   2400
cagattgtac tgagagtgca ccatatgcgg tgtgaaatac cgcacagatg cgtaaggaga   2460
aaataccgca tcaggcgcca ttcgccattc aggctgcgca actgttggga agggcgatcg   2520
gtgcgggcct cttcgctatt acgccagctg gcgaaagggg gatgtgctgc aaggcgatta   2580
agttgggtaa cgccagggtt ttcccagtca cgacgttgta aaacgacggc cagtgaatta   2640
attcgagctc tttatactac tgggttacaa cagctggtga taacagaatg taaatcatta   2700
ttacttaata gttccattat tatatgtttg atatctatag gtaacctacc tattattcct   2760
agattcttac tctcttttac agctttaact attagctgat gtctatgaaa agctaatgat   2820
ttatttttcc gtattaattc cctatatata cgtatacatg caggtatctt attaactcta   2880
ggattagtta cgaactttac cataagatct atgttattgt caagaaagat attaaaagaa   2940
tatatagaat ttaactttat atgtgttata acatctagtt cttttttcgca tgattctttt   3000
atagatagta gtctttttatt actgtttata tgttccatgt ttactataaa accttctgaa   3060
ttagctattt caggatttttt agatatttct aacatcattt tagatattat cataatagct   3120
atcttgtcat ctaaaaagct aacacaagtt agaggcgtat taccgtgatt atttagaaa   3180
ttatagtcgg cgttataaga taaaagtaat tttatattat taaaactatt agataacata   3240
gctttatgta aaggagtatt tccagataac ttagctttag catttacgta agcaccgtgg   3300
tcaagtaaga gtttaacaaa ttctgttttc atagaactaa ctgccatgta tagaggagtg   3360
aaaccttat gattatagac gtttacatag caaccatata ataagatcgc attcagtata   3420
ttaatatctt tcatttctat agctatgtga ataacatgtt tatctaatcc taccaacttt   3480
gtatcagtac cgtacttcag taataagttt actatagttt tgttttttaga tgcaacagct   3540
atatttagaa cggtatctat atgattatta accacattaa cattagatcc tctttctaaa   3600
agtgtctttg ttgtttcgat atcgttacgt gaaacagcgt aatgtaaggg actgcccata   3660
cagtcatcta ttacgtttat atcagctcct agatttaaca gaagtgctgt tacatctttt   3720
cttctattaa ttaccgaatg atgtaatggg gttttaccta aatcatcttg ttcgtttata   3780
ggcactccgt gatttataag taacgctatt atatcgtaac tacaattatt tttaagtgcc   3840
tttatgagat actgtttatg caaaaataaa cttttatcta ttttaatact attatctaac   3900
aatatcctaa ttaaatctat attcttatac tttatagcgt aatgtaacgg agttccaaaa   3960
tttctagttt gtatattaag atcaatatta aaatctataa atatttttata catatcatca   4020
```

```
gatatcttat catacagtac atcgtaataa tttagaaaga atctattaca attaacacct      4080
ttttttaata aatatctagt taatgactta ttgtttctat atacagaaat atataacgga      4140
ctatttccag aatgtatctg ttctatgtca gcgccagaat ctattagtag tttagcaatt      4200
tctgtattat ctaaactagc agctttatga agaggaggat ttttacattt taaaatatcg      4260
gcaccgtgtt ctagtaataa ttttaccatt tctatatcag aaatacttac ggctaaatac      4320
aaagacgttg atagtatatt tacgttattg tatttgcatt ttttaagtat ataccttact      4380
aaatttatat ctctatacct tatagcttta tgcagttcat ttataagtct tccattactc      4440
atttctggta atgaagtatt atatatcatt atgatattat ctctatttta ttctaataaa      4500
aaccgttatc atgttatttta ttatttgtta taattatact atttaataaa ttataccaaa     4560
tacttagata cttattaata ccatcctaga acttgtattt cttgccccct aaacttggac      4620
atgcactcca ttaggcgttt cttgttttcg acatcgtcct ccttaacata tcctactgtt      4680
atgtgaggat tccacggatt atctactgtg atatcaccaa acacgtcctt cgaacagggt      4740
accgcattca gcagaacatt tcttagggct ctaagttcat cagatacctc cagtttcata      4800
actacagcgc atcctttcgc tcccaactgt ttagaggcgt tactctgagg aaaacacatc      4860
tcttctttac agactataga aatagtctgt aaatcttgat cagttatttg cttttttgaaa     4920 ttttcaaatc tatcacattg atccatattt gctattccaa gagttatatg aggaaaaata     4980
tcacatcctg tcatgtattt tattgtaaca ttattataat ctgtaacatc agtatctaac      5040
ctaacgtcgt aaaagttaac agatgcccag ttactataat cccaaggaac cttaacatct      5100
aatcccatta aaatagtatc ctttctacta ttttttttcat tggcaagtat gtggcttagt      5160
ttacacaaaa ttcctgccat tttgtaacga tagcgaagca atagcttgta tgcttttat      5220 ttgattaact agtcataaaa atcgggatcc ctcgagatga gataaagtga aaatatatat     5280
cattatatta caaagtacaa ttatttaggt ttaatcatgg tgccccaggc cctgctgttc      5340
gtgcccctgc tggtgttccc cctgtgcttc ggcaagttcc ccatctacac catccccgac      5400
aagctgggcc cctggagccc catcgacatc caccacctga gctgcccaa caatctggtg      5460 gtggaggatg agggctgcac caatctgagc ggcttcagct acatggagct gaaagtgggc      5520
tacatcctgg ccatcaagat gaacggcttc acctgcaccg gcgtggtgac cgaggccgag      5580
acctacacca actttgtggg ctacgtgacc accaccttca gcggaagca cttcagacct      5640 accccgacg cctgcagagc cgcctacaac tggaagatgg ccggcgaccc tagatacgag      5700
gagagcctgc acaacccta ccccgactac agatggctgc ggaccgtgaa aaccaccaag      5760
gagtccctgg tgatcatcag ccctagcgtg gccgatctgg acccctacga cagaagcctg      5820
cacagcagag tgttccctag cggcaagtgc agcggcgtgg ccgtgtccag cacctactgc      5880
agcaccaacc acgactacac catctggatg cccgagaacc tagactggg catgagctgc      5940 gacatcttca ccaacagccg gggcaagaga gccagcaagg gcagcgagac ctgcggcttc      6000
gtggacgaga gaggcctgta caagagcctg aagggcgcct gcaagctgaa gctgtgcggc      6060
gtgctgggcc tgagactgat ggacggcacc tgggtggcca tgcagaccag caacgagacc      6120
aagtggtgcc ctcctgacca gctggtgaac ctgcacgact ccggagcga tgagatcgag      6180 cacctggtgg tggaagagct ggtgcggaag agagaggagt gcctggacgc cctggagagc      6240
atcatgacca ccaagagcgt gtccttccgg agactgagcc acctgagaaa gctggtgccc      6300
ggctttggca aggcctacac aatcttcaac aagaccctga tggaggccga tgcccactac      6360
aagtctgtgc ggacctggaa cgagatcctg cctagcaagg gctgcctgag agtgggcggc      6420
```

```
agatgccacc cccacgtgaa cggcgtgttc ttcaacggca tcatcctggg ccctgacggc    6480
aacgtgctga tccctgagat gcagagcagc ctgctgcagc agcacatgga actgctggag    6540
agcagcgtga tccccctggt gcacccctg gccgacccca gcaccgtgtt caaggatggc    6600
gacgaggccg aggacttcgt ggaggtgcac ctgcccgatg tgcacaacca ggtgtccggc    6660
gtggacctgg gcctgcccaa ctggggcaag tacgtgctgc tgagcgccgg agccctgacc    6720
gccctgatgc tgatcatctt cctgatgacc tgctgccgga gggtgaacag aagcgagccc    6780
acccagcaca acctgagagg caccggcaga gaggtgtccg tgaccccca gagcggcaag    6840 atcatcagca gctgggagag ccacaagagc ggcggagaga ccagactatg attttttatgc    6900 ccgggttttt atagctaatt agtcaaatgt gagttaatat tagtatacta cattactaat    6960
ttattacata ttcatttata tcaatctagt agcatttagc tttataaaa caatataact    7020 gaatagtaca tactttacta ataagttata aataagagat acatatttat agtattttac    7080 tttctcacact gaataataata atataattat acaaatataa ttttaatac tatatagtat    7140 ataactgaaa taaaatacca gtgtaatata gttattatac atttatacca catcaaagat    7200
gagttataac atcagtgtca ctgttagcaa cagtagttat acgatgagta gttactctcg    7260
tatggcgtta gtatgtatgt atcttctagt tttcttagta ggcattatag gaaacgtcaa    7320
gcttataagg ttattaatgg tatctagaaa tatatctatt ataccgtttc tcaacttggg    7380
aatagccgat ttgctgtttg tgatattcat acctttatac attatataca tactaagtaa    7440
tttccattgg catttggta aagcactttg taaaattagt tctttcttttt ttacttctaa    7500 catgtttgca agtatatttt taataactgt aataagcgta tatagatatg taaaaattac    7560
ccttcctgga tttacctata aatatgttaa cattagaaat atgtacatta ctatatttttt    7620 catatggatt atttctatta tactagggat tcctgctctt tactttagaa atactatcgt    7680
aacaaaaaat aacgacacgc tgtgtattaa tcattatcat gataatagag aaattgctga    7740
attgatttac aaagttatta tctgtatcag atttattttta ggatacctac tacctacgat    7800
aattatactc gtatgctata cgttactgat ctacagaact aacaatgcat gtcgacgcgg    7860
ccgca                                                                7865
```

<210> SEQ ID NO 70
<211> LENGTH: 235
<212> TYPE: PRT
<213> ORGANISM: Gallus gallus

<400> SEQUENCE: 70

```
Met Met Val Cys Ala Ser Ala Ser Thr Lys Gln Ala Arg Pro Ala Gly
1               5                   10                  15

Asp Cys Gly Pro Pro Val Leu Leu Val Pro Ala Leu Leu Val Glu Met
            20                  25                  30

Glu Gly Gln Pro Asp Thr Glu Leu Lys Lys His Thr Asp Gln Lys Asp
        35                  40                  45

Cys Glu Lys Glu Pro Ala Gly Met Arg Ser Asp Asp Glu Trp Arg Gly
    50                  55                  60

Trp Gln Lys Gly Gln Ala Lys Arg Asn Thr Leu Tyr Leu Val Ser Ala
65                  70                  75                  80

Ala Thr Gln Trp Ile Leu Leu Ala Cys Leu Ile Tyr Leu Gly Thr
                85                  90                  95

Asp Ser Leu Gln Leu Trp Thr Pro His Ser Asp Lys Val Lys Trp Thr
            100                 105                 110
```

Tyr Ile Arg Tyr Thr Gly Gln Ser Ile Ala Gly Val Ala Met Asn Leu
            115                 120                 125

Ser Ala Glu Phe Thr Ser Ile Pro Val Ile Asn Gly Ser Ile Met Ile
    130                 135                 140

Pro Cys Asp Gly Leu Tyr Val Val Ser Leu Lys Gly Val Leu Ser Pro
145                 150                 155                 160

Asp Leu Glu Lys Ser Ser Leu Lys Leu Met Met Lys Asn Thr Glu Ser
                165                 170                 175

Lys Asn Ala Ala Pro Leu Trp Glu Arg Asp Val Gln Asn Ser Ser Asn
            180                 185                 190

Ala Val Asp Leu Ile Thr Met Leu Tyr Leu Phe Ala Gln Asn Asn Ile
            195                 200                 205

Ile Leu Ser Thr Ser Ser Asn Ala Thr Ile Gln Cys Leu Thr Phe Ser
            210                 215                 220

Leu Val Leu Leu Asn Pro Val Phe Cys Asn Pro
225                 230                 235

<210> SEQ ID NO 71
<211> LENGTH: 181
<212> TYPE: PRT
<213> ORGANISM: Ovis aries

<400> SEQUENCE: 71

Met Glu Gly Val Gln Pro Leu Asp Glu Asn Val Gly Asn Ala Pro Gly
1               5                   10                  15

Arg Arg Phe Leu Arg Asn Lys Leu Leu Leu Val Ala Ser Ile Ile Gln
            20                  25                  30

Gly Leu Gly Leu Leu Leu Cys Leu Thr Tyr Ile Cys Leu His Phe Tyr
            35                  40                  45

Ala Gln Val Pro Ser Gln Tyr Pro Pro Ile Gln Ser Ile Arg Val Arg
    50                  55                  60

Phe Thr Cys Glu Asn Glu Asn Gly Phe Ile Ile Thr Ser Pro Asp Ala
65                  70                  75                  80

Asp Gly Thr Met Lys Val Gln Asn Asn Ser Ile Ile Thr Cys Asp
                85                  90                  95

Gly Phe Tyr Leu Ile Ser Leu Lys Gly Tyr Phe Ser Gln Lys Leu Ser
            100                 105                 110

Leu Arg Leu Leu Tyr Arg Lys Gly Arg Glu Pro Leu Phe Ser Leu Asn
            115                 120                 125

Met Val Lys Ile Val Asp Ser Val Thr Val Ala Tyr Leu Arg Phe Lys
    130                 135                 140

Asp Lys Val Tyr Leu Asn Val Thr Thr Gln Asn Ala Ser Cys Glu Asp
145                 150                 155                 160

Ile Gln Val Asn Gly Gly Glu Leu Ile Leu Ile His Gln Asn Pro Gly
                165                 170                 175

Gly Phe Cys Val Tyr
            180

RECOMBINANT POXVIRAL VECTORS EXPRESSING BOTH RABIES AND OX40 PROTEINS, AND VACCINES MADE THEREFROM

CROSS-REFERENCE TO OTHER APPLICATIONS

This application claims priority to U.S. provisional patent application 61/598,610, which was filed on Feb. 14, 2012, and is herein incorporated by reference in its entirety.

FIELD OF THE INVENTION

The present invention relates generally to viral vaccines and methods of using the same. More particularly, the present invention relates to viral vectors which may comprise one or more genetic adjuvants, resulting in enhanced immune response to an antigen expressed by a gene in a vector, advantageously a viral vector.

BACKGROUND

Rabies is a disease that can occur in all warm-blooded species and is caused by rabies virus. Infection with rabies virus followed by the outbreak of the clinical features in nearly all instances results in death of the infected species. Rabies virus is a non-segmented negative-stranded RNA virus of the Rhabdoviridae family. Rabies virus virions are composed of two major structural components: a nucleocapsid or ribonucleoprotein (RNP), and an envelope in the form of a bilayer membrane surrounding the RNP core. The infectious component of all Rhabdoviruses is the RNP core which consists of the RNA genome encapsidated by the nucleocapsid (N) protein in combination with two minor proteins, i.e. RNA-dependent RNA-polymerase (L) and phosphoprotein (P). The membrane surrounding the RNP core consists of two proteins: a trans-membrane glycoprotein (G) and a matrix (M) protein located at the inner site of the membrane.

The G protein, also referred to as spike protein, is responsible for cell attachment and membrane fusion in rabies virus and additionally is the main target for the host immune system. The amino acid region at position 330 to 340 (referred to as antigenic site III) of the G protein has been identified to be responsible for the virulence of the virus, in particular the Arg residue at position 333. All rabies virus strains have this virulence determining antigenic site III in common.

Conventional Rabies Vaccines for companion animals comprise inactivated rabies plus adjuvants, which are well-known in the art, are diverse in nature. Adjuvants may, for example, consist of water-insoluble inorganic salts, liposomes, micelles or emulsions, i.e. Freund's adjuvant. Other adjuvants may be found in Vogel and Powell, 1995, mentioned supra. Although there is no single mechanism of adjuvant action, an essential characteristic is their ability to significantly increase the immune response to a vaccine antigen as compared to the response induced by the vaccine antigen alone (Nossal, 1999, supra; Vogel and Powell, 1995, supra). In this regard, some adjuvants are more effective at augmenting humoral immune responses; other adjuvants are more effective at increasing cell-mediated immune responses (Vogel and Powell, 1995, supra); and yet another group of adjuvants increase both humoral and cell-mediated immune responses against vaccine antigens (Vogel and Powell, 1995, supra). In sum, adjuvants generally appear to exert their effects in at least one of five ways: 1) facilitate antigen uptake, transport and presentation in the lymph nodes, 2) prolong antigen presentation, 3) signal pathogen-recognition receptors (PRRs) expressed on innate immune cells, 4) cause damage or stress to cells, which signals an immune response, and 5) induce a preferential Th1 or Th2 response (Schijns V E et al. 2007). The immunogenicity of antigens may also be enhanced by the use of genetic adjuvants, such as ligands for receptor residing on immune cell membranes. Genetic adjuvants for DNA vaccines have been reviewed (see, e.g., Calarota & Weiner, Expert Rev Vaccines. 2004 August; 3(4 Suppl): S 135-49, Calarota & Weiner, Immunol Rev. 2004 June; 199:84-99 and Kutzler & Weiner, J Clin Invest. 2004 November; 1 14(9):1241-4), however genetic adjuvants for viral vaccines, especially for poxvirus-based viral vaccines, remain less well-studied.

Several members of tumor necrosis factor superfamily (TNFSF) and their corresponding receptors (TNFRSF) have been shown to provide critical costimulatory signals for immune response (Watts T H. Annu Rev Immunol 2005; 23:23-68). OX40 Ligand (OX40L), also known as gp34, CD252, CD134L or TNFSF4, is a member of the TNF superfamily. Human OX40L shares 46% amino acid sequence identity with its mouse counterpart. Similar to other TNF superfamily members, membrane-bound OX40 Ligand exists as a homotrimer. OX40L binds to OX40 (CD134), a member of the TNF receptor superfamily. OX40 is expressed on activated T cells, while its ligand, OX40L is induced on activated antigen-presenting cells (APCs), such as B cells, and dendritic cells (DCs) [Watts T H. 2005 supra, Sugamura K, et al., Nat Rev Immunol 2004; 4(6):420-31]. OX40-OX40L interaction can promote proliferation, differentiation, and especially survival of CD4+ T cells (Rogers P R, et al., Immunity 2001; 15(3):445-55; Song J, et al., Nat Immunol 2004; 5(2):150-8). Ligation of OX40 has been shown to enhance ex vivo human CD8+ T cell recall responses against viruses, including HIV-1, Epstein-Barr virus (EBV), and influenza virus (Serghides L, et al., J. Immunol. 2005; 175(10):6368-77;). Co-immunization of mice with OX40L-expressing canarypox and HIV-1 canarypox vaccine, vCP1452, augmented HIV-1 specific CD8+ T cell responses in terms of frequency and cytokine expression (Liu J. et al., Vaccine. 2009; 275077-5084). However, OX40L did not enhance antibody responses elicited by the HIV-1 canarypox vaccine, suggesting that, canarypox vectors expressing OX40L can enhance the cellular but not humoral immunogenicity of HIV-1 canarypox vaccines. Liu J. et al., 2009, supra).

In the instant disclosure, the OX40L is co-expressed together with rabies G by the same recombinant as opposed to previous works by Serghides L, et al., 2005, supra, where adenovirus-expressed OX40L was used in combination with influenza peptides in an in vitro studies or the work described by Liu J. et al., 2009, where OX40L-expressing canarypox and HIV-1 expressing canarypox were co-administered. Surprisingly, this co-expression of OX40L resulted in 2- to 3-fold increase in peak anti-rabies neutralizing antibody titers as opposed to absence of improvement in humoral immunogenicity in the work reported by Liu J. et al., 2009, supra.

A genetically-adjuvanted Rabies vaccine for companion animals would be highly desirable, as it could avoid or reduce the negative consequences currently associated with conventional chemically adjuvanted vaccines (e.g. injection site reactions, discomfort, pain, non-specific immune responses, increased cancer risk etc.). For example, in cats, vaccine-associated sarcomas have been reported to develop in association with administration of some adjuvanted vaccines. Thus, there is a need for an effective and safe viral vaccine, especially with respect to expression of a target antigen, epitope, immunogen, peptide or polypeptide of interest in an amount sufficient to elicit a protective response.

SUMMARY OF THE INVENTION

An object of this invention can be any one or all of providing recombinant vectors or viruses as well as methods for making such viruses, and providing compositions and/or vaccines as well as methods for treatment and prophylaxis of infection.

The invention provides a recombinant vector, such as a recombinant virus, e.g., a recombinant poxvirus, that contains and expresses at least one exogenous nucleic acid molecule and, the at least one exogenous nucleic acid molecule may comprise a nucleic acid molecule encoding an immunogen or epitope of interest from Rabies, such as Rabies G.

The invention also encompasses the multitude of antigens that have been successfully expressed in vivo in an animal host, to elicit an immunological and/or protective immunological response, using a poxvirus or other suitable viral expression vector, including adenovirus, adeno-associated virus (AAV), paramyxovirus, Marek's disease virus (MDV), Newcastle disease virus, (NDV), infectious bursal disease virus (IBDV), infectious bronchitis virus (IBV), etc. Examples include, but are not limited to canine distemper virus, foot-and-mouth disease virus (FMDV, U.S. Pat. No. 7,527,960 to Merial), influenza (U.S. Pat. No. 7,384,642, U.S. Pat. No. 7,910,112, U.S. Pat. No. 6,713,068, and U.S. Pat. No. 7,507,416, each to Merial), bluetongue virus (BTV, U.S. Pat. No. 7,862,821 to Merial), porcine circovirus type II (PCV2, U.S. Pat. No. 6,497,883 to Merial), nipah virus (U.S. Pat. No. 7,803,612 to Merial), hendra virus, west nile virus (WNV, U.S. Pat. No. 7,740,863 to Merial), feline leukemia virus (FeLV, U.S. Pat. No. 7,582,302 to Merial), canine leishmania (U.S. Pat. No. 7,794,736 to Merial), feline calicivirus (FCV, U.S. Pat. No. 6,914,134 to Merial), feline infectious peritonitis virus (FIPV, U.S. Pat. No. 6,096,535 to Merial), feline immunodeficiency virus (FIV), African horse sickness virus (AHSV, US2010/0119546A1 to Merial) and vesicular stomatitis virus (U.S. Pat. No. 8,008,268 to Merial), the disclosure of each document herein incorporated by reference in its entirety.

In particular, the present invention provides a recombinant vector, such as a recombinant virus, e.g., a recombinant poxvirus, that contains and expresses at least one exogenous nucleic acid molecule and, the at least one exogenous nucleic acid molecule may comprise any suitable antigen, including Rabies G polypeptides and/or variants or fragments thereof.

The invention provides a recombinant vector, such as a recombinant poxvirus that contains a first polynucleotide encoding a Rabies G polypeptide and/or variant or fragment thereof and a second polynucleotide encoding a TNFα Receptor-binding polypeptide and/or variant or fragment thereof.

The invention further provides compositions or vaccine comprising such an expression vector or the expression product(s) of such an expression vector.

The invention further provides methods for inducing an immunological (or immunogenic) or protective response against Rabies, as well as methods for preventing or treating Rabies or disease state(s) caused by Rabies, comprising administering the expression vector or an expression product of the expression vector, or a composition comprising the expression vector, or a composition comprising an expression product of the expression vector.

The invention also relates to expression products from the virus as well as antibodies generated from the expression products or the expression thereof in vivo and uses for such products and antibodies, e.g., in diagnostic applications.

Kits comprising at least one Rabies polypeptide or fragment or variant thereof and instructions for use are also provided.

The invention is also based, in part, on the unexpected and surprising result that poxviral vectors co-expressing in vivo in an animal host genes encoding antigens from pathogens, including but not limited to rabies, and a TNFα R ligand genetic adjuvant, including but not limited to OX40L, can elicit in the animal a long-lasting protective immunity against rabies. In particular, the OX40L may be homologous to the species being vaccinated, for example, canine OX40L (cOX40L) may be effectively combined with rabies G in a canine vaccine against rabies.

These and other embodiments are disclosed or are obvious from and encompassed by, the following Detailed Description.

BRIEF DESCRIPTION OF DRAWINGS

A full and enabling disclosure of the present invention, including the best mode thereof, to one of ordinary skill in the art, is set forth more particularly in the remainder of the specification, including reference to the accompanying figures, wherein:

FIG. 1 provides a schematic for the Construction of donor plasmid p397-Syn Rabies G. Location of sequencing primers used to verify the sequence of the flanking C3 arms as well as the synthetic rabies G are shown;

FIG. 2 provides a schematic representation of genomic organization of vCP3006, carrying synthetic Rabies G at C3 site and classic Rabies G at C5 site;

FIG. 3 is an image of genomic DNA isolated from wild type ALVAC and vCP3006, which had been digested with HindIII, BamHI or XbaI, and separated using agarose gel electrophoresis;

FIG. 4 presents a Southern Blot of the gel depicted in FIG. 3 (genomic DNA from wt ALVAC and vCP3006), which had been hybridized with a synthetic Rabies G-specific probe;

FIG. 5 presents a Western blot analysis of vCP3006 expression. A band corresponding to rabies virus G could only be detected in vCP3006 infected cell pellet (left). Different amounts of infected cell samples from cells infected with similar MOI of vCP3006 or vCP65a were loaded for comparison of G protein expression (right);

FIG. 6 provides a schematic drawing of vCP3006 C3 region showing primer locations;

FIG. 7 provides the sequence of vCP3006 covering the flanking C3 arms, the I3L promoter as well as the synthetic rabies G (complete sequence is as set forth in SEQ ID NO:2);

FIG. 8 presents the predicted amino acid sequence of synthetic codon-optimized rabies virus glycoprotein G (SEQ ID NO:1);

FIG. 9 is a schematic cloning diagram of donor plasmid p397-cOX40L;

FIG. 10 is a schematic representation of genomic organization of vCP3015, carrying classic Rabies virus G at the C5 site and cOX40L at the C6 site;

FIG. 11 is an agarose gel image presenting the separation of NruI digested genomic DNA on gel electrophoresis (right) and Southern blot hybridization using cOX40L probe;

FIG. 12 is an agarose gel image presenting separation of NruI digested genomic DNA (left) and Southern blot hybridization using classical rabies virus G probe (right). This probe spans both the Classic Rabies G protein and 389 bp of the C5 right arm, because of the 389 bp probe-binding there is a weak hybridization signal with the parental ALVAC genome, (lane 3), but with a band size different from that of vCP3015.

FIG. 15 is the sequence of vCP3015 covering the flanking C6 arms, the 42K promoter as well as the synthetic cOX40L (collectively as set forth in SEQ ID NO:7)

Figures 16, 17:
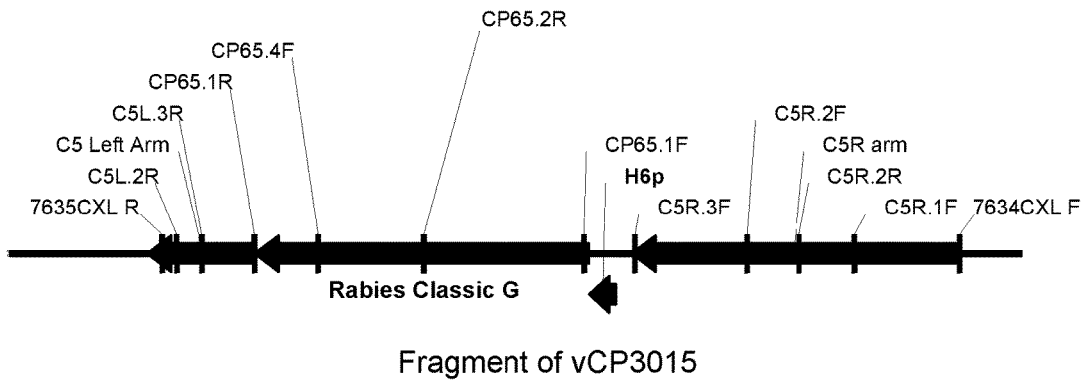
FIG. 16 is the predicted amino acid sequence of synthetic cOX40L (SEQ ID NO:12, 63, 64, 65, 66, OR 67)

FIG. 17 a schematic drawing of vCP3015 C5 region showing primer locations;

FIG. 18 is the sequence of vCP3015 covering the flanking C5 arm, the H6 promoter as well as the classical rabies virus G (collectively as set forth in SEQ ID NO:13)

Figure 20:
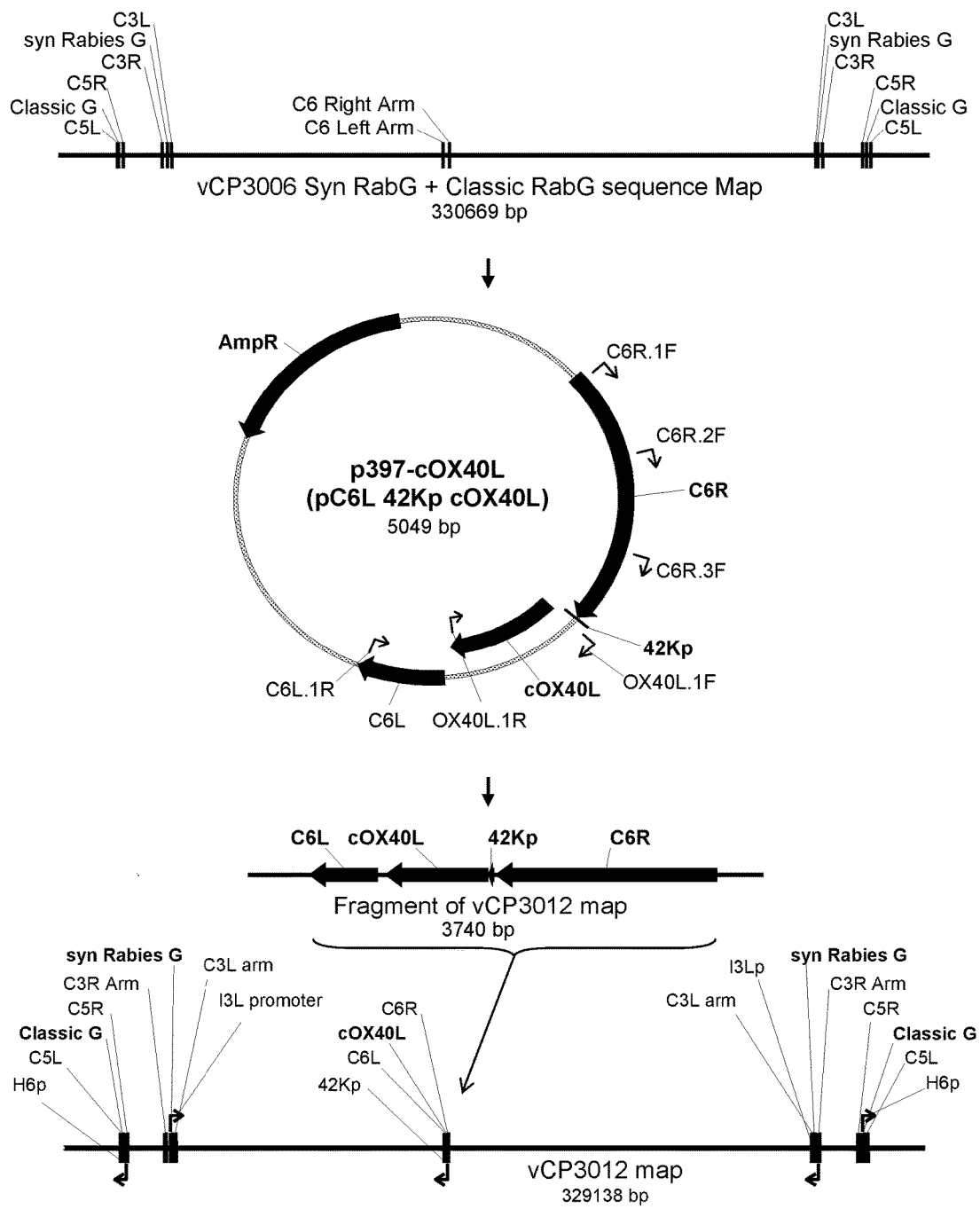
Figure 21:
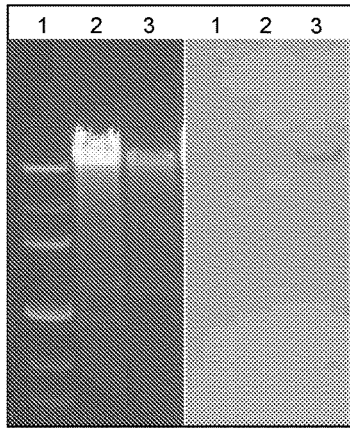
Figure 22:
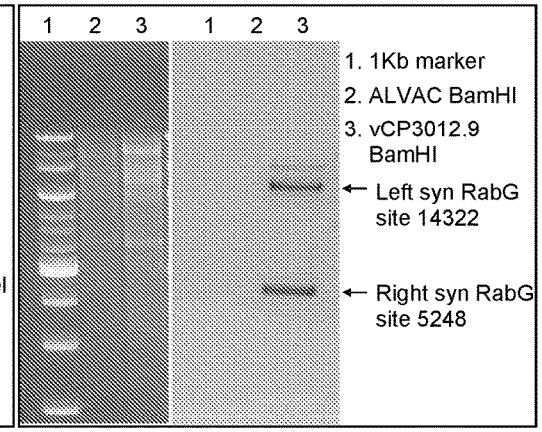

FIG. 19 is the predicted amino acid sequence of classical rabies virus G (SEQ ID NO:1). The predicted amino acid sequences of classical G and codon-optimized G (SEQ ID NO:1) are 100% identical;

FIG. 20 is a schematic representation of genomic organization of vCP3012, carrying classic Rabies virus G at the C5 site, codon-optimized synthetic rabies virus G at the C3 site and cOX40L at the C6 site;

FIG. 21 depicts separation of PmeI digested genomic DNA on gel electrophoresis and Southern blot hybridization using classical rabies virus G probe;

FIG. 22 depicts separation of BamHI digested genomic DNA on gel electrophoresis and Southern blot hybridization using synthetic rabies virus G probe.

Figure 23:
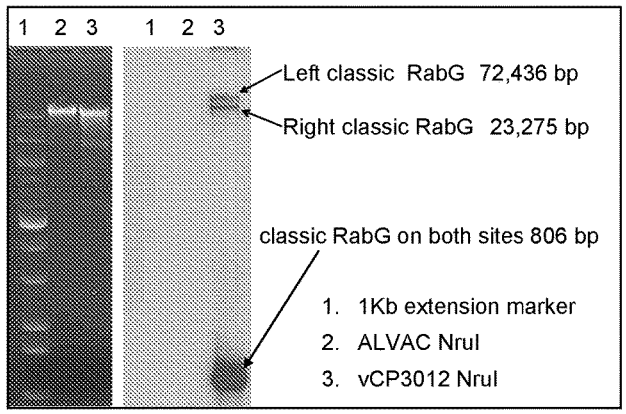
Figure 24:
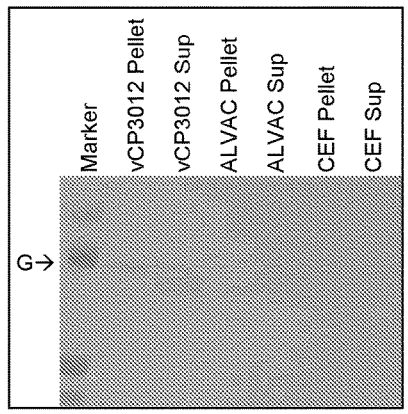
Figure 25:
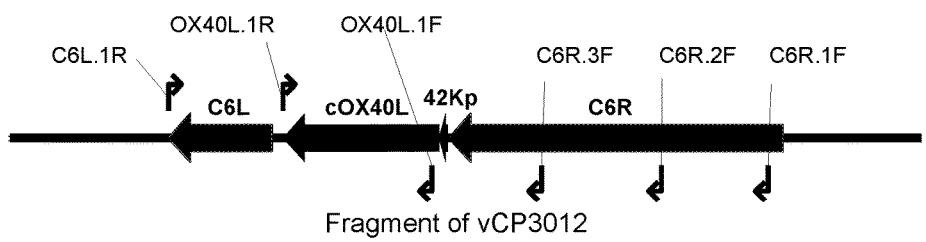

FIG. 23 depicts separation of NruI digested genomic DNA on gel electrophoresis and Southern blot hybridization using classical rabies virus G probe;

FIG. 24 is a Western blot analysis of vCP3012. A band corresponding to rabies virus G was detectable in infected cell pellet;

FIG. 25 a schematic drawing of vCP3012 C6 region showing primer locations

Figure 31:
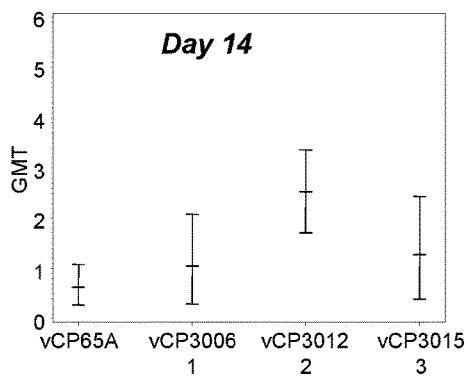
Figure 32:
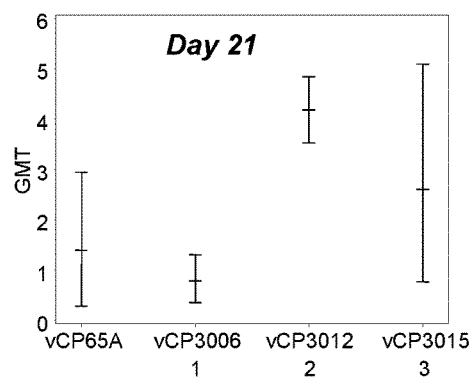
Figure 33:
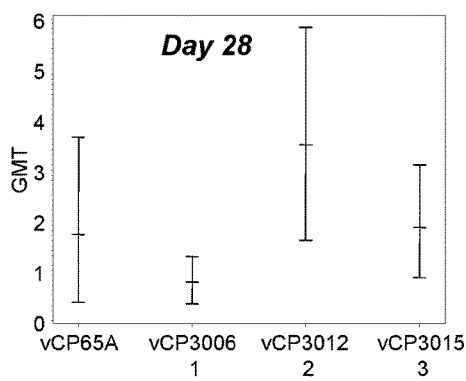
Figure 34:
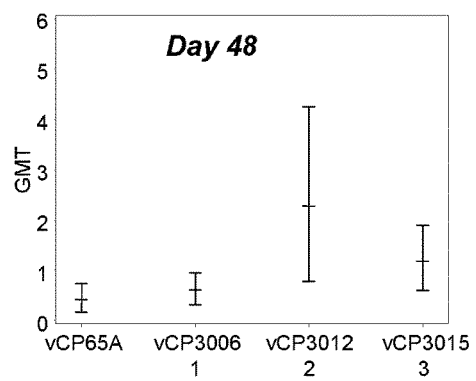
Figure 35:
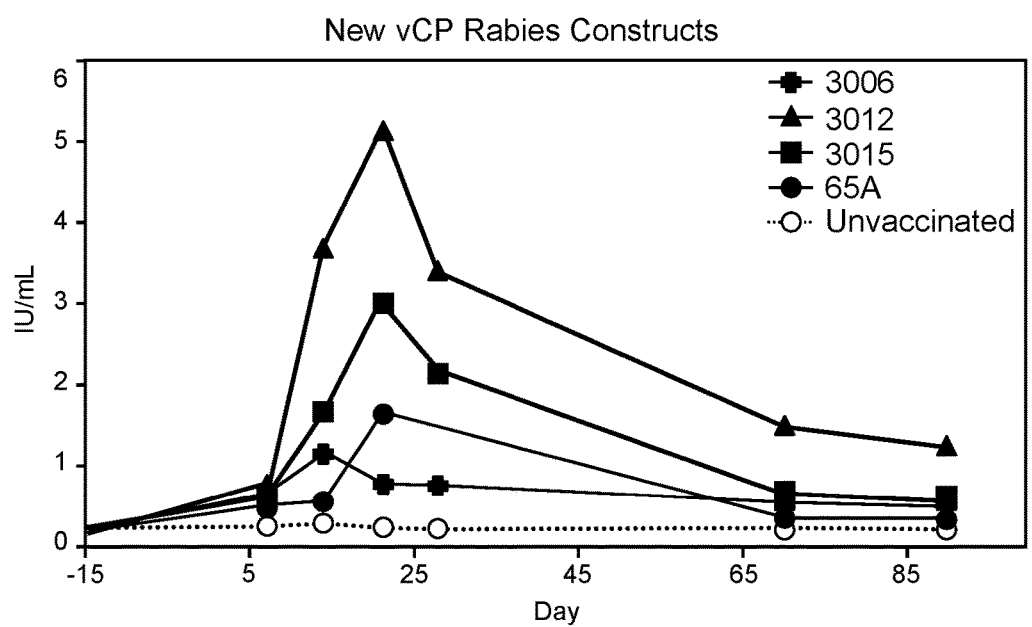

FIG. 26 presents the sequence of vCP3012 covering the flanking C6 arms, the 42K promoter as well as the synthetic cOX40L (collectively as set forth in SEQ ID NO:17);

FIG. 27 a schematic drawing of vCP3012 C3 region showing primer locations;

FIG. 28 presents the sequence of vCP3012 covering the flanking C3 arms, the I3L promoter as well as the synthetic rabies G (collectively as set forth in SEQ ID NO:20);

FIG. 29 presents a schematic diagram of a fragment of vCP3012, from C5R to C5L (i.e. rabies virus G and flanking regions);

FIG. 30 presents the sequence of vCP3012 from C5R to C5L encompassing the rabies G gene (collectively as set forth in SEQ ID NO:23). The predicted amino acids of classical rabies virus G (SEQ ID NO:1) and synthetic rabies virus G (SEQ ID NO:1) are 100% identical and are the same as described for vCP3006 or vCP3015;

FIG. 31 is a graph of GMT and 95% confidence interval (CI) for day 14;

FIG. 32 is a graph of GMT and 95% confidence interval (CI) for day 21;

FIG. 33 is a graph of GMT and 95% confidence interval (CI) for day 28;

FIG. 34 is a graph of GMT and 95% confidence interval (CI) for day 48;

FIG. 35 is a graph presenting Group titers;

FIG. 36 is a description of SEQ ID NOs:1-24, 63-67;

FIG. 37 is a description of SEQ ID NOs:25-62;

FIG. 38 presents an amino acid sequence alignment of SEQ ID NOs:12, 63-67 (i.e. selected OX40L peptides). The accompanying table indicates percent identity among the sequences.

DETAILED DESCRIPTION OF THE INVENTION

Compositions comprising an expression vector comprising a polynucleotide encoding a Rabies polypeptide and fragments and variants thereof that elicit an immunogenic response in an animal are provided. The expression vector comprising the polynucleotide encoding Rabies polypeptide or fragments or variants may be formulated into vaccines or pharmaceutical compositions and used to elicit or stimulate a protective response in an animal. In one embodiment the Rabies polypeptide is a Rabies G polypeptide or active fragment or variant thereof.

Compositions comprising an expression vector comprising a polynucleotide encoding a Rabies G polypeptide or active fragments or variants thereof and a polynucleotide encoding an OX40L polypeptide or active fragments or variants thereof are provided. In particular, the OX40L is a canine OX40L (cOX40L).

It is recognized that the polypeptides of the invention may be full length polypeptides or active fragments or variants thereof. By "active fragments" or "active variants" is intended that the fragments or variants retain the antigenic nature of the polypeptide. Thus, the present invention encompasses any Rabies polypeptide, antigen, epitope or immunogen that elicits an immunogenic response in an animal. The Rabies polypeptide, antigen, epitope or immunogen may be any Rabies polypeptide, antigen, epitope or immunogen, such as, but not limited to, a protein, peptide or fragment or variant thereof, that elicits, induces or stimulates a response in an animal, such as an avian.

A particular Rabies polypeptide of interest is Rabies glycoprotein (G). Rabies G refers to a type of glycoprotein found on the surface of the Rabies virus. It is an antigenic glycoprotein and is responsible for binding the virus to the cell that is being infected. It is recognized that precursors of any of these antigens can be used.

The antigenic polypeptides of the invention are capable of protecting against Rabies. That is, they are capable of stimulating an immune response in an animal By "antigen" or "immunogen" means a substance that induces a specific immune response in a host animal. The antigen may comprise a whole organism, killed, attenuated or live; a subunit or portion of an organism; a recombinant vector containing an insert with immunogenic properties; a piece or fragment of DNA capable of inducing an immune response upon presentation to a host animal; a polypeptide, an epitope, a hapten, or any combination thereof. Alternately, the immunogen or antigen may comprise a toxin or antitoxin.

The terms "protein", "peptide", "polypeptide" and "polypeptide fragment" are used interchangeably herein to refer to polymers of amino acid residues of any length. The polymer can be linear or branched, it may comprise modified amino acids or amino acid analogs, and it may be interrupted by chemical moieties other than amino acids. The terms also encompass an amino acid polymer that has been modified naturally or by intervention; for example disulfide bond formation, glycosylation, lipidation, acetylation, phosphorylation, or any other manipulation or modification, such as conjugation with a labeling or bioactive component.

The term "Rabies G polypeptide or polynucleotide" refers to any native or optimized Rabies G polypeptide or polynucleotide, and their derivatives and variants.

The term "OX40L polypeptide or polynucleotide" refers to any native or optimized OX40L polypeptide or polynucleotide, and their derivatives and variants.

The term "immunogenic or antigenic polypeptide" as used herein includes polypeptides that are immunologically active in the sense that once administered to the host, it is able to evoke an immune response of the humoral and/or cellular type directed against the protein. Preferably the protein fragment is such that it has substantially the same immunological activity as the total protein. Thus, a protein fragment according to the invention comprises or consists essentially of or consists of at least one epitope or antigenic determinant. An "immunogenic" protein or polypeptide, as used herein, includes the full-length sequence of the protein, analogs thereof, or immunogenic fragments thereof. By "immunogenic fragment" is meant a fragment of a protein which includes one or more epitopes and thus elicits the immunological response described above. Such fragments can be identified using any number of epitope mapping techniques, well known in the art. See, e.g., Epitope Mapping Protocols in Methods in Molecular Biology, Vol. 66 (Glenn E. Morris, Ed., 1996). For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al., 1984; Geysen et al., 1986. Similarly, conformational epitopes are readily identified by determining spatial conformation of amino acids such as by, e.g., x-ray crystallography and 2-dimensional nuclear magnetic resonance. See, e.g., Epitope Mapping Protocols, supra. Methods especially applicable to the proteins of *T. parva* are fully described in PCT/US2004/022605 incorporated herein by reference in its entirety.

As discussed herein, the invention encompasses active fragments and variants of the antigenic polypeptide. Thus, the term "immunogenic or antigenic polypeptide" further contemplates deletions, additions and substitutions to the sequence, so long as the polypeptide functions to produce an immunological response as defined herein. The term "conservative variation" denotes the replacement of an amino acid residue by another biologically similar residue, or the replacement of a nucleotide in a nucleic acid sequence such that the encoded amino acid residue does not change or is another biologically similar residue. In this regard, particularly preferred substitutions will generally be conservative in nature, i.e., those substitutions that take place within a family of amino acids. For example, amino acids are generally divided into four families: (1) acidic-aspartate and glutamate; (2) basic-lysine, arginine, histidine; (3) non-polar-alanine, valine, leucine, isoleucine, proline, phenylalanine, methionine, tryptophan; and (4) uncharged polar-glycine, asparagine, glutamine, cystine, serine, threonine, tyrosine. Phenylalanine, tryptophan, and tyrosine are sometimes classified as aromatic amino acids. Examples of conservative variations include the substitution of one hydrophobic residue such as isoleucine, valine, leucine or methionine for another hydrophobic residue, or the substitution of one polar residue for another polar residue, such as the substitution of arginine for lysine, glutamic acid for aspartic acid, or glutamine for asparagine, and the like; or a similar conservative replacement of an amino acid with a structurally related amino acid that will not have a major effect on the biological activity. Proteins having substantially the same amino acid sequence as the reference molecule but possessing minor amino acid substitutions that do not substantially affect the immunogenicity of the protein are, therefore, within the definition of the reference polypeptide. All of the polypeptides produced by these modifications are included herein. The term "conservative variation" also includes the use of a substituted amino acid in place of an unsubstituted parent amino acid provided that antibodies raised to the substituted polypeptide also immunoreact with the unsubstituted polypeptide.

The term "epitope" refers to the site on an antigen or hapten to which specific B cells and/or T cells respond. The term is also used interchangeably with "antigenic determinant" or "antigenic determinant site". Antibodies that recognize the same epitope can be identified in a simple immunoassay showing the ability of one antibody to block the binding of another antibody to a target antigen.

An "immunological response" to a composition or vaccine is the development in the host of a cellular and/or antibody-mediated immune response to a composition or vaccine of interest. Usually, an "immunological response" includes but is not limited to one or more of the following effects: the production of antibodies, B cells, helper T cells, and/or cytotoxic T cells, directed specifically to an antigen or antigens included in the composition or vaccine of interest. Preferably, the host will display either a therapeutic or protective immunological response such that resistance to new infection will be enhanced and/or the clinical severity of the disease reduced. Such protection will be demonstrated by either a reduction or lack of symptoms normally displayed by an infected host, a quicker recovery time and/or a lowered viral titer in the infected host.

By "animal" is intended mammals, birds, and the like. Animal or host as used herein includes mammals and human. The animal may be selected from the group consisting of equine (e.g., horse), canine (e.g., dogs, wolves, foxes, coyotes, jackals), feline (e.g., lions, tigers, domestic cats, wild cats, other big cats, and other felines including cheetahs and lynx), ovine (e.g., sheep), bovine (e.g., cattle), porcine (e.g., pig), avian (e.g., chicken, duck, goose, turkey, quail, pheasant, parrot, finches, hawk, crow, ostrich, emu and cassowary), primate (e.g., prosimian, tarsier, monkey, gibbon, ape), ferrets, seals, and fish. The term "animal" also includes an individual animal in all stages of development, including embryonic and fetal stages.

Unless otherwise explained, all technical and scientific terms used herein have the same meaning as commonly understood by one of ordinary skill in the art to which this disclosure belongs. The singular terms "a", "an", and "the" include plural referents unless context clearly indicates otherwise. Similarly, the word "or" is intended to include "and" unless the context clearly indicate otherwise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

Compositions

The present invention relates to a Rabies vaccine or composition which may comprise a recombinant or expression vector comprising a polynucleotide encoding a Rabies polypeptide, antigen, epitope or immunogen and a pharmaceutically or veterinarily acceptable carrier, excipient, or vehicle. The Rabies polypeptide, antigen, epitope or immunogen may be any Rabies polypeptide, antigen, epitope or immunogen, such as, but not limited to, a protein, peptide or fragment thereof, that elicits, induces or stimulates a response in an animal.

The present invention relates to a Rabies vaccine or composition which may comprise a recombinant or expression vector comprising a polynucleotide encoding a Rabies G polypeptide and a pharmaceutically or veterinarily acceptable carrier, excipient, or vehicle. In one embodiment, the expression vector may further comprise a polynucleotide encoding an OX40L polypeptide.

In another embodiment, the pharmaceutically or veterinarily acceptable carrier, excipient, or vehicle may be a water-in-oil emulsion. In yet another embodiment, the water-in-oil emulsion may be a water/oil/water (W/O/W) triple emulsion. In yet another embodiment, the pharmaceutically or veterinarily acceptable carrier, excipient, or vehicle may be an oil-in-water emulsion.

In an embodiment, the Rabies polypeptide, antigen or fragment or variant thereof comprises a Rabies G polypeptide or fragment or variant thereof. In an aspect of this embodiment, the Rabies G polypeptide or fragment or variant thereof is a recombinant polypeptide produced by a Rabies G gene. In another aspect of this embodiment, the Rabies G gene has at least 70% identity to the sequence as set forth in SEQ ID NO: 5 or 16. In another aspect of this embodiment, the Rabies G polypeptide or fragment or variant thereof has at least 80% identity to the sequence as set forth in SEQ ID NO:1.

In another embodiment, the OX40L polypeptide, antigen or fragment or variant is a recombinant polypeptide produced by an OX40L gene. In another aspect of this embodiment, the OX40L gene has at least 70% identity to the sequence as set forth in SEQ ID NO:10. In another aspect of this embodiment, the OX40L polypeptide or fragment or variant thereof has at least 80% identity to the sequence as set forth in SEQ ID NO:12, 63, 64, 65, 66, OR 67.

In another embodiment the present invention provides for a novel, genetically-adjuvanted rabies vaccine, for non-sole use in companion animals such as cats, dogs, and ferrets, which comprises a recombinant poxvirus vector, which contains and expresses Rabies G and OX40L. In another embodiment, the vector may comprise a recombinant canarypox. In another embodiment, the rabies surface glycoprotein gene may encode the rabies glycoprotein G, having the sequence as set forth in SEQ ID NO:1, and the OX40L has the sequence as set forth in SEQ ID NO:12, 63, 64, 65, 66, OR 67.

Synthetic antigens are also included within the definition, for example, polyepitopes, flanking epitopes, and other recombinant or synthetically derived antigens. See, e.g., Bergmann et al., 1993; Bergmann et al., 1996; Suhrbier, 1997; Gardner et al., 1998. Immunogenic fragments, for purposes of the present invention, will usually include at least about 3 amino acids, at least about 5 amino acids, at least about 10-15 amino acids, or about 15-25 amino acids or more amino acids, of the molecule. There is no critical upper limit to the length of the fragment, which could comprise nearly the full-length of the protein sequence, or even a fusion protein comprising at least one epitope of the protein.

Accordingly, a minimum structure of a polynucleotide expressing an epitope is that it comprises or consists essentially of or consists of nucleotides encoding an epitope or antigenic determinant of a Rabies polypeptide. A polynucleotide encoding a fragment of a Rabies polypeptide may comprise or consist essentially of or consist of a minimum of 15 nucleotides, about 30-45 nucleotides, about 45-75, or at least 57, 87 or 150 consecutive or contiguous nucleotides of the sequence encoding the polypeptide. Epitope determination procedures, such as, generating overlapping peptide libraries (Hemmer et al., 1998), Pepscan (Geysen et al., 1984; Geysen et al., 1985; Van der Zee R. et al., 1989; Geysen, 1990; Multipin® Peptide Synthesis Kits de Chiron) and algorithms (De Groot et al., 1999; PCT/US2004/022605) can be used in the practice of the invention.

The term "nucleic acid" and "polynucleotide" refers to RNA or DNA that is linear or branched, single or double stranded, or a hybrid thereof. The term also encompasses RNA/DNA hybrids. The following are non-limiting examples of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes and primers. A polynucleotide may comprise modified nucleotides, such as methylated nucleotides and nucleotide analogs, uracyl, other sugars and linking groups such as fluororibose and thiolate, and nucleotide branches. The sequence of nucleotides may be further modified after polymerization, such as by conjugation, with a labeling component. Other types of modifications included in this definition are caps, substitution of one or more of the naturally occurring nucleotides with an analog, and introduction of means for attaching the polynucleotide to proteins, metal ions, labeling components, other polynucleotides or solid support. The polynucleotides can be obtained by chemical synthesis or derived from a microorganism.

The term "gene" is used broadly to refer to any segment of polynucleotide associated with a biological function. Thus, genes include introns and exons as in genomic sequence, or just the coding sequences as in cDNAs and/or the regulatory sequences required for their expression. For example, gene also refers to a nucleic acid fragment that expresses mRNA or functional RNA, or encodes a specific protein, and which includes regulatory sequences.

As regards variations of the OX40L, a "functional fragment or variant of OX40L" is defined herein as a peptide that adjuvants/augments the immune response elicited by an immunogenic peptide via the same mechanism, and to a comparable extent, as compared to the OX40L of the present disclosure. For example, if a feline OX40L, when co-expressed with rabies G in a canine host results in an immune response against rabies that is greater than that elicited by a rabies G expression vector alone, and the feline OX40L is acting via the same mechanism (e.g. binding TNF receptor), then the feline OX40L would be considered to be a "functional fragment or variant" of the canine OX40L exemplified herein. Likewise, polymorphic versions of canine OX40L that are capable of augmenting an immune response are also "function fragments or variants" of cOX40L. Finally, if a truncated version of an OX40L adjuvants/augments an immune response to a comparable extent as the corresponding full-length OX40L, the truncated version is considered to be a "functional fragment or variant of OX40L".

The invention further comprises a complementary strand to a polynucleotide encoding a Rabies antigen, epitope or immunogen or to a polynucleotide encoding an OX40L antigen, epitope or immunogen. The complementary strand can be polymeric and of any length, and can contain deoxyribonucleotides, ribonucleotides, and analogs in any combination.

An "isolated" biological component (such as a nucleic acid or protein or organelle) refers to a component that has been substantially separated or purified away from other biological components in the cell of the organism in which the component naturally occurs, for instance, other chromosomal and extra-chromosomal DNA and RNA, proteins, and organelles. Nucleic acids and proteins that have been "isolated" include nucleic acids and proteins purified by standard purification methods. The term also embraces nucleic acids and proteins prepared by recombinant technology as well as chemical synthesis.

The term "purified" as used herein does not require absolute purity; rather, it is intended as a relative term. Thus, for example, a partially purified polypeptide preparation is one in which the polypeptide is more enriched than the polypeptide is in its natural environment. That is the polypeptide is separated from cellular components. By "substantially purified" is intended that such that at least 60%, at least 70%, at least 80%, at least 90%, at least 95%, or at least 98%, or more of the cellular components or materials have been removed. Likewise, a polypeptide may be partially purified. By "partially purified" is intended that less than 60% of the cellular components or material is removed. The same applies to polynucleotides. The polypeptides disclosed herein can be purified by any of the means known in the art.

Moreover, homologs of Rabies G polypeptides and homologs of OX40L polypeptides are intended to be within the scope of the present invention. As used herein, the term "homologs" includes orthologs, analogs and paralogs. The tem "analogs" refers to two polynucleotides or polypeptides that have the same or similar function, but that have evolved separately in unrelated organisms. The term "orthologs" refers to two polynucleotides or polypeptides from different species, but that have evolved from a common ancestral gene by speciation. Normally, orthologs encode polypeptides having the same or similar functions. The term "paralogs" refers to two polynucleotides or polypeptides that are related by duplication within a genome. Paralogs usually have different functions, but these functions may be related. For example, analogs, orthologs, and paralogs of a wild-type Rabies polypeptide can differ from the wild-type Rabies polypeptide by post-translational modifications, by amino acid sequence differences, or by both. In particular, homologs of the invention will generally exhibit at least 80-85%, 85-90%, 90-95%, or 95%, 96%, 97%, 98%, 99% sequence identity, with all or part of the wild-type Rabies polypeptide or polynucleotide sequences, and will exhibit a similar function.

In another aspect, the present invention provides a polypeptide having at least 70%, at least 75%, at least 80%, at least 85%, at least 90%, at least 95%, 96%, 97%, 98% or 99% sequence identity to a polypeptide having a sequence as set forth in SEQ ID NO:1. In yet another aspect, the present invention provides fragments and variants of the Rabies polypeptides or OX40L polypeptides identified above (SEQ ID NO:1 or 12, 63-67) which may readily be prepared by one of skill in the art using well-known molecular biology techniques.

Variants are homologous polypeptides having an amino acid sequence at least 75%, 80%, 85%, 90%, 95%, 96%, 97%, 98%, or 99% identity to the amino acid sequence as set forth in SEQ ID NO:1 or 12, 63-67.

Variants include allelic variants. The term "allelic variant" refers to a polynucleotide or a polypeptide containing polymorphisms that lead to changes in the amino acid sequences of a protein and that exist within a natural population (e.g., a virus species or variety). Such natural allelic variations can typically result in 1-5% variance in a polynucleotide or a polypeptide. Allelic variants can be identified by sequencing the nucleic acid sequence of interest in a number of different species, which can be readily carried out by using hybridization probes to identify the same gene genetic locus in those species. Any and all such nucleic acid variations and resulting amino acid polymorphisms or variations that are the result of natural allelic variation and that do not alter the functional activity of gene of interest, are intended to be within the scope of the invention.

As used herein, the term "derivative" or "variant" refers to a polypeptide, or a nucleic acid encoding a polypeptide, that has one or more conservative amino acid variations or other minor modifications such that (1) the corresponding polypeptide has substantially equivalent function when compared to the wild type polypeptide or (2) an antibody raised against the polypeptide is immunoreactive with the wild-type polypeptide. These variants or derivatives include polypeptides having minor modifications of the Rabies polypeptide or OX40L primary amino acid sequences that may result in peptides which have substantially equivalent activity as compared to the unmodified counterpart polypeptide. Such modifications may be deliberate, as by site-directed mutagenesis, or may be spontaneous. The term "variant" further contemplates deletions, additions and substitutions to the sequence, so long as the polypeptide functions to produce an immunological response as defined herein.

The term "conservative variation" denotes the replacement of an amino acid residue by another biologically similar residue, or the replacement of a nucleotide in a nucleic acid sequence such that the encoded amino acid residue does not change or is another biologically similar residue. In this regard, particularly preferred substitutions will generally be conservative in nature, as described above.

An immunogenic fragment of a Rabies polypeptide or OX40L polypeptide includes at least 8, 10, 13, 14, 15, or 20 consecutive amino acids, at least 21 amino acids, at least 23 amino acids, at least 25 amino acids, or at least 30 amino acids of a Rabies G polypeptide having a sequence as set forth in SEQ ID NO:1, or variants thereof, or of an OX40L polypeptide having a sequence as set forth in SEQ ID NO:12, 63, 64, 65, 66, OR 67, or variants thereof.

In another aspect, the present invention provides a polynucleotide encoding a Rabies G polypeptide, such as a polynucleotide encoding a polypeptide having a sequence as set forth in SEQ ID NO:5 or 16. In yet another aspect, the present invention provides a polynucleotide encoding a polypeptide having at least 70%, at least 75%, at least 80%, at least 85%, at least 90%, at least 95%, 96%, 97%, 98% or 99% sequence identity to a polypeptide having a sequence as set forth in SEQ ID NO:1, or a conservative variant, an allelic variant, a homolog or an immunogenic fragment comprising at least eight or at least ten consecutive amino acids of one of these polypeptides, or a combination of these polypeptides.

In yet another aspect, the present invention provides a polynucleotide encoding an OX40L polypeptide, such as a polynucleotide encoding a polypeptide having a sequence as set forth in SEQ ID NO:12, 63, 64, 65, 66, OR 67. In yet another aspect, the present invention provides a polynucleotide encoding a polypeptide having at least 70%, at least 75%, at least 80%, at least 85%, at least 90%, at least 95%, 96%, 97%, 98% or 99% sequence identity to a polypeptide having a sequence as set forth in SEQ ID NO:12, 63, 64, 65, 66, OR 67, or a conservative variant, an allelic variant, a homolog or an immunogenic fragment comprising at least eight or at least ten consecutive amino acids of one of these polypeptides, or a combination of these polypeptides.

In another aspect, the present invention provides a polynucleotide having a nucleotide sequence as set forth in SEQ ID NO:5, 10, or 16, or a variant thereof. In yet another aspect, the present invention provides a polynucleotide having at least 70%, at least 75%, at least 80%, at least 85%, at least 90%, at least 95%, at least 95%, 96%, 97%, 98% or 99% sequence identity to one of a polynucleotide having a sequence as set forth in SEQ ID NO:5, 10, or 16, or a variant thereof.

The polynucleotides of the disclosure include sequences that are degenerate as a result of the genetic code, e.g., optimized codon usage for a specific host. As used herein, "optimized" refers to a polynucleotide that is genetically engineered to increase its expression in a given species. To provide optimized polynucleotides coding for Rabies G polypeptides or OX40L polypeptides, the DNA sequence of the Rabies G gene or OX40L gene can be modified to 1) comprise codons preferred by highly expressed genes in a particular species; 2) comprise an A+T or G+C content in nucleotide base composition to that substantially found in said species; 3) form an initiation sequence of said species; or 4) eliminate sequences that cause destabilization, inappropriate polyadenylation, degradation and termination of RNA, or that form secondary structure hairpins or RNA splice sites. Increased expression of Rabies G protein or OX40L protein in said species can be achieved by utilizing the distribution frequency of codon usage in eukaryotes and prokaryotes, or in a particular species. The term "frequency of preferred codon usage" refers to the preference exhibited by a specific host cell in usage of nucleotide codons to specify a given amino acid. There are 20 natural amino acids, most of which are specified by more than one codon. Therefore, all degenerate nucleotide sequences are included in the disclosure as long as the amino acid sequence of the Rabies G polypeptide or the OX40L polypeptide encoded by the nucleotide sequence is functionally unchanged.

The sequence identity between two amino acid sequences may be established by the NCBI (National Center for Biotechnology Information) pairwise blast and the blosum62 matrix, using the standard parameters (see, e.g., the BLAST or BLASTX algorithm available on the "National Center for Biotechnology Information" (NCBI, Bethesda, Md., USA) server, as well as in Altschul et al.; and thus, this document speaks of using the algorithm or the BLAST or BLASTX and BLOSUM62 matrix by the term "blasts").

The "identity" with respect to sequences can refer to the number of positions with identical nucleotides or amino acids divided by the number of nucleotides or amino acids in the shorter of the two sequences wherein alignment of the two sequences can be determined in accordance with the Wilbur and Lipman algorithm (Wilbur and Lipman), for instance, using a window size of 20 nucleotides, a word length of 4 nucleotides, and a gap penalty of 4, and computer-assisted analysis and interpretation of the sequence data including alignment can be conveniently performed using commercially available programs (e.g., Intelligenetics™ Suite, Intelligenetics Inc. CA). When RNA sequences are said to be similar, or have a degree of sequence identity or homology with DNA sequences, thymidine (T) in the DNA sequence is considered equal to uracil (U) in the RNA sequence. Thus, RNA sequences are within the scope of the invention and can be derived from DNA sequences, by thymidine (T) in the DNA sequence being considered equal to uracil (U) in RNA sequences.

The sequence identity or sequence similarity of two amino acid sequences, or the sequence identity between two nucleotide sequences can be determined using Vector NTI software package (Invitrogen, 1600 Faraday Ave., Carlsbad, Calif.).

The following documents provide algorithms for comparing the relative identity or homology of sequences, and additionally or alternatively with respect to the foregoing, the teachings in these references can be used for determining percent homology or identity: Needleman S B and Wunsch C D; Smith T F and Waterman M S; Smith T F, Waterman M S and Sadler J R; Feng D F and Dolittle R F; Higgins D G and Sharp P M; Thompson J D, Higgins D G and Gibson T J; and, Devereux J, Haeberlie P and Smithies O. And, without undue experimentation, the skilled artisan can consult with many other programs or references for determining percent homology.

Hybridization reactions can be performed under conditions of different "stringency." Conditions that increase stringency of a hybridization reaction are well known. See for example, "Molecular Cloning: A Laboratory Manual", second edition (Sambrook et al., 1989).

The invention further encompasses the Rabies polynucleotide or OX40L polynucleotide or both contained in a vector molecule or an expression vector and operably linked to a promoter element and optionally to an enhancer.

A "vector" refers to a recombinant DNA or RNA plasmid or virus that comprises a heterologous polynucleotide to be delivered to a target cell, either in vitro or in vivo. The heterologous polynucleotide may comprise a sequence of interest for purposes of prevention or therapy, and may optionally be in the form of an expression cassette. As used herein, a vector needs not be capable of replication in the ultimate target cell or subject. The term includes cloning vectors and viral vectors.

The term "recombinant" means a polynucleotide with semisynthetic, or synthetic origin which either does not occur in nature or is linked to another polynucleotide in an arrangement not found in nature.

"Heterologous" means derived from a genetically distinct entity from the rest of the entity to which it is being compared. For example, a polynucleotide may be placed by genetic engineering techniques into a plasmid or vector derived from a different source, and is a heterologous polynucleotide. A promoter removed from its native coding sequence and operatively linked to a coding sequence other than the native sequence is a heterologous promoter.

The polynucleotides of the invention may comprise additional sequences, such as additional encoding sequences within the same transcription unit, controlling elements such as promoters, ribosome binding sites, 5'UTR, 3'UTR, transcription terminators, polyadenylation sites, additional transcription units under control of the same or a different promoter, sequences that permit cloning, expression, homologous recombination, and transformation of a host cell, and any such construct as may be desirable to provide embodiments of this invention.

Elements for the expression of a Rabies G polypeptide, antigen, epitope or immunogen or an OX40L polypeptide are advantageously present in an inventive vector. In minimum manner, this comprises an initiation codon (ATG), a stop codon and a promoter, and optionally also a polyadenylation sequence for certain vectors such as plasmid and certain viral vectors, e.g., viral vectors other than poxviruses. When the polynucleotide encodes a polypeptide fragment, e.g. a Rabies G polypeptide, advantageously, in the vector, an ATG is placed at 5' of the reading frame and a stop codon is placed at 3'. Other elements for controlling expression may be present, such as enhancer sequences, stabilizing sequences, such as intron and signal sequences permitting the secretion of the protein.

The present invention also relates to preparations comprising vectors, such as expression vectors, e.g., therapeutic compositions. The preparations can comprise one or more vectors, e.g., expression vectors, such as in vivo expression vectors, comprising and expressing one or more Rabies G or OX40L polypeptides, antigens, epitopes or immunogens.

In one embodiment, the vector contains and expresses a polynucleotide that comprises a polynucleotide coding for and/or expressing a Rabies G antigen, epitope or immunogen, in a pharmaceutically or veterinarily acceptable carrier, excipient or vehicle. Thus, according to an embodiment of the invention, the other vector or vectors in the preparation comprises, consists essentially of or consists of a polynucleotide that encodes, and under appropriate circumstances the vector expresses one or more other proteins of a Rabies G polypeptide, antigen, epitope or immunogen (e.g., hemagglutinin, neuraminidase, nucleoprotein) or a fragment thereof.

According to another embodiment, the vector or vectors in the preparation comprise, or consist essentially of, or consist of polynucleotide(s) encoding one or more proteins or fragment(s) of a Rabies G polypeptide, antigen, epitope or immunogen, or an OX40L polypeptide, antigen, epitope or immunogen, or a combination thereof. In another embodiment, the preparation comprises one, two, or more vectors comprising polynucleotides encoding and expressing, advantageously in vivo, a Rabies G polypeptide, antigen, fusion protein or an epitope thereof. The invention is also directed at mixtures of vectors that comprise polynucleotides encoding and expressing different a Rabies G polypeptides, antigens, epitopes, fusion protein, or immunogens, e.g., a Rabies G polypeptide, antigen, epitope or immunogen from different species such as, but not limited to, humans, pigs, cows or cattle, dogs, cats, and avian.

According to a yet further embodiment of the invention, the expression vector is a plasmid vector, in particular an in vivo expression vector. In a specific, non-limiting example, the pVR1020 or 1012 plasmid (VICAL Inc.; Luke et al., 1997; Hartikka et al., 1996, see, e.g., U.S. Pat. Nos. 5,846, 946 and 6,451,769) can be utilized as a vector for the insertion of a polynucleotide sequence. The pVR1020 plasmid is derived from pVR1012 and contains the human tPA signal sequence. In one embodiment the human tPA signal comprises from amino acid M(1) to amino acid S(23) in Genbank under the accession number HUMTPA14. In another specific, non-limiting example, the plasmid utilized as a vector for the insertion of a polynucleotide sequence can contain the signal peptide sequence of equine IGF1 from amino acid M(24) to amino acid A(48) in Genbank under the accession number U28070. Additional information on DNA plasmids which may be consulted or employed in the practice are found, for example, in U.S. Pat. Nos. 6,852,705; 6,818,628; 6,586,412; 6,576,243; 6,558,674; 6,464,984; 6,451,770; 6,376,473 and 6,221,362.

The term plasmid covers any DNA transcription unit comprising a polynucleotide according to the invention and the elements necessary for its in vivo expression in a cell or cells of the desired host or target; and, in this regard, it is noted that a supercoiled or non-supercoiled, circular plasmid, as well as a linear form, are intended to be within the scope of the invention.

Each plasmid comprises or contains or consists essentially of, in addition to the polynucleotide encoding a Rabies G polypeptide, antigen, epitope or immunogen, optionally fused with a heterologous peptide sequence, variant, analog or fragment, operably linked to a promoter or under the control of a promoter or dependent upon a promoter. In general, it is advantageous to employ a strong promoter functional in eukaryotic cells. The strong promoter may be, but not limited to, the immediate early cytomegalovirus promoter (CMV-IE) of human or murine origin, or optionally having another origin such as the rat or guinea pig.

In more general terms, the promoter has either a viral, or a cellular origin. A strong viral promoter other than CMV-IE that may be usefully employed in the practice of the invention is the early/late promoter of the SV40 virus or the LTR promoter of the Rous sarcoma virus. A strong cellular promoter that may be usefully employed in the practice of the invention is the promoter of a gene of the cytoskeleton, such as e.g. the desmin promoter (Kwissa et al., 2000), or the actin promoter (Miyazaki et al., 1989).

As to the polyadenylation signal (polyA) for the plasmids and viral vectors other than poxviruses, use can be made of the poly(A) signal of the bovine growth hormone (bGH) gene (see U.S. Pat. No. 5,122,458), or the poly(A) signal of the rabbit β-globin gene or the poly(A) signal of the SV40 virus.

A "host cell" denotes a prokaryotic or eukaryotic cell that has been genetically altered, or is capable of being genetically altered by administration of an exogenous polynucleotide, such as a recombinant plasmid or vector. When referring to genetically altered cells, the term refers both to the originally altered cell and to the progeny thereof.

Methods of Use and Article of Manufacture

The present invention includes the following method embodiments. In an embodiment, a method of vaccinating an animal comprising administering a composition comprising a vector comprising a polynucleotide encoding a Rabies G polypeptide or fragment or variant thereof and a pharmaceutical or veterinarily acceptable carrier, excipient, or vehicle to an animal is disclosed. In one aspect of this embodiment, the animal is an avian, an equine, a canine, a feline, a ferret, a seal, or a porcine.

In one embodiment of the invention, a prime-boost regimen can be employed, which is comprised of at least one primary administration and at least one booster administration using at least one common polypeptide, antigen, epitope or immunogen. Typically the immunological composition or vaccine used in primary administration is different in nature from those used as a booster. However, it is noted that the same composition can be used as the primary administration and the booster administration. This administration protocol is called "prime-boost".

In the present invention a recombinant viral vector is used to express a Rabies coding sequence or fragments thereof encoding a Rabies polypeptide or fragment or variant thereof. Specifically, the viral vector can express a Rabies sequence, more specifically a Rabies G gene or fragment thereof that encodes an antigenic polypeptide. Viral vector contemplated herein includes, but not limited to, poxvirus [e.g., vaccinia virus or attenuated vaccinia virus, avipox virus or attenuated avipox virus (e.g., canarypox, fowlpox, dovepox, pigeonpox, quailpox, ALVAC, TROVAC; see e.g., U.S. Pat. No. 5,505,941, U.S. Pat. No. 5,494,8070), raccoonpox virus, swinepox virus, etc.], adenovirus (e.g., human adenovirus, canine adenovirus), herpesvirus (e.g. canine herpesvirus, feline herpesvirus, bovine herpesvirus, swine herpesvirus), baculovirus, retrovirus, etc. In another embodiment, the avipox expression vector may be a canarypox vector, such as, ALVAC. In yet another embodiment, the avipox expression vector may be a fowlpox vector, such as, TROVAC. The Rabies polypeptide, antigen, epitope or immunogen may be a Rabies G. For example, the poxvirus vector comprising the Rabies G may be vectors as described in U.S. Pat. No. 5,756,102. The Rabies G polypeptide or antigen of the invention to be expressed is inserted under the control of a specific poxvirus promoter, e.g., the vaccinia promoter 7.5 kDa (Cochran et al., 1985), the vaccinia promoter I3L (Riviere et al., 1992), the vaccinia promoter G (Shida, 1986), the cowpox promoter ATI (Funahashi et al., 1988), the vaccinia promoter H6 (Taylor et al., 1988b; Guo et al., 1989; Perkus et al., 1989), inter alia.

A prime-boost regimen comprises at least one prime-administration and at least one boost administration using at least one common polypeptide and/or variants or fragments thereof. The vaccine used in prime-administration may be different in nature from those used as a later booster vaccine. The prime-administration may comprise one or more administrations. Similarly, the boost administration may comprise one or more administrations.

In one aspect of the prime-boost protocol or regime of the invention, a prime-boost protocol may comprise the administration of a composition comprising a recombinant viral vector that contains and expresses a Rabies G polypeptide, antigen and/or variants or fragments thereof in vivo followed by the administration of a recombinant Rabies G polypeptide or antigen of the invention. Likewise, a prime-boost protocol may comprise the administration of a composition comprising a Rabies G antigen of the invention followed by the administration of a recombinant viral vector that contains and expresses a Rabies G polypeptide or antigen and/or variants or fragments thereof in vivo. It is further noted that both the primary and the secondary administrations may comprise the recombinant viral vector that contains and expresses a Rabies G polypeptide of the invention. Thus, the recombinant Rabies viral vector of the invention may be administered in any order with a recombinant Rabies antigen or alternatively may be used alone as both the primary and secondary compositions.

In another aspect of the prime-boost protocol of the invention, a composition comprising a recombinant viral vector that contains and expresses a Rabies G polypeptide, antigen and/or variants or fragments thereof in vivo of the invention is administered followed by the administration of an inactivated viral composition or vaccine comprising the Rabies polypeptide or antigen. Likewise, a prime-boost protocol may comprise the administration of an inactivated viral composition or vaccine followed by the administration of a recombinant viral vector that contains and expresses a Rabies G polypeptide, antigen and/or variants or fragments thereof in vivo of the invention.

In yet another aspect of the prime-boost protocol of the invention, the prime-boost protocol comprises at least one prime-administration of a recombinant viral vector-based composition of the invention and at least one boost-administration of a plasmid-based composition of the invention. Likewise, the primes-boost may comprise at least one prime-administration of at least one prime-administration of a plasmid-based composition of the invention and at least one boost-administration of a recombinant viral-vector based composition of the invention.

The dose volume of compositions for target species that are mammals, e.g., the dose volume of dog compositions, based on viral vectors, e.g., non-poxvirus-viral-vector-based compositions, is generally between about 0.1 to about 2.0 ml, between about 0.1 to about 1.0 ml, and between about 0.5 ml to about 1.0 ml.

The efficacy of the vaccines may be tested after the last immunization by challenging animals, such as dog, with a virulent strain of Rabies. In general, animals are anesthetized and 1.0 ml challenge material is administered via IM injection (0.5 ml into each frontalis and/or masseter muscle). The target dose is about 3.8 log $10LD_{50}$/ml, and a challenge back titration in mice is performed to verify the actual inoculated dose. Seven days prior to challenge dogs are acclimated to individual cages and maintained in individual cages until the end of the study. Animals are fed a commercially available diet and be provided with water ad libitum. SAS® software V9.1 Enterprise Guide may be used for producing a randomization table for housing. On D0, the challenge strain may be prepared by diluting the initial challenge suspension stock 1:100 in PBS+2% fetal calf serum. The diluted challenge material may be placed in a sterile, sealed and capped vial, labeled accordingly and kept on ice until used. The morning before challenge, it is advisable to administer analgesic/antiinflammatory, for example, firocoxib 5 mg/kg (calculated dose in half tablet increments) if the animals are dogs. Animals should observed daily for at least 30 days post-challenge for mortality or for progressive neurological signs indicative of rabies infection. Animals with progressive neurological signs will be humanely euthanized according to accepted procedures. Core brain samples will be harvested immediately after death or euthanasia from all animals. Blood collection after challenge may be collected at time of euthanasia under anesthesia, via intracardiac stick. Blood may be processed for serum, divided into two aliquots (2-3 ml/each) and the serum stored frozen (~−20° C.) until testing. A core sample from the medulla oblongata may be collected from all animals that die or are euthanized during the post-challenge period and any surviving animals euthanized at study termination. Samples may be shipped fresh on ice or frozen on dry ice to the testing facility. Serum rabies antibody titer may be quantified using a Rapid Fluorescent Focus Inhibition Test (RFFIT) or a Fluorescent Antibody Virus Neutralization (FAVN) Assay, and brain tissue from the study animals may be subjected to direct immunofluorescent staining of anti-rabies monoclonal antibody.

It should be understood by one of skill in the art that the disclosure herein is provided by way of example and the present invention is not limited thereto. From the disclosure herein and the knowledge in the art, the skilled artisan can determine the number of administrations, the administration route, and the doses to be used for each injection protocol, without any undue experimentation.

The present invention contemplates at least one administration to an animal of an efficient amount of the therapeutic composition made according to the invention. The animal may be male, female, pregnant female and newborn. This administration may be via various routes including, but not limited to, intramuscular (IM), intradermal (ID) or subcutaneous (SC) injection or via intranasal or oral administration. The therapeutic composition according to the invention can also be administered by a needleless apparatus (as, for example with a Pigjet, Dermojet, Biojector, Avijet (Merial, Ga., USA), Vetjet or Vitajet apparatus (Bioject, Oregon, USA)). Another approach to administering plasmid compositions is to use electroporation (see, e.g. Tollefsen et al., 2002; Tollefsen et al., 2003; Babiuk et al., 2002; PCT Application No. WO99/01158). In another embodiment, the therapeutic composition is delivered to the animal by gene gun or gold particle bombardment. In an advantageous embodiment, the animal is a dog, ferret or seal.

In one embodiment, the invention provides for the administration of a therapeutically effective amount of a formulation for the delivery and expression of a Rabies antigen or epitope in a target cell. Determination of the therapeutically effective amount is routine experimentation for one of ordinary skill in the art. In one embodiment, the formulation comprises an expression vector comprising a polynucleotide that expresses a Rabies antigen or epitope and a pharmaceutically or veterinarily acceptable carrier, vehicle or excipient. In another embodiment, the pharmaceutically or veterinarily acceptable carrier, vehicle or excipient facilitates transfection or infection and/or improves preservation of the vector or protein in a host.

Another embodiment of the invention is a kit for performing a method of eliciting or inducing an immunological or protective response against Rabies in an animal comprising a recombinant Rabies G immunological composition or vaccine and instructions for performing the method of delivery in an effective amount for eliciting an immune response in the animal.

In an embodiment, the subject matter disclosed herein is directed to a kit for performing a method of eliciting or inducing an immune response which may comprise any one of the recombinant Rabies compositions or vaccines, inactivated Rabies compositions or vaccines, recombinant Rabies viral compositions or vaccines, or plasmid-based Rabies compositions or vaccines, and instructions for performing the method, Another embodiment of the invention is a kit for performing a method of inducing an immunological or protective response against Rabies in an animal comprising a composition or vaccine comprising a Rabies polypeptide or antigen of the invention and a recombinant Rabies viral composition or vaccine, and instructions for performing the method of delivery in an effective amount for eliciting an immune response in the animal.

Another embodiment of the invention is a kit for performing a method of inducing an immunological or protective response against Rabies in an animal comprising a composition or vaccine comprising a recombinant Rabies viral vector of the invention and an inactivated Rabies immunological composition or vaccine, and instructions for performing the method of delivery in an effective amount for eliciting an immune response in the animal.

Another embodiment of the invention is a kit for performing a method of inducing an immunological or protective response against Rabies in an animal comprising a composition or vaccine comprising a recombinant Rabies viral vector of the invention and a plasmid-based Rabies composition or vaccine, and instructions for performing the method of delivery in an effective amount for eliciting an immune response in the animal.

Yet another aspect of the present invention relates to a kit for prime-boost vaccination according to the present invention as described above. The kit may comprise at least two vials: a first vial containing a vaccine or composition for the prime-vaccination according to the present invention, and a second vial containing a vaccine or composition for the boost-vaccination according to the present invention. The kit may advantageously contain additional first or second vials for additional prime-vaccinations or additional boost-vaccinations.

In one embodiment, the invention provides for the administration of a therapeutically effective amount of a formulation for the delivery and expression of a Rabies G polypeptide or antigen or epitope in a target cell. Determination of the therapeutically effective amount is routine experimentation for one of ordinary skill in the art. In one embodiment, the formulation comprises an expression vector comprising a polynucleotide that expresses a Rabies G polypeptide or antigen or epitope and a pharmaceutically or veterinarily acceptable carrier, vehicle or excipient. In another embodiment, the pharmaceutically or veterinarily acceptable carrier, vehicle or excipient facilitates transfection or infection and/or improves preservation of the vector or protein.

The pharmaceutically or veterinarily acceptable carriers or vehicles or excipients are well known to the one skilled in the art. For example, a pharmaceutically or veterinarily acceptable carrier or vehicle or excipient can be a 0.9% NaCl (e.g., saline) solution or a phosphate buffer. Other pharmaceutically or veterinarily acceptable carrier or vehicle or excipients that can be used for methods of this invention include, but are not limited to, poly-(L-glutamate) or polyvinylpyrrolidone. The pharmaceutically or veterinarily acceptable carrier or vehicle or excipients may be any compound or combination of compounds facilitating the administration of the vector (or protein expressed from an inventive vector in vitro); advantageously, the carrier, vehicle or excipient may facilitate transfection and/or improve preservation of the vector (or protein). Doses and dose volumes are herein discussed in the general description and can also be determined by the skilled artisan from this disclosure read in conjunction with the knowledge in the art, without any undue experimentation.

The cationic lipids containing a quaternary ammonium salt which are advantageously but not exclusively suitable for plasmids, are advantageously those having the following formula:

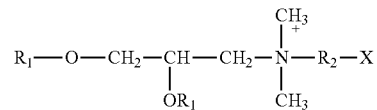

in which R1 is a saturated or unsaturated straight-chain aliphatic radical having 12 to 18 carbon atoms, R2 is another aliphatic radical containing 2 or 3 carbon atoms and X is an amine or hydroxyl group, e.g. the DMRIE. In another embodiment the cationic lipid can be associated with a neutral lipid, e.g. the DOPE.

Among these cationic lipids, preference is given to DMRIE (N-(2-hydroxyethyl)-N,N-dimethyl-2,3-b is (tetradecyloxy)-1-propane ammonium; WO96/34109), advantageously associated with a neutral lipid, advantageously DOPE (dioleoyl-phosphatidyl-ethanol amine; Behr, 1994), to form DMRIE-DOPE.

When DOPE is present, the DMRIE:DOPE molar ratio is advantageously about 95:about 5 to about 5:about 95, more advantageously about 1:about 1, e.g., 1:1.

Among the type (1) adjuvant polymers, preference is given to polymers of crosslinked acrylic or methacrylic acid, especially crosslinked by polyalkenyl ethers of sugars or polyalcohols. These compounds are known under the name carbomer (Pharmeuropa, vol. 8, no. 2, June 1996). One skilled in the art can also refer to U.S. Pat. No. 2,909,462, which provides such acrylic polymers crosslinked by a polyhydroxyl compound having at least three hydroxyl groups, preferably no more than eight such groups, the hydrogen atoms of at least three hydroxyl groups being replaced by unsaturated, aliphatic radicals having at least two carbon atoms. The preferred radicals are those containing 2 to 4 carbon atoms, e.g. vinyls, allyls and other ethylenically unsaturated groups. The unsaturated radicals can also contain other substituents, such as methyl. Products sold under the name Carbopol (BF Goodrich, Ohio, USA) are especially suitable. They are crosslinked by allyl saccharose or by allyl pentaerythritol. Among them, reference is made to Carbopol 974P, 934P and 971P.

As to the maleic anhydride-alkenyl derivative copolymers, preference is given to EMA (Monsanto), which are straight-chain or crosslinked ethylene-maleic anhydride copolymers and they are, for example, crosslinked by divinyl ether. Reference is also made to J. Fields et al., 1960.

With regard to structure, the acrylic or methacrylic acid polymers and EMA are preferably formed by basic units having the following formula:

$$----\underset{\underset{COOH}{|}}{\overset{\overset{R_1}{|}}{C}}-(CH_2)_x-\underset{\underset{COOH}{|}}{\overset{\overset{R_2}{|}}{C}}-(CH_2)_y----$$

in which:
  R1 and R2, which can be the same or different, represent H or CH3
  x=0 or 1, preferably x=1
  y=1 or 2, with x+y=2.
  For EMA, x=0 and y=2 and for carbomers x=y=1.

These polymers are soluble in water or physiological salt solution (20 g/l NaCl) and the pH can be adjusted to 7.3 to 7.4, e.g., by soda (NaOH), to provide the adjuvant solution in which the expression vector(s) can be incorporated. The polymer concentration in the final immunological or vaccine composition can range between about 0.01 to about 1.5% w/v, about 0.05 to about 1% w/v, and about 0.1 to about 0.4% w/v.

Other cytokines that may be used in the present invention include, but are not limited to, granulocyte colony stimulating factor (G-CSF), granulocyte/macrophage colony stimulating factor (GM-CSF), interferon α (IFNγ), interferon β (IFNβ), interferon γ, (IFNγ), interleukin-1α (IL-1α), interleukin-1β (IL-1β), interleukin-2 (IL-2), interleukin-3 (IL-3), interleukin-4 (IL-4), interleukin-5 (IL-5), interleukin-6 (IL-6), interleukin-7 (IL-7), interleukin-8 (IL-8), interleukin-9 (IL-9), interleukin-10 (IL-10), interleukin-11 (IL-11), interleukin-12 (IL-12), tumor necrosis factor α (TNFα), tumor necrosis factor 13 (TNFβ), and transforming growth factor β (TGFβ). It is understood that cytokines can be co-administered and/or sequentially administered with the immunological or vaccine composition of the present invention. Thus, for instance, the vaccine of the instant invention can also contain an exogenous nucleic acid molecule that expresses in vivo a suitable cytokine, e.g., a cytokine matched to this host to be vaccinated or in which an immunological response is to be elicited (for instance, a canine cytokine for preparations to be administered to canine).

The invention will now be further described by way of the following non-limiting examples.

Example 1

Construction of Recombinant vCP3006, Expressing Four Copies of Rabies Virus Glycoprotein An ALVAC recombinant virus was produced in which a synthetic Rabies G gene has been inserted into the C3 loci (2 copies) in the background of vCP65a carrying a classic Rabies virus G in the C5 loci (2 copies).

Summary.

Figure 1:
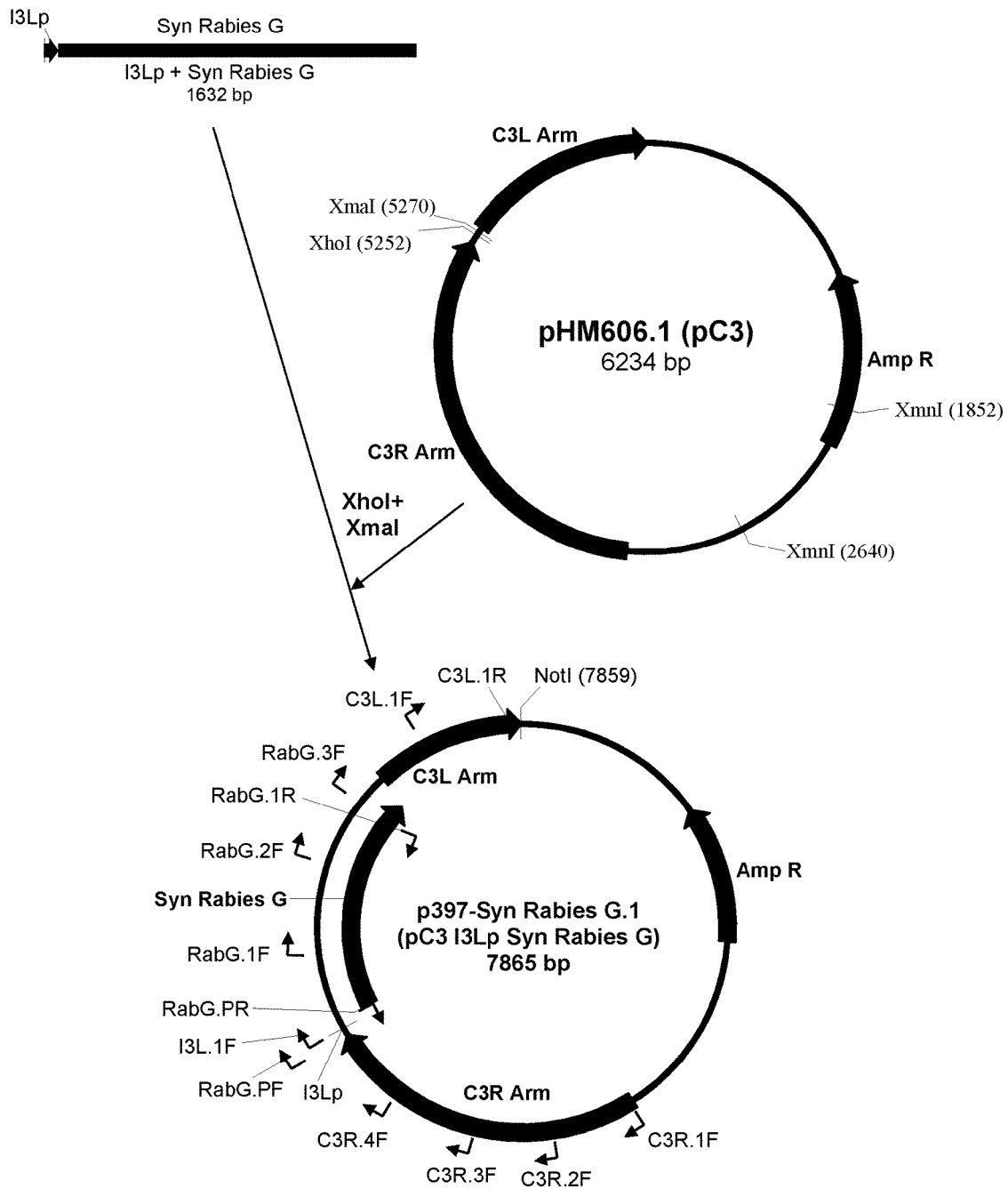

A synthetic codon-optimized Rabies virus G (SEQ ID NO:1) was inserted into the C3 loci of a parental canarypox virus (ALVAC CP65a [as fully described in U.S. Pat. No. 5,843,456, to Virogenetics], having a titer of 6.1×10E7 pfu/mL, resuspended in 1 mL Tris pH9 buffer). Parental ALVAC, which was used to produce the CP65a, was deposited on Nov. 14, 1996 under the terms of the Budapest Treaty with the ATCC, accession number VR-2547. Thus, a skilled person in the art is fully expected to be able to make and use the CP65a of U.S. Pat. No. 5,843,456, or a reasonable/functional substitute thereof. The protein sequence of the codon-optimized rabies virus G was 100% identical to GenBank ACR15154.1 (SEQ ID NO:1). The donor plasmid comprised synthetic Rabies G gene (SEQ ID NO:5) and I3L promoter (SEQ ID NO:4) in C3 loci plasmid (p397-Syn Rabies G, FIG. 1). The donor plasmid was made by taking a ~1.6 kb XhoI-XmaI with I3L-Synthetic Rabies G PCR fragment and cloning it into pHM606.1 (pC3), generating p397-Syn Rabies G (pC3 I3Lp Syn Rabies G, FIG. 1). In vitro recombination was carried out in primary chicken embryo fibroblast (1° CEF) cells.

Generation of Recombinant vCP3006.

Figure 2:
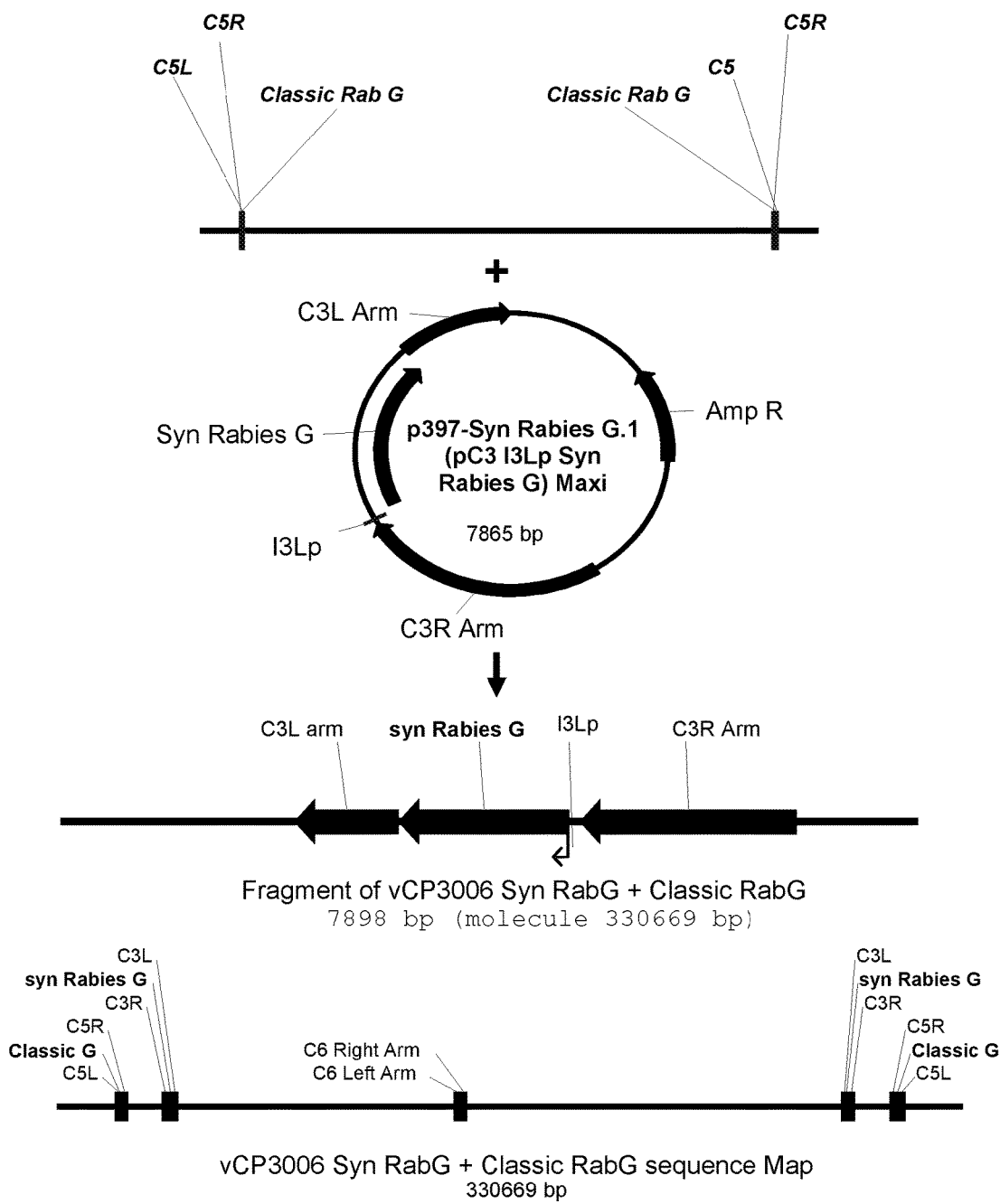
Figure 3:
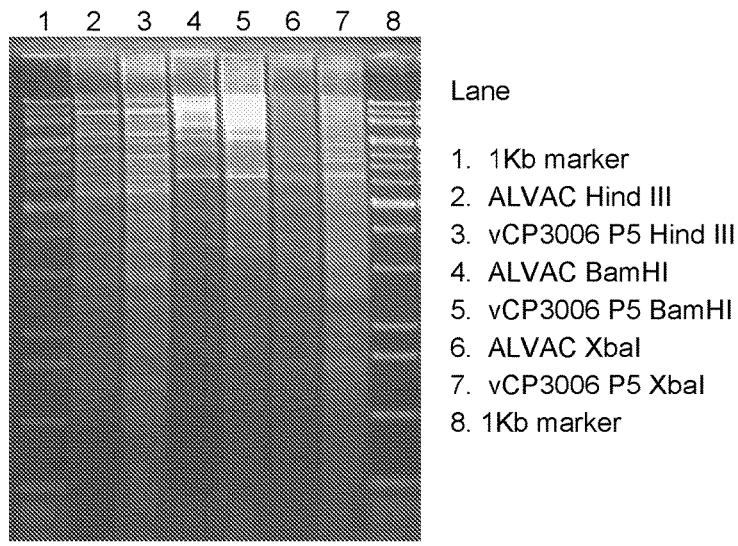
Figure 4:
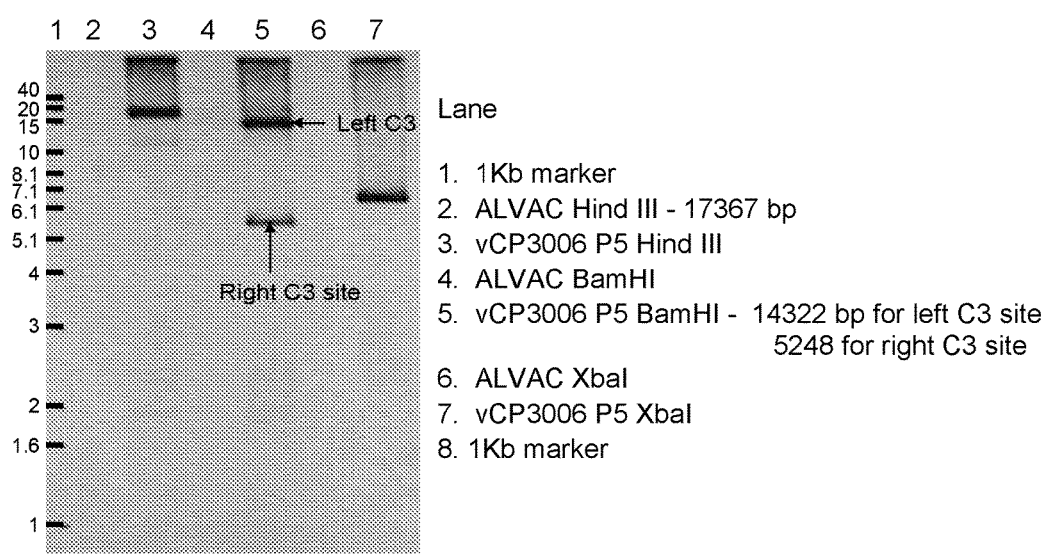
Figure 5:
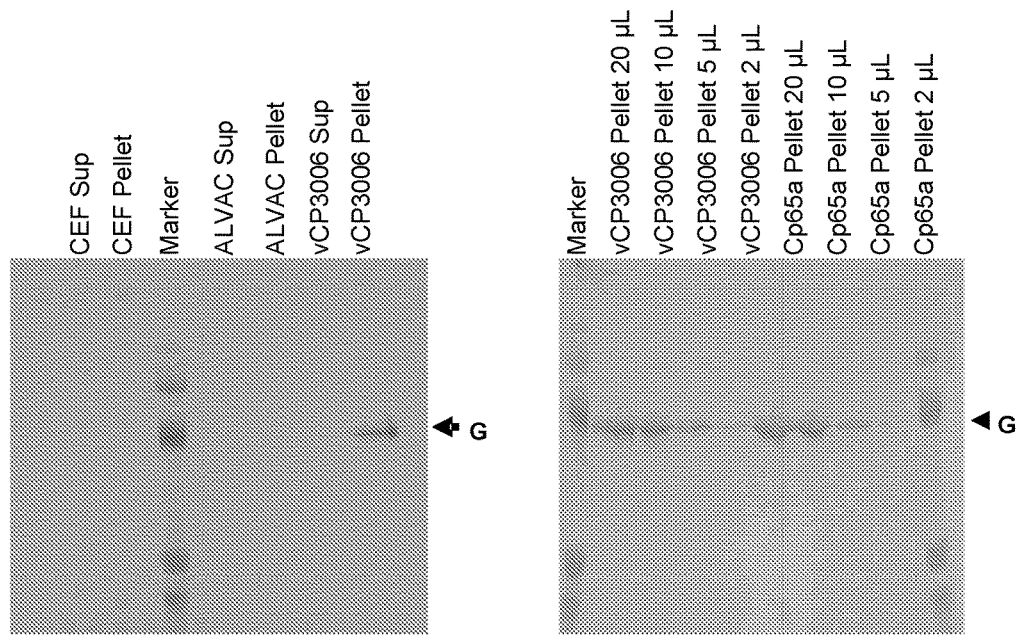
Figure 6:
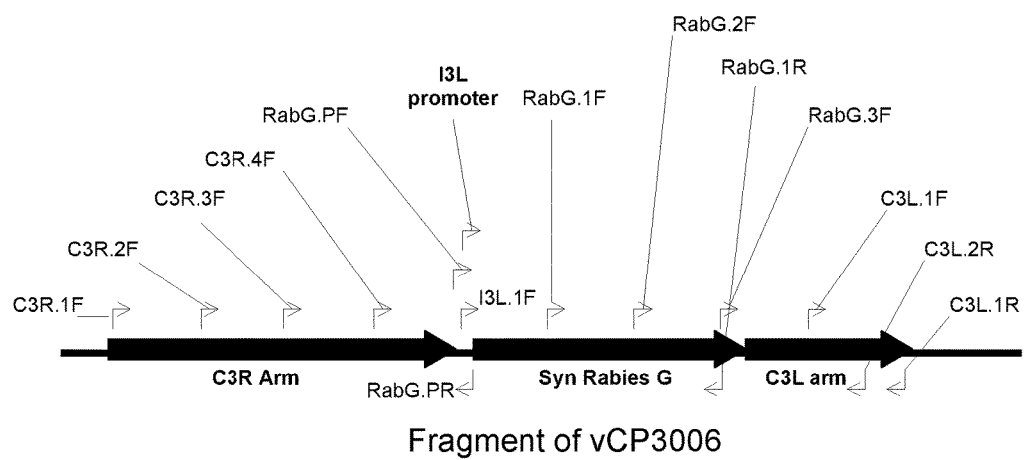

To initiate an in vitro recombination (IVR), first 1° CEF cells were transfected with 20 µg of Not I-digested plasmid p397-Syn Rabies G using FuGENE-6® reagent (Roche). The transfected cells were subsequently infected with ALVAC CP65a Stock at MOI of 10. After 24 hr, the transfected-infected cells were harvested, sonicated and used for recombinant virus screening. Recombinant plaques were screened based on the plaque lift hybridization method using a 140 base pair (bp) unique I3L probe (FIG. &) labeled with North2South Biotin Random Prime Labeling Kit (Thermo Scientific#17075) and detected with North2South Chemiluminescent Hybridization and Detection Kit (Thermo Scientific#17097). After five sequential rounds of plaque purification, a recombinant designated as vCP3066.4.1.3.1.1.3 was generated. A single plaque was selected from the 6$^{th}$ round of plaque purification and expanded to P1 (1×T25), P2 (1 well in a 6-well plate), P3 (1 well in a 6-well plate), P4 (1×T75 flask), and P5. Infected cells from P5 roller bottles were harvested and concentrated to produce vCP3006 stock. A schematic representation of vCP3006 generation is shown in FIG. 2.

Analysis of vCP3006.

Verification of genetic purity was done on the P5 stock using synthetic Rabies G and C3 site probes for hybridization. For Southern blot hybridization, genomic DNA was extracted from vCP3006 P5, digested with Xba I, Hind III, and BamHI, and separated by agarose electrophoresis. The digested genomic DNA was transferred to nylon membrane and subjected to Southern blot analysis by probing with a synthetic Rabies G specific probe. Primers RabG.1F (SEQ ID NO:52) and RabG.1R (SEQ ID NO:53) were used to amplify the synthetic Rabies G-specific probe.

Western Blot.

Primary CEF cells were infected with P5 stock at MOI of 4.5 and incubated at 37° C. for 24 hrs. For comparison of the G expression level, cells were also infected with the parental vCP65a using the same multiplicity of infection. The cells and culture supernatant were then harvested. Sample proteins were separated on a 10% SDS-PAGE gel, transferred to PVDF membrane. The membrane was incubated with mouse anti-Rabies G MAb (Chemicon #MAB8727) at a dilution of 1:500 followed by alkaline phosphatase conjugated anti-Mouse antibody.

Sequence Analysis.

A more detailed analysis of the P5 stock genomic DNA was performed by PCR amplification and sequence analysis of the flanking arms of the C3 locus and the synthetic Rabies G insert. Primers C3R.3F (SEQ ID NO:44) and C3L.1R (SEQ ID NO:47), located in the arms of the C3 locus in the ALVAC genome, were used to amplify the entire C3L-Syn Rabies G-C3R fragment (SEQ ID NO:2), and primers shown in FIG. 37 were then used to sequence the fragment.

Results.

The homogeneity of the P5 stock of vCP3006 was confirmed by hybridization as 100% positive for the synthetic Rabies G and 100% negative for the C3 site. The titer of the P5 stock vCP3006 virus was $1.88\times10^9$ pfu/ml. The genomic integrity of recombinant vCP3006 was also verified by Southern blot analysis after separation of restriction enzyme digested genomic DNA in a gel electrophoresis (FIG. 3). Southern blot analysis using synthetic Rabies G specific probe revealed bands of expected sizes (14322 bp and 5248 bp BamHI, 17367 bp HindIII, and 6293 bp XbaI; FIG. 4), demonstrating the correct insertion of synthetic Rabies G into the C3 loci. The two bands on lane 5 (FIG. 4) also confirms insertion of synthetic rabies G into both sites of C3 (14322 bp for left C3 site and 5248 bp for right C3 site).

For expression analysis of rabies virus G, primary CEF cells were infected with P5 stock of vCP3006 or vCP65a at MOI of 4.5. Supernatant as well as infected cell samples were processed and subjected to Western blot analysis. As shown in FIG. 5, rabies virus G was detectable in infected cell pellet, but not in supernatant samples, suggesting that G is not incorporated to ALVAC virions at a detectable level (FIG. 5 left). As the anti-rabies monoclonal recognizes both the classical G and the additional codon-optimized G in vCP3006, an attempt was done to compare the amount of G expressed vCP65a to that of vCP3006. For this purpose, cells were infected at similar MOI and different amounts of the total cell lysates were subjected to Western blot analysis (FIG. 5, right). Comparing the respective lanes loaded with 2 μl of cell lysates, it appears that the G band from vCP3006 is more abundant than the respective lane of vCP65a. This suggests that, vCP3006 expresses more G than does vCP65a. A PCR product covering flanking arms of the C3 locus and the synthetic Rabies G insert was sequenced using primers shown in FIG. 6 (full descriptions of which are presented in FIG. 37). The sequence analysis demonstrated that the sequences of the synthetic Rabies G and C3L and C3R regions were as expected (FIG. 7), and the entire C3L to C3R fragment has the sequence as set forth in SEQ ID NO: 2. The predicted synthetic Rabies G peptide sequence is presented in FIG. 8 (SEQ ID NO:1), and is identical to the wild type Rabies G peptide sequence.

Example 2

Construction of Recombinant vCP3015, Co-Expressing Rabies Virus Glycoprotein and OX40L Summary.

Generation and characterization ALVAC recombinant in which a canine OX40 ligand (cOX40L) has been inserted into the C6 locus (one copy) in the background of vCP65a carrying a classic Rabies virus G in the C5 loci (2 copies). A codon-optimized synthetic canine OX40 Ligand (cOX40L, tumor necrosis factor ligand superfamily member 4-like) was inserted into the C6 locus of parental virus ALVAC CP65a (titer 6.1×10e7 pfu/mL, resuspended in 1 mL Tris pH9 buffer). The donor plasmid was p397-cOX40L (pC6 42 Kp cOX40L) a synthetic cOX40L with 42K promoter in C6 locus, and was produced by taking a ~0.6 kb EcoRI-XmaI synthetic canine OX40L fragment with 42K promoter and cloning into pC6L (FIG. 9). In vitro recombination was carried out in primary 1° CEF cells, according to procedure disclosed in Example 1. Screening of recombinant plaques was essentially done as described under Example 1 using a 551 bp cOX40L-specific probe. After four sequential rounds of plaque purification, the recombinant designated as vCP3015.9.2.1.2 was generated. Single plaques were selected from the 4$^{th}$ round of plaque purification, and expanded to obtain P1 (T-25 flask), P2 (T-75 flask) and P3 (4 roller bottles) of vCP3015.9.2.1.2. P3 was harvested, infected CEFs pelleted, and supernatant removed. The infected CEFs were resuspended in 1 mM Tris, pH 9.0, sonicated, and concentrated to produce virus stock of vCP3015. A schematic representation of vCP3015 generation is shown in FIG. 10.

Analysis of vCP3015.

Genomic DNA from P3 of vCP3015 was extracted, digested with NruI, and run in duplicate on a 0.8% agarose gel. The NruI digested genomic DNA was transferred to nylon membrane and Southern Blot analysis was essentially performed as described under Example 1 by probing either with cOX40L or classic Rabies G probes. PCR primers OX40L.1F (SEQ ID NO:61) and OX40L.1R (SEQ ID NO:62) were used to amplify a cOX40L probe, and primers CP65.2R (SEQ ID NO:39) and C5R.3F (SEQ ID NO:30) were used to amplify classical rabies virus G probe.

Western Blot.

Primary CEF cells were infected with P3 stock of vCP3015 at MOI of 10 and incubated at 37° C. for 26 hrs. The cells and culture supernatant were then harvested. Sample proteins were separated on a 10% SDS-PAGE gel, transferred to PVDF membrane, and probed with a monoclonal anti-Rabies G antibody (Chemicon #MAB8727) at a dilution of 1:500 followed by alkaline phosphatase conjugated anti-Mouse antibody.

Sequence Analysis.

For the classic Rabies G at the C5 site, a detailed analysis of the P3 stock genomic DNA was performed by PCR amplification and sequence analysis of the C5 locus containing the classic Rabies G insert. Primers 7635CXL.R (SEQ ID NO:35) and 7635CXL.F (SEQ ID NO:36), located at the end of the arms of the C5 locus were used to amplify the entire C5R-classic Rabies G-C5L fragment. The fragment was then sequenced using the primers listed in FIG. 37. For cOX40L at C6, a detailed analysis of the P3 stock genomic DNA was performed by PCR amplification and sequence analysis of the C6 locus containing the cOX40L insert. Primers C6R.1F (SEQ ID NO:57) and C6L.1R (SEQ ID NO:60), located at the end of the arms of the C6 locus were used to amplify the entire C6R-cOX40L-C6L fragment. The fragment was sequenced using the primers listed in FIG. 37.

Results.

Figure 11:
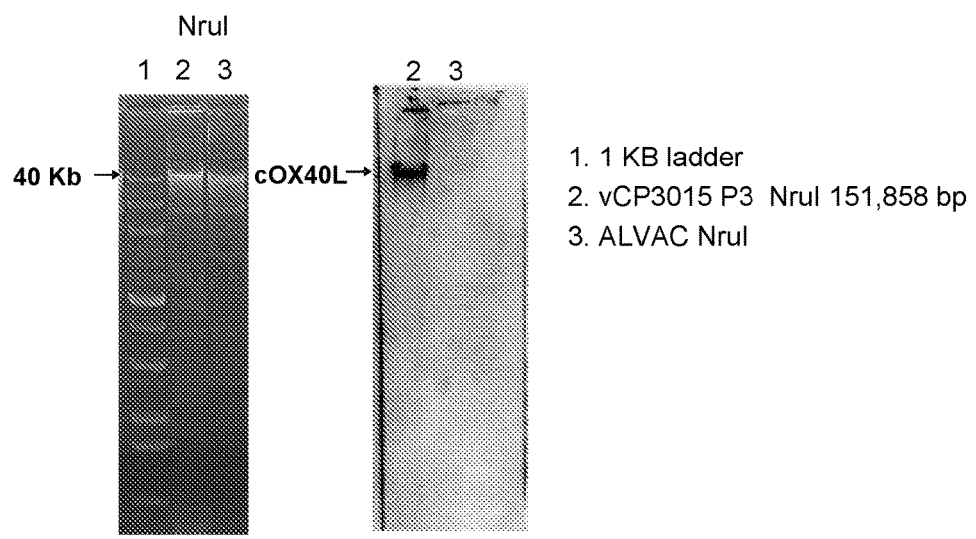
Figure 12:
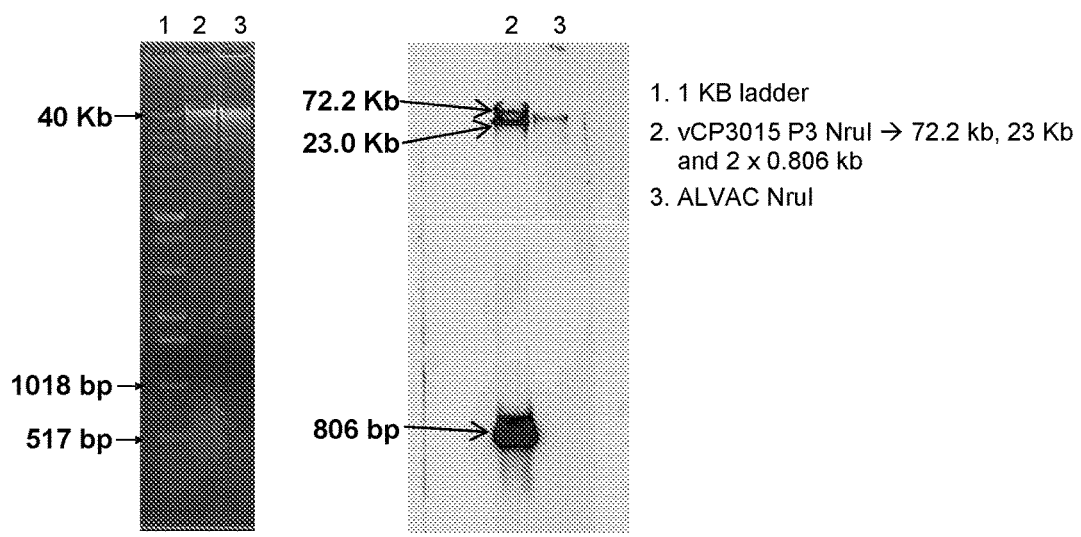

The homogeneity of the P3 stock of vCP3015 was confirmed by hybridization as 100% positive for the cOX40L insert and 100% negative for the empty C6 site. The titer of the P3 stock vCP3015 virus was $8.5 \times 10^9$ pfu/ml. The genomic integrity of recombinant vCP3015 was also verified by Southern blot. For cOX40L, the probe detected a 151,858 bp fragment (FIG. 11) and for classic Rabies G, the probe detected a 72,175 bp fragment for the left C5 site, a 23,014 bp fragment for the right C5 site, and an 806 bp fragment for both C5 sites (FIG. 12).

Figure 13:
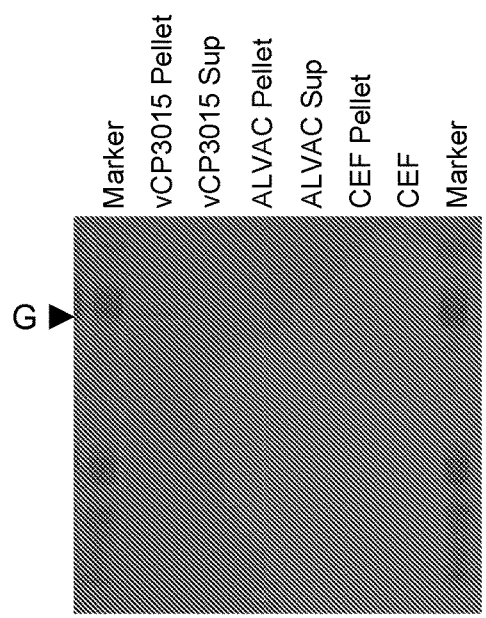
FIG. 13 is a Western blot analysis of vCP3015. A band corresponding to rabies virus G could only be detected in the pellet from cells infected with vCP3015.
Figure 14:
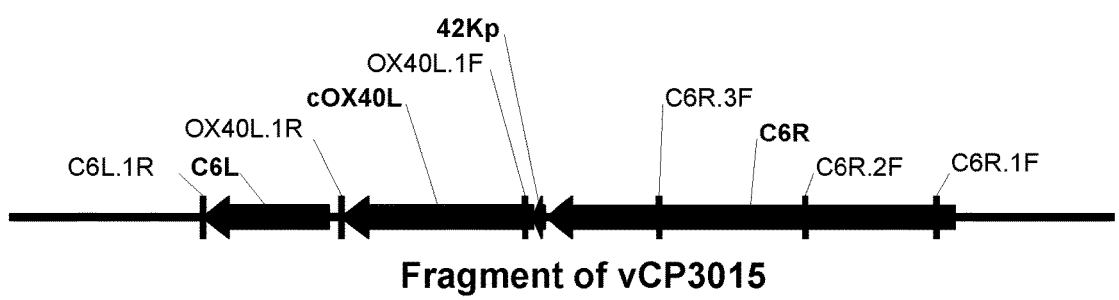
FIG. 14 is s schematic drawing of the vCP3015 C6 region showing primer locations.

For expression analysis of classical rabies virus G, primary CEF cells infected with P3 stock of vCP3015 at MOI of 10. Supernatant as well as infected cell samples were processed and subjected to Western blot analysis. As shown in FIG. 13, rabies virus G was detectable in infected cell pellet at the expected size, but not in supernatant samples. A PCR product covering flanking arms of the C6 locus and the cOX40L insert was sequenced using primers shown in FIG. 14. The sequence analysis demonstrated that the sequences of the cOX40L and C6L and C6R regions are as expected (FIG. 15). A PCR product covering flanking arms of the C5 locus and the classical rabies virus G insert was sequenced using primers shown in FIG. 17. The resultant sequence is shown in FIG. 18 (SEQ ID NO:13).

Example 3

Construction of Recombinant vCP3012, Co-Expressing Classical Rabies Virus G, Codon-Optimized Rabies Virus G and OX40L Summary.

Figure 9:
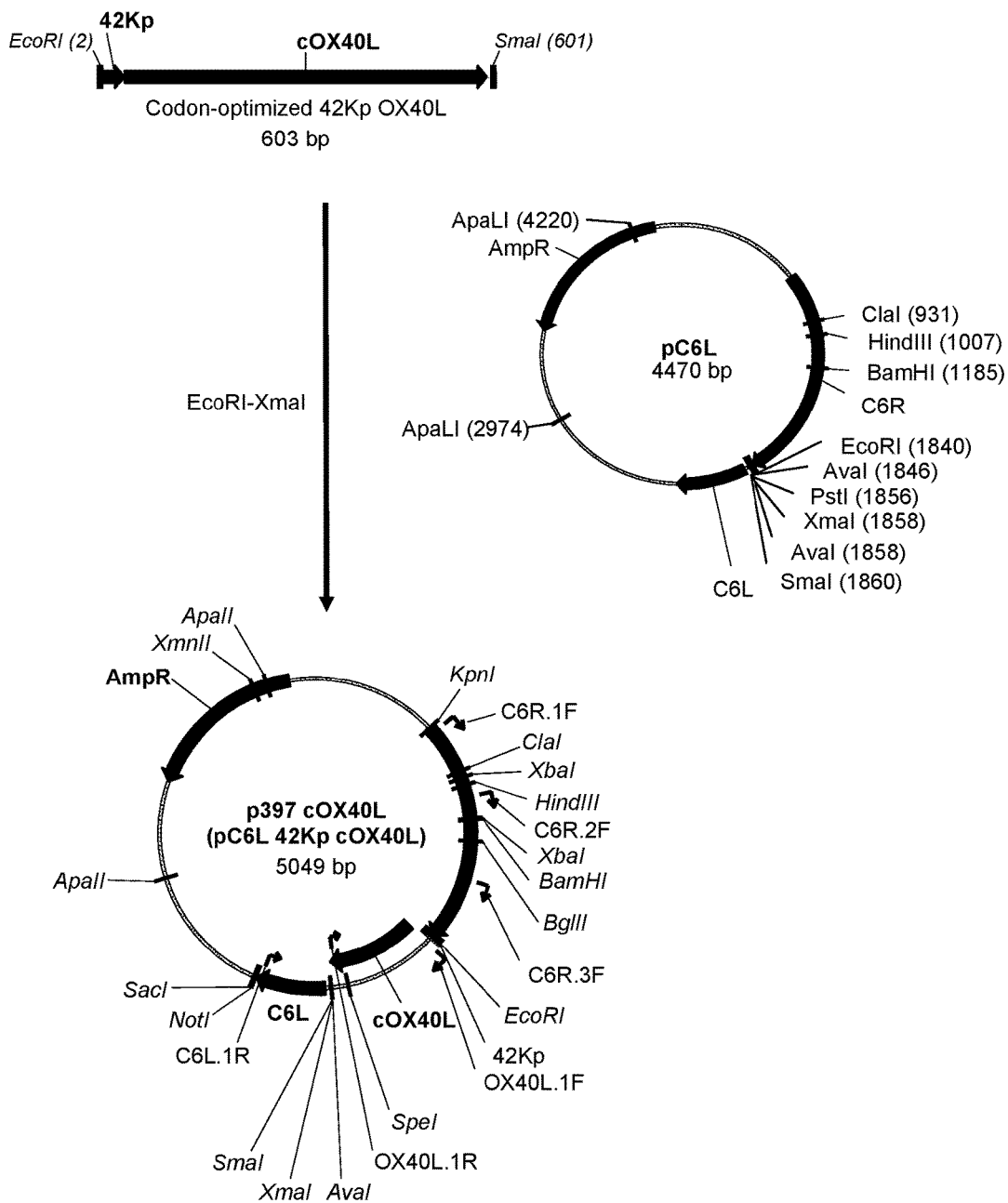

Generation and characterization ALVAC recombinant in which a canine OX40 ligand (cOX40L) has been inserted into the C6 locus (one copy) in the background of vCP3006 carrying classic rabies virus G in the C5 loci (2 copies) and codon-optimized rabies virus G in the C3 loci (2 copies). Codon-optimized synthetic canine OX40L sequence (led by 42K promoter) was inserted into the C6 locus of parental virus ALVAC vCP3006 P5 (stock titer was $1.88 \times 10^9$ pfu/ml). The donor plasmid 397-cOX40L (pC6 42 Kp cOX40L) was identical to that used in Example 2 in FIG. 9, as was the in vitro recombination method.

Screening of recombinant plaques was essentially done as described in Example 1 using a 551 bp cOX40L-specific probe. After 4 sequential rounds of plaque purification, the recombinant designated as vCP3012.9.2.1.3 was generated. Single plaques were selected from the final round of plaque purification, and expanded to obtain P1 (6 well plate), P2 (T-75 flask) and P3 (roller bottle) stocks to amplify vCP3012.9.2.1.3. The infected cells as well as the culture supernatant from the roller bottles was harvested and pelleted. After removing the supernatant, the pellet was sonicated and concentrated to produce vCP3012 stock virus.

Analysis of vCP3012.

Genomic DNA was extracted from vCP3012 (P3), digested with PmeI, NruI, and BamHI, and separated by agarose electrophoresis. The digested genomic DNA was transferred to nylon membrane and Southern blot analysis was essentially performed as described under example 1 bp probing with cOX40L, synthetic rabies G, and classic rabies G probes. PCR primers OX40L.1F (SEQ ID NO:61) and OX40L.1R (SEQ ID NO:62) were used to amplify cOX40L probe, primers CP65.2R (SEQ ID NO:39) and C5R.3F (SEQ ID NO:30) were used to amplify classical rabies virus G probe, and primers RabG.1R (SEQ ID NO:53) and RabG.1F (SEQ ID NO:52) were used to amplify synthetic rabies virus.

Western blot.

Primary CEF cells were infected with P3 stock of vCP3012 at MOI of 10 and incubated at 37° C. for 24 hrs. The cells and culture supernatant were then harvested. Sample proteins were separated on a 10% SDS-PAGE gel, transferred to PVDF membrane. The membrane was incubated with a monoclonal anti-Rabies G antibody (Chemicon #MAB8727) at a dilution of 1:500 followed by alkaline phosphatase conjugated anti-Mouse antibody.

Sequence Analysis.

For cOX40L at C6, analysis of the P3 stock genomic DNA was performed by PCR amplification and sequence analysis of the C6 locus containing the cOX40L insert. Primers C6R.1F (SEQ ID NO:57) and C6L.1R (SEQ ID NO:60), located at the end of the arms of the C6 locus were used to amplify the entire C6R-cOX40L-C6L fragment. The fragment was sequenced using the primers listed in FIG. 37. For Synthetic Rabies G at C3, analysis of the P3 stock genomic DNA was performed by PCR amplification and sequence analysis of the flanking arms of the C3 locus and the synthetic rabies G insert. Primers C3R.2F (SEQ ID NO:43) and C3L.1R (SEQ ID NO:47) located at the arms of the C3 locus were used to amplify the entire C3R-Syn Rabies G insert-C3L fragment. For classic Rabies G at C5, analysis of the P3 stock genomic DNA was performed by PCR amplification and sequence analysis of the C5 locus containing the classic Rabies G insert. Primers 7635CXL.R (SEQ ID NO:35) and 7635CXL.F (SEQ ID NO:36), located at the end of the arms of the C5 locus were used to amplify the entire C5R-classic Rabies G-C5L fragment. The fragment was sequenced using the primers listed in FIG. 37.

Results.

The homogeneity of the P3 stock of vCP3012 was confirmed by hybridization as 100% positive for the cOX40L insert and 100% negative for the empty C6 site. The titer of the P3 stock of vCP3012 virus was $4 \times 10^9$ pfu/ml. The genomic integrity of recombinant vCP3012 was also verified by Southern blot. For cOX40L, the probe detected a 200.362 bp fragment (FIG. 21); for synthetic rabies G, 14322 bp for the left C3 site and 5248 bp for right C3 site (FIG. 22); and for classic rabies G 806 bp for both sites, 72,436 bp for the left C5 site and 23,275 bp for the right C5 site (FIG. 23). These expected sizes indicated the correct insertion of cOX40L at the C6 locus, synthetic rabies G at the C3 loci, and classic Rabies G at the C5 loci.

For expression analysis of classical as well as synthetic rabies virus G, primary CEF cells infected with P3 stock of vCP3012 at MOI of 10. Supernatant as well as infected cell samples were processed and subjected to Western blot analysis. As shown in FIG. 24, rabies virus G was detectable in infected cell pellet at the expected size.

A PCR product covering flanking arms of the C6 locus and the cOX40L insert was sequenced using primers shown in FIG. 25. The sequence analysis demonstrated that the sequences of the cOX40L and C6L and C6R regions are as expected (FIG. 26). A PCR product covering flanking arms of the C3 locus and the synthetic rabies virus G insert was sequenced using primers shown in FIG. 27. The resultant sequence is shown in FIG. 28 (SEQ ID NO:20). The results showed that the sequences of the synthetic Rabies G insert and the C3 left and right arms around the synthetic rabies G insert in vCP3012 were as expected. A PCR product covering flanking arms of the C5 locus and the classical rabies virus G insert was sequenced using primers shown in FIG. 29. The resultant sequence is shown in FIG. 30 (SEQ ID NO:23). The results showed that the sequences of the classical Rabies G insert and the C5 left and right arms around the classical rabies G insert in vCP3012 were as expected.

Example 4

Efficacy Evaluation of Three New Recombinant Canarypox Vaccines in Comparison to vCP65A by Vaccination and Serology in Dogs For this study, all dogs were randomly assigned to five different treatment groups (6 dogs in each group) with factor of litter ID. Dogs from the different vaccine groups were randomly assigned to pens with vaccine groups commingled within the same pen. Dogs were assigned to pens segregated by sex. Dogs in the control group will be housed in a different pen from the vaccinates during the pre-challenge period. SAS® software V9.1 Enterprise Guide was used for producing the randomization table. Dogs were vaccinated on Day 0 with candidate vaccines (Table 1). Blood samples were taken on Day 0, 7, 14, 21, 28, 48, 70 and 90 and rabies antibody titers determined by RFFIT.

TABLE 1

Treatment Groups

| Groups | Vaccine | Vaccine target dose (TCID50/ml) | Route/Once | Volume | Dogs per Group |
|---|---|---|---|---|---|
| A | Test Vaccine #1 vCP3006 | $10^{5.9}$ | SQ | 1 ml | 6 |
| B | Test Vaccine #2 vCP3012 | $10^{5.9}$ | SQ | 1 ml | 6 |
| C | Test Vaccine #3 vCP3015 | $10^{5.9}$ | SQ | 1 ml | 6 |
| D | Reference vaccine vCP65A | $10^{5.9}$ | SQ | 1 ml | 6 |
| E (negative control) | — | — | — | — | 6 |

The geometric mean RFFIT titers and the 95% confidence intervals were calculated for each group (A, B, C, and D) and day. The antibody peak appears to be on day 21. The results are shown in Table 2. On day 14, vCP3012 vaccinates have markedly higher titers than all other groups. On Day 21, both groups vaccinated with a cOX40L containing canarypox vector have greater neutralizing responses than other vaccinated groups. Thus, an earlier onset of immunity and higher peak titers are clearly seen in groups vaccinated with a vector expressing cOX40L. After Day 21 and until the end of the study, vCP3012 vaccinates maintained markedly higher titers than all other groups. On Day 90, all of the dogs vaccinated with vCP3012 had titers greater than 0.5 IU/ml, a titer generally considered as protective in rabies virulent challenge experiments. Thus, cOX40L expression improves the duration of immunity of a canarypox vectored rabies vaccine.

Conclusion.

Compared to the parent vCP65a, the addition of cOX40L into the backbone of either vCP65a or vCP3006 clearly enhances the onset of anti-rabies immunity as measured by anti-rabies neutralizing antibodies; increases the peak anti-rabies neutralizing antibody titer as well as prolongs the duration of anti-rabies immunity for at least 90 days (the last date of blood sampling).

TABLE 2

Geometric Mean Titers and 95% confidence interval

| Day | Group | GMT | Lower 95% CI of GMT | Upper 95% CI of GMT |
|---|---|---|---|---|
| 7 | #1 vCP3006 | 0.57 | 0.30 | 1.08 |
|  | #2 vCP3012 | 0.61 | 0.34 | 1.10 |
|  | #3 vCP3015 | 0.47 | 0.23 | 0.95 |
|  | Ref vCP65A | 0.41 | 0.22 | 0.76 |
| 14 | #1 vCP3006 | 0.78 | 0.29 | 2.08 |
|  | #2 vCP3012 | 3.36 | 1.71 | 6.63 |
|  | #3 vCP3015 | 0.98 | 0.39 | 2.43 |
|  | Ref vCP65A | 0.54 | 0.27 | 1.08 |
| 21 | #1 vCP3006 | 0.68 | 0.36 | 1.30 |
|  | #2 vCP3012 | 4.84 | 3.53 | 6.64 |
|  | #3 vCP3015 | 1.97 | 0.76 | 5.10 |
|  | Ref vCP65A | 0.92 | 0.29 | 2.96 |
| 28 | #1 vCP3006 | 0.66 | 0.34 | 1.29 |
|  | #2 vCP3012 | 3.06 | 1.61 | 5.82 |
|  | #3 vCP3015 | 1.63 | 0.85 | 3.10 |
|  | Ref vCP65A | 1.15 | 0.36 | 3.65 |
| 48 | #1 vCP3006 | 0.55 | 0.32 | 0.95 |
|  | #2 vCP3012 | 1.81 | 0.77 | 4.25 |
|  | #3 vCP3015 | 1.06 | 0.60 | 1.90 |
|  | Ref vCP65A | 0.35 | 0.16 | 0.73 |
| 70 | #1 vCP3006 | 0.39 | 0.19 | 0.78 |
|  | #2 vCP3012 | 1.16 | 0.66 | 2.03 |
|  | #3 vCP3015 | 0.58 | 0.37 | 0.89 |
|  | Ref vCP65A | 0.26 | 0.13 | 0.49 |
| 90 | #1 vCP3006 | 0.40 | 0.21 | 0.76 |
|  | #2 vCP3012 | 0.96 | 0.54 | 1.70 |
|  | #3 vCP3015 | 0.48 | 0.28 | 0.82 |
|  | Ref vCP65A | 0.25 | 0.14 | 0.42 |

Example 5

Evaluation of the Immunogenicity of Three New Recombinant Canarypox Vaccines by Virulent Challenge in Dogs Thirty (30) two to three month-old, purpose-bred beagles were randomly allocated into one of five treatment groups (n=6), using litter ID as the primary randomization factor. On Day 0 all dogs were vaccinated according to Table 3 below.

TABLE 3

Vaccination scheme

| Groups | Vaccine* | Vaccine backtitration results (TCID$_{50}$/ml) | TCID$_{50}$ administered | Volume | Dogs per Group |
|---|---|---|---|---|---|
| A | Test Vaccine #1 vCP3006 | $10^{6.16}$ | $10^{6.16}$ | 1 ml | 6 |
| B | Test Vaccine #2 vCP3012 | $10^{6.54}$ | $10^{6.22}$ | 0.7 ml | 6 |
| C | Test Vaccine #3 vCP3015 | $10^{6.08}$ | $10^{5.87}$ | 1 ml | 6 |
| D | Reference vaccine vCP65A | $10^{6.12}$ | $10^{6.07}$ | 1 ml | 6 |
| E (− control) | — | — | — | — | 6 |

*Vaccine target titer $10^{5.9}$ TCID$_{50}$/ml.

Animals were monitored, for one hour post-vaccination for acute systemic reactions. Injection sites were examined and rectal temperatures recorded daily for 3 days thereafter. Blood was collected for rabies antibody titers as measured by Rapid Fluorescent Focus Inhibition Test (RFFIT) prior to, and at regular intervals following vaccination. Based on a favorable serological response, dogs from Group C (vCP3015) were subject to a virulent rabies challenge approximately one year after vaccination (Day 397). The challenge material (New York Strain 1 42.90 at a dilution of 1:100) was administered under anesthesia by the intramuscular route, into the left and the right frontalis muscles (0.5 ml into each muscle). Back titration of the challenge material was performed in accordance with QCD-CM-030. Post-challenge, dogs were observed for 30 days for mortality or evidence of progressive neurological signs. Serum was obtained from all dogs immediately after euthanasia for RFFIT testing. Both brain hemispheres were collected at necropsy and the right hemisphere was submitted for detection of rabies virus using direct immunofluorescence.

All statistical analyses were performed using SAS, Cary, N.C. (SAS Version 9.1, Enterprise Guide). All tests were two-sided and statistical significance was declared at a P value of 0.05 or less. The primary variable was serum rabies antibody titer as measured by Rapid Fluorescent Focus Inhibition Test (RFFIT). Seroconversion was defined as a change from a negative antibody titer (under detection threshold, i.e. ≤0.2 IU/ml) to a positive rabies antibody titer (>0.2 IU/ml). All dogs were seronegative for rabies prior to vaccination except for one dog in Group A (vCP3006) that presented with a low rabies titer of 0.3 IU/ml and a value of 0.5 IU/ml on a re-test. Three dogs from Group E (negative control group) demonstrated low antibody titers within 30 days of initiation of the study. By Day 48 all dogs in Group E were seronegative and remained negative throughout the study. The low rabies titers were almost certainly due to residual maternal antibodies. The Group Geometric Mean RFFIT antibody titer following vaccination for Groups A, B, C and D are shown in Table 4.

TABLE 4

Serum Rabies Ab Geometric Mean Titer (IU/ml) per Group following vaccination.

| Group | Day post-vaccination - RFFIT GMT IU/ml | | | | | | |
|---|---|---|---|---|---|---|---|
| | 7 | 14 | 21 | 28 | 48 | 70 | 90 |
| A vCP3006 | 0.57 | 0.78 | 0.68 | 0.66 | 0.55 | 0.39 | 0.40* |
| B vCP3012 | 0.61 | 3.36* | 4.84* | 3.06* | 1.81* | 1.16* | 0.96* |
| C vCP3015 | 0.47 | 0.98 | 1.97* | 1.63 | 1.06* | 0.58* | 0.48* |
| D vCP65A | 0.41 | 0.54 | 0.92 | 1.15 | 0.35 | 0.26 | 0.25 |
| E (−control) | 0.23 | 0.25 | 0.21 | 0.20 | 0.20 | 0.20 | 0.20 |

*GMT significantly (p < 0.05) and different from the reference vaccine (Group D vCP65A)

Seroconversion was observed for all dogs in Group B (vCP3012) and 5/6 dogs in Groups A (vCP3006), C (vCP3015) and D (vCP65A) seven days following vaccination. Dogs vaccinated with vCP3012 demonstrated a significantly and unpredictably higher rabies titer in comparison to Group A (vCP3006) and the reference vaccine group D (vCP65A) from Days 14 through Day 90. The rabies GMT for Group C (vCP3015) was significantly higher than the reference vaccine group D (vCP65A) on Days 21, 48, 70 and 90. Dogs vaccinated with vCP3006 did not show a significant difference in rabies titers in comparison to the reference vaccine Group D (vCP65A) except for Day 90.

Approximately one year after vaccination, dogs from Group C (vCP3015) were subjected to a virulent rabies challenge. The remaining dogs from Group B and E remained under the current study number until termination of the study at a later date. The calculated 50% mouse lethal dose ($MLD_{50}$) of the challenge virus administered was 2.2 $log_{10}$ (158.5 $MLD_{50}$) in 0.03 ml. As 1 ml was administered to each dog, the dog dose was 3.96 $log_{10}$ $MLD_{50}$. The pre- and post-challenge RFFIT titers, and post-challenge rabies fluorescent antibody results and morbidity/mortality data are shown in Table 5 below.

TABLE 5

Summary results

| Vaccine Group | ID | Serology RFFIT (IU/ml)* | | Rabies fluorescent antibody results Brain sample | Morbidity/ Mortality** |
|---|---|---|---|---|---|
| | | Pre-challenge (Day 392 post-vaccination)* | Post-challenge (day of euthanasia) | | Day of death post-challenge |
| Group C vCP3015 | CCECAC | ≤0.2 | 0.9 | Negative | 30 |
| | CCECAN | ≤0.2 | 0.7 | Negative | 30 |
| | CCECAV | 0.2 | 5.8 | Negative | 30 |
| | CCECCY | 0.2 | 1.1 | Negative | 30 |
| | CCECEP | 0.8 | 3.4 | Negative | 30 |
| | CCECFE | 0.2 | 1.8 | Negative | 30 |

TABLE 5-continued

Summary results

| Vaccine Group | ID | Serology RFFIT (IU/ml)* Pre-challenge (Day 392 post-vaccination)* | Serology RFFIT (IU/ml)* Post-challenge (day of euthanasia) | Rabies fluorescent antibody results Brain sample | Morbidity/ Mortality** Day of death post- challenge |
|---|---|---|---|---|---|
| Negative control group from study 10-074 | CBCCTX | ≤0.2 | ≤0.2 | Positive | 13 |
| | CBDCCE | ≤0.2 | ≤0.2 | Positive | 17 |
| | CBDCCY | ≤0.2 | 0.4 | Positive | 12 |

*All dogs euthanatized prior to Day 30 post-challenge demonstrated clinical signs of rabies infection.
**CBCCTX, CBDCCE and CBDCCY pre-challenge day was Day 752.

None of the Group C dogs demonstrated any clinical abnormalities up to 30 days post challenge. All dogs in the negative control group developed clinical signs compatible with canine rabies infection between Days 12 and 17, such as change in behavior, lethargy, salivation, facial twitching, difficulty to swallow, and limb paralysis. All dogs euthanatized up to 17 days post-challenge were positive for rabies fluorescent antibody testing and the remaining dogs euthanatized at the end of the study were negative for rabies fluorescent antibody testing in the brain tissue. Further, no local injection site reactions (diffuse swelling, firm swelling, pain upon palpation or pruritus) nor clinically significant elevations in rectal temperature were observed following vaccination.

Discussion.

Based on the pre-vaccination titer results, the final volume of each test vaccine was adjusted to reach a target titer of approximately $10^{5.9}$ TCID$_{50}$/ml. Consequently, a lower volume was administered at vaccination for vCP3012 (Group B) which had a higher titer pre-vaccination in comparison to the other test vaccines. The selection of animals subject to rabies challenge one or two years following vaccination was based on the rabies geometric mean serology titer over a 3 month period in comparison to the reference vaccine (Group D vCP65A). Group A (vCP3006) did not meet the challenge criteria, therefore dogs pertaining to that group were released from the study on Day 151. Groups B and C clearly met the challenge criteria. One and two-year duration of immunity evaluation was selected for vCP3015 and vCP3012, respectively. The selection of which test vaccine to evaluate first was based on the serology results and the construct with the lowest number of rabies G gene copies. Since the vCP3015 construct contains 2 copies and the vCP3012 contains 4 copies, vCP3015 was thus selected to be evaluated first. The two year duration of immunity evaluation will be conducted in dogs vaccinated with vCP3012 and compared to the reference group (vCP65A).

These results demonstrated the vCP constructs were safe when administered once via the subcutaneous route in dogs. Dogs vaccinated via the subcutaneous route with a single-dose of a construct containing 2 copies of the rabies G gene and the immunomodulator OX40L (vCP3015) at $10^{5.87}$ TCID$_{50}$/ml were protected against a virulent rabies challenge 1 year after vaccination. vCP3012, containing 4 copies of the rabies G gene and OX40L, induced an earlier and stronger rabies antibody response in comparison to all other vCP constructs, and will be evaluated by rabies challenge at 2 years post-vaccination.

Example 6

Other Effective Antigen/OX40L Combinations

Inventors envision many other combinations of antigen and OX40L will result in poxvirus-vectored vaccines having improved efficacy over poxvirus expressing the same antigen alone. Table 3 presents a non-limiting list of antigen and OX40L combinations, where the OX40L is selected based upon its likely ability to function as an effective genetic adjuvant in the target animal. FIG. 38 presents the alignment of known/putative OX40L from a variety of different species. A skilled person will appreciate that OX40L proteins may also vary somewhat within a single animal genus or species (e.g. *Canis familiaris*). Thus, OX40L proteins having sufficient homology to SEQ ID NO:12 should also function as effective genetic adjuvants in canine, and are encompassed by the instant invention. Additionally, inventors envision similar results are likely achievable using other vectors, including viral vectors, to express in vivo in an animal host genes encoding an antigen and an adjuvanting OX40L. For example, viral vectors include but are not limited to: DNA viruses, RNA viruses, herpes viruses, adenoviruses, adeno-like viruses, leukemia viruses, Newcastle disease virus (NDV), infectious bronchitis virus (IBV), infectious bursal disease virus (IBDV), marek's disease virus (MDV, SB1, and HVT), etc.

TABLE 3 combinations of antigen and OX40L, which are envisioned to function as genetically-adjuvanted, effective vaccine compositions

| Antigen | Target Animal | OX40L |
|---|---|---|
| Influenza, distemper (CDV), CPV, west nile, coronavirus, | Canine | SEQ ID NO: 12, or variant thereof having comparable adjuvancy in canine |
| Influenza, FCV, FeLV, FIPV, FIV, WNV, etc. | Feline | SEQ ID NO: 63, or variant thereof having comparable adjuvancy in feline |
| Influenza, WNV, E/W encephalitis virus, EHV, herpesvirus, vesicular stomatitis, infectious anemia, arteritis, AHSV, Hendra, etc. | Equine | SEQ ID NO: 64, or variant thereof having comparable adjuvancy in equine |
| BRSV, BVD, herpesvirus, pleuropneumoniae, adenovirus, parvo, enterovirus, FMDV, BTV, | Bovine | SEQ ID NO: 65, or variant thereof having comparable adjuvancy in bovine |
| PCV2, PRRSV, FMDV, BVD, Aujeszky's disease, Nipah, etc | Porcine | SEQ ID NO: 66, or variant thereof having comparable adjuvancy in porcine |

TABLE 3-continued combinations of antigen and OX40L, which are envisioned to function as genetically-adjuvanted, effective vaccine compositions

| Antigen | Target Animal | OX40L |
|---|---|---|
| MDV, SB1, HVT, NDV, IBDV), IBV | Avian | SEQ ID NO: 70, or variant thereof having comparable adjuvancy in avian |
| BTV, etc. | Ovine | SEQ ID NO: 71 |

The following numbered paragraphs provide non-limiting embodiments.

1. A composition comprising:
a) an expression vector comprising a polynucleotide encoding both:
i. one or more polypeptide selected from a Rabies G, an influenza, an FMDV, a BTV, a PCV2, a PRRSV, a WN V, a Nipah virus, a leukemia virus, a leishmania virus, an FIV, an FIPV, a FCV, an AHSV, a VSV, and an immunogenically effective variant or fragment thereof; and
ii. an OX40L polypeptide, or a comparably adjuvanting variant or fragment thereof; and
b) a pharmaceutically or veterinarily acceptable vehicle, diluent or excipient.
2. The composition of paragraph 1 wherein the vector comprises a polynucleotide encoding an OX40L polypeptide from the target animal (i.e. type of animal to which the composition will be administered).
3. The composition of paragraph 2 wherein the OX40L polypeptide is at least 90% identical to the sequence as set forth in SEQ ID NO:12 (for canine target), SEQ ID NO:63 (for feline target), SEQ ID NO:64 (for equine target), SEQ ID NO:65 (for bovine target), or SEQ ID NO:66 (for porcine target), SEQ ID NO:70 (for avian target), SEQ ID NO:71 (for ovine target), or SEQ ID NO:67 (for primate target).
4. The composition of paragraph 3 wherein the one or more polypeptide is a Rabies G polypeptide, and the target animal is a canine or a feline.
5. The composition of paragraph 3 wherein the one or more polypeptide is a BTV polypeptide, and the target animal is a bovine or a sheep.
6. The composition of paragraph 3 wherein the one or more polypeptide is a FMDV polypeptide, and the target animal is a bovine or a porcine.
7. The composition of paragraph 3 wherein the one or more polypeptide is a PRRSV polypeptide, and the target animal is a porcine.
8. The composition of paragraph 3 wherein the one or more polypeptide is a PCV2 polypeptide, and the target animal is a porcine.
9. The composition of paragraph 3 wherein the one or more polypeptide is a leukemia virus polypeptide, and the target animal is a feline.
10. The composition of paragraph 3 wherein the one or more polypeptide is an influenza polypeptide, and the target animal is an equine, a canine, or a feline.
11. The composition of paragraph 3 wherein the one or more polypeptide is a WNV polypeptide, and the target animal is a canine or an equine.
12. The composition of paragraph 3 wherein the one or more polypeptide is capable of eliciting an immune response in an avian animal.
13. The composition of paragraph 12 wherein the polypeptide is from NDV, MDV, IBD, or IBDV.
14. The compositions of any one of paragraphs 1-4 wherein the expression vector is MDV, NDV, IBD, IBDV, adenovirus, adeno-like virus, or a herpesvirus.
15. The composition of paragraph 4 wherein the Rabies G polypeptide in encoded by the sequence as set forth in SEQ ID NO:5.
16. The composition of paragraph 4 wherein the OX40L polypeptide is at least 90% identical to the sequence as set forth in SEQ ID NO:12.
17. The composition of paragraph 13 wherein the OX40L polypeptide has the sequence as set forth in SEQ ID NO:12.
18. The composition of any one of paragraphs 1-4 wherein the expression vector is a recombinant poxviral vector.
19. The composition of paragraph 15 wherein the vector is canarypox.
20. The composition of paragraph 16 wherein the vector comprises the sequence as set forth in SEQ ID NO:23.
21. A vector comprising a polynucleotide encoding both:
(a) one or more polypeptide selected from Rabies G Rabies G, an influenza, an FMDV, a BTV, a PCV2, a PRRSV, a WNV, a Nipah virus, a leukemia virus, a leishmania virus, an FIV, an FIPV, a FCV, an AHSV, a VSV, and an immunogenically effective variant or fragment thereof; and
(b) an OX40L polypeptide, or a comparably adjuvanting variant or fragment thereof.
22. The vector of paragraph 21 wherein the OX40L polypeptide is at least 90% identical to the sequence as set forth in SEQ ID NO:12 (for canine target), SEQ ID NO:63 (for feline target), SEQ ID NO:64 (for equine target), SEQ ID NO:65 (for bovine target), SEQ ID NO:66 (for porcine target), or SEQ ID NO:71 (for ovine target).
23. The vector of paragraph 22 wherein the one or more polypeptide is a Rabies G polypeptide, and the target animal is a canine or a feline.
24. The vector of paragraph 22 wherein the one or more polypeptide is a BTV polypeptide, and the target animal is a bovine or a sheep.
25. The vector of paragraph 22 wherein the one or more polypeptide is a FMDV polypeptide, and the target animal is a bovine or a porcine.
26. The vector of paragraph 22 wherein the one or more polypeptide is a PRRSV polypeptide, and the target animal is a porcine.
27. The vector of paragraph 22 wherein the one or more polypeptide is a PCV2 polypeptide, and the target animal is a porcine.
28. The vector of paragraph 22 wherein the one or more polypeptide is a leukemia virus polypeptide, and the target animal is a feline.
29. The vector of paragraph 22 wherein the one or more polypeptide is an influenza polypeptide, and the target animal is an equine, a canine, or a feline.
30. The vector of paragraph 22 wherein the one or more polypeptide is a WNV polypeptide, and the target animal is a canine or an equine.
31. The vector of paragraph 23 wherein the Rabies G polypeptide is encoded by the sequence as set forth in SEQ ID NO:5.
32. The vector of paragraph 22 wherein the polynucleotide encodes a Rabies G polypeptide having the sequence as set forth in SEQ ID NO:1 and an OX40L polypeptide having at least 90% identity to the sequence as set forth in SEQ ID NO:12.

33. The vector of paragraph 21 wherein the vector is a poxvirus.

34. A method of vaccinating an animal comprising administering at least one dose of the composition of any one of paragraphs 1-14.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A vaccine composition comprising or consisting essentially of:
   a) a recombinant poxviral vector comprising a polynucleotide comprising four Rabies G genes and one canine OX40L gene, each expressing in vivo in an animal host in need thereof; and
   b) a pharmaceutically or veterinarily acceptable vehicle, diluent or excipient; and
   wherein two of the Rabies G genes are classic genes and two of the Rabies G genes are codon-optimized genes; and
   wherein the vector comprises the sequence as set forth in SEQ ID NO: 23.

2. The vaccine of claim 1, wherein the animal is a canine.

3. The vaccine of claim 2, wherein at least one of the Rabies G genes has the sequence as set forth in SEQ ID NO:5.

4. The vaccine of claim 2, wherein the OX40L polypeptide is identical to the sequence as set forth in SEQ ID NO:12.

5. The composition of claim 1, wherein the recombinant poxviral vector is canarypox.

6. The composition of claim 5, wherein the vector is canarypox ALVAC.

7. A recombinant poxviral vector comprising at least one polynucleotide encoding:
   (a) four copies of a Rabies G polypeptide; and
   (b) a canine OX40L polypeptide;
   wherein the polynucleotide comprises a gene encoding the OX40L polypeptide, inserted into the vector's C6 locus; and
   wherein the polynucleotide comprises genes encoding the Rabies G polypeptides, inserted into the vector's C3 loci and C5 loci;
   and wherein the vector comprises the sequence as set forth in SEQ ID NO: 23.

8. A method of vaccinating an animal comprising administering at least one dose of the composition of claim 1.

9. The method of claim 8, wherein only one dose of the composition is administered to the animal.

10. The method of claim 9, wherein the animal is a canine or a feline.

11. The method of claim 10, wherein the animal is a dog.

12. The method of claim 11, wherein the one dose elicits an sufficient immune response in the dog to provide protective immunity for at least 3 years.

13. The vector of claim 7, wherein the vector comprises:
   (a) one (1) copy of a canine OX40 ligand gene, inserted into the vector's C6 locus;
   (b) two (2) copies of a classic Rabies virus G gene, inserted into the vector's C5 loci; and,
   (c) two (2) copies of a codon-optimized Rabies virus G gene, inserted into the vector's C3 loci.

14. The vector of claim 7, wherein the canine OX40 ligand gene has a sequence as set forth in SEQ ID NO:10; the classic Rabies virus G genes each have a sequence as set forth in SEQ ID NO:16; and, the codon-optimized Rabies virus G genes each have a sequence as set forth in SEQ ID NO:5.

15. The vector of claim 13, wherein the OX40 ligand gene and the Rabies G genes are operably linked to promoters selected from 42K, I3L and H6.

16. The vector of claim 15, wherein the OX40 ligand gene is operably linked to a 42K promoter having the sequence as set forth in SEQ ID NO:9; the two classic Rabies G genes are each operably linked to an H6 promoter having sequence as set forth in SEQ ID NO:15; and, the codon-optimized Rabies G genes each are operably linked to an I3L promoter having the sequence as set forth in SEQ ID NO:4.

* * * * *